(12) United States Patent  
Dogimont et al.

(10) Patent No.: US 7,576,264 B2  
(45) Date of Patent: Aug. 18, 2009

(54) **GENE RESISTANT TO *APHIS GOSSYPII***

(75) Inventors: Catherine Dogimont, Vedene (FR); Abdelhafid Bendahmane, Le Coudray Montceaux (FR); Michel Pitrat, Montfavet (FR); Emilie Burget-Bigeard, Lattes (FR); Lynda Hagen, Caumont-sur-Durance (FR); Aline Le Menn, Villeneuve-Lès-Avignon (FR); Jérôme Pauquet, Aspiran (FR); Patrick Rousselle, Chateauneuf-de-Gadagne (FR); Michel Caboche, Maurepas (FR); Véronique Chovelon, Vedene (FR)

(73) Assignee: Genoplante-Valor (FR)

( * ) Notice: Subject to any disclaimer, the term of this patent is extended or adjusted under 35 U.S.C. 154(b) by 184 days.

(21) Appl. No.: 10/542,337

(22) PCT Filed: Jan. 13, 2004

(86) PCT No.: PCT/FR2004/000050

§ 371 (c)(1),  
(2), (4) Date: Mar. 10, 2006

(87) PCT Pub. No.: WO2004/072109

PCT Pub. Date: Aug. 26, 2004

(65) Prior Publication Data

US 2007/0016977 A1 Jan. 18, 2007

(30) Foreign Application Priority Data

Jan. 13, 2003 (FR) .................................. 03 00287

(51) Int. Cl.  
*C12N 15/09* (2006.01)  
*A01H 5/00* (2006.01)  
*C12N 15/29* (2006.01)  
*C12N 15/82* (2006.01)

(52) U.S. Cl. ........................ 800/302; 800/278; 800/298; 800/309; 800/308; 800/307; 435/320.1; 435/468; 536/23.6

(58) Field of Classification Search ....................... None  
See application file for complete search history.

(56) References Cited

U.S. PATENT DOCUMENTS 6,613,962 B1 * 9/2003 Vos et al. ..................... 800/301

FOREIGN PATENT DOCUMENTS

WO WO 98/30083 A 7/1998

OTHER PUBLICATIONS

Dogimont et al. Proceedings of IXth EUCARPIA Meeting on Genetices and Breeding of Cucurbitaceae, France, May 21-24, (2008).*  
Brotman Y. et al., "Resistance gene homologues in melon are linked to genetic loci conferring disease and pest resistance", *Theoretical and Applied Genetics*, vol. 104, No. 6-7, May 2002, pp. 1055-1063.

* cited by examiner

*Primary Examiner*—Medina A Ibrahim  
(74) *Attorney, Agent, or Firm*—Alston & Bird LLP

(57) ABSTRACT

The present invention relates to isolated Vat genes encoding a polypeptide that confers resistance to *Aphis gossypii* and/or resistance to viral transmission by aphids, and methods of transforming plant and cells with a Vat gene. The invention also relates to transgenic plants and cells having resistance to *Aphis gossypii* and/or resistance to viral transmission by aphids.

12 Claims, 14 Drawing Sheets

```
CCGGAGTGTACATAATAAGGAGACACCATCACAAGTCTTGAAGCTTTGGCGCTCTTGAAATTCAGCTTTTAAATT
AATTAGTCATGTTTTTCAAATATATAACATAGGAGAATATGAGTTTTGCGTCAAATCCCATCTTGGCAGAGTGTA
TTTTGATGAAATTCCTTATTGGAAGGAACTGCCATATTTTTAGAATTTGGAATCTGTAAAGTTATTCTCATGTGG
TTTTTTGGGCAGTGGAGGGAGTTGGAGAAGTTGATTGGTGTGCAGATCTATGTATAGGACAGATCATTGAAGAGG
AAAAAAGAATTGGAATATTAGGGATTTGGTTAATTAAGCAATATGGGAAGTTGGATTTCAGAATTGCAATTCATG
ATTGGGTTTCGATTTAGGAAGAATGGACTTGCAAATTCAATTTAACATAAAATTTCTTTTTTTTTTCCTAAATTA
ATTTTTATTTGATCTTCGGACTCATCCAATGCAATTTACAGGTCACTACAAACAATATCCATGTCAGCACACATA
ACGTGTCTAGTAGACATTACGTTAACTTAATGTAGGAAACAAAAAGAAAAACGAAAAAGGCAAGAAATGAAAAAG
GAAACGTTGTGTATGATGATTAAAATGTACGTTGATAGCTAAATTCAACTTTGTTCTTCATTAGCAACAACAAGG
GACAACAAAATGAAAATTTCAGCACAGTTATGGAATGTTGAAGAAGAAGGTGACGAGAGAGATGCCACATCATAA
AAAATTAATATTATAATCATTTTTGTCACATCAGTTTTCTGATTACTTATATTTAACCTACACATCATTTTGCCG
TTACTCAACTAACGATCGATATGACCTTTAAAGCTCGATGATTAAAATGTTTATTTTGAACTTTCAGGGACTATA
TAAATGTATATATATCAACTTCAAATCTTAGCGGTCAAAAGTGCATTTTGTTTTAGTTTAAAACACCGAGATGTG
ACGATTAATAATGCCTACACACTCACGTACTCACACATGCAGTGAGTTTTTTATGTTTTTTTTACACACATTAGA
CGCAAATTGAATTCCTAATTCCATTCCCTAAGACAAGTTTCTAATGACTTATACAATTCACATAGGCATGCATGC
AGAACAAGCGAAAAACGACGAATTTACCTTAAGAAAATGGCCCAACCAACCACTTACACAATCTCAGGCATACCA
TTCCCCGGGATGAAAGAATTTTGCCTGTAATTCATTCGATCTCAGGCATACAATGCATCGAGAAGACGCAAAATG
AAAGACAAAAGTATAGAACAACACAATCCTGTACTTCATTTTAAACGATAGTTTTCAAATTTAACGATCGTGTAG
ATCATGATACACGATCTCGAGCCTTAGTGGCACCGAGATGGCCCGAGATGAAAGAATTATGTCTTTATTTTATTC
GATATTAAGCATACATTACTTCGAGATGAAAGACCTCTACCTTTAGTTATTCGATCTCGAGCCTTAATTGAATCG
AGATGACCCAAGATTGATAGATCGCAAAGAAGATATATATCGTAAGGGCATATATGAAATTTATGAAAATACGAT
CATGTGTCATAAACTTTTCTTATTTTGTTATATAGACCGTAAATATTATAGATTTTGGTTACATTTGTGTAAATT
ACTCTATTTTTTTTAGTAAAACAAATGAATTAAATTTTTAAAAAAAAATTATTGAGAGTTGAAGTAATTGGGT
GTTTTCTAAAAGATTGAAATAAATACCTTTATTAACTTTGCAAATATATTTCAAAGAGGCTAACAAATCAAATA
TATTTTCTAAAAAAATCACATTGCGTTGGGGATAAGGTAAGAGTAATGGAAAAATGAAAGGTTGTGAACAATTCG
TACTCTTACTTATGAGATTTGACAGAACAAATATTTTTCAAATACTCTTTTTACGTTTTCTTTTTTAAAATTAAA
TAACAAATACTTTTCCACTGCTTTTCTTTTCTTCCATTGACTCCTCAACTAATAATTTTGGTCTTCCCATTATTA
TCTTCTTCTTCTTCATTTTTCTCTGCACTGTCTCTTCTCCATTTCAACATCTTCTTATATCTTCATTCAGGTTAA
ATATTTCATCCCTTACCATTTTTATTTACATTTTCCATCTGATCATTTCTATACTTATAAACTCGATAATTTGTT
TAGACTTTCTTTAGATAGTTTTTACTTGGTGATCTGTATGTGTTCACTCCTACTTTTCTGTTAGGCAAAATCTTC
AAAATTATTATGGTTCATTCCTCGTGGTTTTTTAGCTCTTCAAGTATTTTGTAGGTTTTGATCCTTTTCAAGCT
CAAGAACAGAGGATAATAATGGACATCCTTATTTCAGTCACTGCAAAAATTGCCGAATACACTGTTGAGCCTGTT
GGACGCCAACTTGGTTATGTATTTTTCATTCGTTCCAACTTTCAAAAACTTAAGACTCAAGTAGAAAAGCTGAAG
ATTACAAGAGAGTCTGTGCAACACAAGATCCATAGTGCAAGAAGAAATGCTGAAGACATAAAACCTGCCGTTGAG
GAATGGTTGAAAAAGGTCGATGACTTTGTCCGAGAATCTGACGAGATATTAGCCAATGAAGGTGGACATGGTGGA
CTCTGTTCCACCTATTTGGTCCAACGACACAAGTTAAGTAGAAAAGCAAGCAAAATGGTAGATGAGGTTCTTGAG
ATGAAAAATGAGGGGAAAGTTTTGATATGGTATCCTATAAAAGTGTTATCCCATCAGTTGATTGTTCACTTCCA
AAAGTGCCTGACTTTCTTGACTTTGAGTCAAGAAAGTCGATTATGGAACAAATCATGGATGCACTATCTGATGGT
AATGTCCATAGGATTGGAGTATATGGGATGGGGGTGTTGGCAAAACAATGCTAGTGAAGGATATTTTAAGAAAA
ATTGTGGAGAGTAAGAAGCCTTTTGATGAGGTGGTAACATCACGATCAGCCAAACACCAGATTTTAGAAGTATC
CAAGGACAACTAGCTGACAAGCTAGGTTTGAAATTCGAACAAGAAACAATAGAAGGAAGGGCTACTATTCTACGA
AAGAGGTTAAAGATGGAGAGAAGTATCCTAGTTGTGTTGGATGATGTTTGGGAGTATATTGATTTGGAAACTATA
GGAATTCCAAGTGTTGAAGATCATACGGGGTGCAAGATCTTGTTTACCACTAGGATTAAACATTTGATCTCAAAT
CAAATGTGCGCCAATAAAATTTTTGAGATAAAAGTTTTAGGAAAAGATGAGTCATGGAATTTATTTAAGGCAATG
GCAGGTGACATTGTTGATGCAAGTGATTTGAAGCCTATAGCCATTCGAATTGTGAGAGAATGTGCAGGTTTGCCT
ATTGCTATTACTACTGTTGCTAAGGCATTACGAAATAAACCTTCCGACATTTGGAATGATGCCTTAGATCAGCTT
AAAACTGTTGATGTGGGTATGGCAAACATTGGAGAAATGGAAAAGAAAGTGTATTTGTCACTAAAACTGAGTTAC
GATTGCTTGGGATATCAACAGGTGAAGTTATTATTCTTGTTATGCAGCATGTTTCCAGAAGACTTTAGCATTGAC
GTGGAAGGGTTGCATGTATATGCCATGGGCATGGGATTCTTACATGGTGTTGATACTGTGGTAAAAGGACGACGT
AGGATAAAAAAATTGGTTGATGATCTTATATCTTCTTCTTTGCTTCAACAATATTCTGAGTATGGGTGCAATTAT
GTGAAAATGCATGATATGGTTCGTGATGTAGCCCTATTAATTGCATCTAAGAATGAACACGTACGTACATTGAGC
```

FIG. 1

```
TATGTGAAAAGATCGAATGAAGAATGGGAAGAAGAGAAACTATTGGGTAATCATACCGCAGTGTTCATTGATGGT
TTACATTATCCTCTCCCGAAGTTAACGTTACCCAAAGTTCAATTATTAAGGTTAGTTGCAAAATATTGTTGGGAA
CATAATAAGCGTGTGTCGGTGGTAGAAACTTTTTTTGAAGAAATGAAAGAGCTCAAAGGTTTAGTAGTAGAAAAC
GTAAATATATCATTGATGCAACGACCATCTGATGTTTACTCCTTAGCAAACATCAGAGTATTACGTTTGGAAAGA
TGTCAATTATTAGGGAGCATAGATTGGATTGGTGAATTAAAAAAGCTTGAAATTCTTGATTTTAGTGAATCTAAC
ATCACACAAATTCCTACAACCATGAGCCAATTGACACAGCTAAAAGTGTTGAATTTATCTTCTTGTGAACAACTT
GAGGTAATTCCACCAAATATTCTTTCAAAGTTGACAAAATTGGAAGAATTAGATCTGGAAACTTTTGATGGATGG
GAAGGAGAAGAATGGTATGAAGGAAGGAAAAATGCTAGCCTTTCTGAACTCAAGTGCTTGCGACACCTTTATGCT
TTAAACTTAACCATTCAAGATGAAGAAATTATGCCAGAAACTTGTTCTTAGTTGGGAAGTTGAAGCTTCAAAAA
TTCAACATTTGTATTGGTTGCGAAAGCAAATTAAAGTATACTTTTGCATACAAGAACAGAATCAAAAACTTCATT
GGAATCAAGATGGAATCAGGAAGGTGCTTGGATGATTGGATAAAAAATTTGTTAAAGAGGTCGGACAATGTGCTT
TTGGAAGGATCAGTTTGTTCAAAGGTTCTCCACTCAGAATTGGTAGGTGCCAATAACTTCGTAAGTTTGCAGTAT
CTCTACCTTTATGATAATTCAAAATTTCAACATTTTATCAACGTTAGCAATACCATCAACATTGAAGAATCATTT
TTTAGTGAAATGGTAAATTTCATCAACACATTTTTCTATGTTTCTATATACACATCAAAATTTATAAATCACCTG
TTTGTTCATTTTTATTGTTCCTTCCACAAGTTCCTTCTAACATTTGTGGTTAGTAATGATATTAGGGATAAGATT
CTATTCTTCTTTGTTTTAGAAGGCTCTTCTCTTGGTGTAGAGAGACTCTTTCTTGTTTCATACATTAATGATAAT
ATATAATTTTAGACTTCTAAAATATATAAATGCATGTCAGGTGATATTCCAAGAAAATTTAAAGAAGTTTATTAG
ATATTTCCTATCTAAGGAAGCAAATTTGAAGTAATCATTTTACACAATTTGTTATGGTAATTTTAAAACACTATA
TAAATTATATGTTGTTAGTTAGCATCAGTTGTGATGATATGGTTAATTACGTTGTCACAAACTGAACTTTTAAGG
ACGTAAATTTGTAGGTATCACTTCCTAATTTGGAGAAGTTGGAAATTGTGAATGCAAAGAGTTTGAAGATGATAT
GGAGCAATAACGTGCCAATTCTTAATTCCTTTTCCAAACTCGAGGAAATAAAAATTTATTCATGCAACAATCTTC
AAAAAGTATTATTTCCTCCAAATATGATGGACATTCTCACATGCCTTAAAGTCTTAGAGATCAAAAATTGTGATT
TGTTGGAAGGGATATTTGAAGCGCAAGAGCCAATTAGTGTTGTTGAGAGCAATAATTTACCCATTCTTAATTCCT
TTTCCAAACTCGAGGAAATAAGAATTTGGTCATGCAACAATCTTCAAAAAGTATTATTTCCTTCAAATATGATGG
GCATTCTTCCATGCCTTAAAGTCTTAGATATTAGAGGTTGTGAATTGTTGGAAGGGATATTTGAAGTGCAAGAGC
CAATTAGTGTTGTTGAGAGCAATAGTGTACCCATTCTTAATTCCTTTTCCAAACTCGAGAAAATAAGAATTTGGT
CATGCAACAATCTTCAAAAAATATTATTTCCTTCAAATATGATGGGCATTCTTACATGCCTTAAAGTCTTAGAGA
TCAGAGATTGTGAATTGTTGGAAGGGATATTTGAAGTGCAAGAGCCAATTAGTGTTGTTGAGAGCAATAATTTAC
CCATTCTTAATTCCTTTTCCAAACTCGAGGAAATAAGAATTGGGTCATGCAACAATCTTCAAAAAGTATTATTTC
CTCCAAATATGATGGGCATTCTTACATGCCTTAAAGTCTTAGAGATTAGACATTGTAATTTGTTGGAAGGGATAT
TTGAAGTGCAAGAGCCAATTAGTATTGTTGAAGCGAGTCCTATCTTGCTCCAAAATTTATCTTCGTTGATGTTAT
GTAATCTTCCAAACCTTGAGTACGTGTGGAGCAAAAATCCTTATGAACTTCTGAGTTTGGAAAATATAAAAAGTT
TGACCATTGATAAATGTCCAAGACTTAGAAGAGAATACTCAGTCAAAATTCTAAAGCAACTTGAAGATGTAAGCA
TAGATATCAAACAATTGATGAAGGTTATTGAGAAGGAAAGTCAGCACATCATAATATGTTGGAATCAAAGCAAT
GGGAGACTTCATCTTCTTCTAAGGTACGTATATATTCTACAAGAAAACATGTTTGTTCAATTTAATTTTCAGAAA
ATAAATTGTTTTCAAGAATTAGTTGAACAGAATTGGTTCTGTTAGTTGAACAGAGTTTTAAAGAAAACAAATTAT
TATGTTTGTTCTAGAAACCTATGGAAATTAGTGTTATTAGGGGTTAATTATTTACCTGAATTAAAAAAGAATAAG
CAAGTAAACCGCTTAATTTTAATATGTTTATCAATAGAAATTAGGATCCGTTTGGATTGACTTGAATGATATGTT
TTCCTGGAAAGAAACTCATTTTTGTTTGAACTCATTTTTATGAAAATTGGCTAAAATATATTTAAAAAATTAGGT
GGCTTTCAAATATTCAATTTTTTTTTAAAATAACTTATTTTTTGAATTAAACACTCCAAAATGTAATTCAAAAA
CACCCCTAAGTTAATTAGATATATAATTAATACATAAATTAATTAATTTTATTTAGTTGAGTTAAATTAGTTTTA
ATGCAAACAATAATATATTTTATAGCCAATATACAAGAATGAAAGTAAGAAAAGAAGACAAAAAAAAATGATAT
GTTAATTAGAATTTTACATAAAGAATGATCTGATTAAAAGCTAATCTCTATCGATATAGTTTTTTAATTATATTA
AATATAGTAAGTAGTCCATTATAATAATTGAATTTTTTGTACCAAATTAATTAAACTAATTCTTTTTACTAATT
ATTGAATATTTAAGATATTTTTGGCTAATTAATTAATAATTTGTGTGCAAATATAAGTTATTATTGCATTTATTT
AATAGATTTTGATCATCAGGATGGGGTTCTACGGCTGGGAGATGGTTCTAAGTTGTTTCCAAATCTTAAAAGTTT
GAAGCTATATGGTTTTGTTGATTATAACTCAACCCATTTACCAATGGAAATGTTGCAAATCTTATTCCAACTTGT
AGTCTTTGAATTGGAAGGAGCATTTCTTGAAGAAATTTCCCCAGCAACATACTGATTCCAAGCTATATGGTTTT
AAGAAGATTAGCTCTATCTAAACTACCCAAGCTTAAGCATTTGTGGAGTGAAGAATGCTCACAAAACAATATCAC
CTCAGTTCTTCAACATTTGATTTCTCTAAGAATTTCAGAATGTGGAAGATTGAGTAGTTTACTGTCGTCAATAGT
GTGTTTTACAAACTTGAAACATCTTCGGGTTTATAAATGTGATGGACTAACCCATTTGCTGAATCCTTCGGTGGC
```

FIG. 1 (continued)

```
TACAACGCTTGTGCAACTTGAGTCTTTGACAATAGAAGAATGCAAAAGGATGAGTAGTGTAATTGAGGGAGGATC
AACCGAAGAAGATGGAAATGATGAAATGGTTGTATTCAACAACCTACAACATTTATACATTTTTAATTGTTCCAA
CCTAACAAGCTTTTATTGTGGGAGATGCATTATTAAATTTCCATGTTTGAGGCAAGTAGACATTTGGAACTGTTC
TGAAATGAAGGTCTTTTCGCTTGGAATTGTAAGCACACCTCGATTGAAATATGAAAATTTTTCTTTAAAGAATGA
TTACGATGATGAACGGTGTCATCCAAAATATCCCAAAGATATGTTGGTGGAAGATATGAATGTCATCACCAGAGA
ATATTGGAGGATAATGTTGATACCGGAATTCCAAATTTATTTGCCGAACAGGTTTGTATATTTAATTACCTTTT
CATATTTGGTAATAATTAATTTTTATTATTTGTGTGTTAGAGTATGAACTTTAATGAATTTATTTAATTAATGCA
GAGTTTGGAGGAAAACCGATCTGAAAATTCTTCTTCTTCGAAGAATAATGTTGAGAAAGAATAAGGAATTATATG
GATATTGTTGTACACTACTTAATATATCATTTCATCCACAAGGAAAAGGTCAGAATCTTGAAATCCTCCATTCTT
TTTTATGAGAGAATATCATCCAATGTCAAATTGAAAAGTCTCGATAGATTTGTTAAATTAACTTTTGATACAAGT
CATAAAATGTTAATTAGTATAATAATAATATATCTGATCCCATCAAATTAATTAGAAGTAACGACAAATTTAACT
TCTGTAATATCAATTCAATTTGATGTCTCAATCAACTGCATAAAATTTGATGTCACAAATTTAACTTCTGTAATG
TGAATCTTTTTTTTTTTCCCTTTGCACATAAAACCAACAAGTTAAAATAGATATAACAAAGAATTTAATTCACA
TATAATAAATTCATCCAATATAATGTTCTTTCACCTTTTTCTCTCTTTCACAAAACTGTAATAATAATATCTACC
ACAAAAGGTAAACCATTAATATGATTCTTCAAGAAGGTTGTTTATTTGGTCAAATTTTCATGAAAGTATTAATAC
AGTGTATGTTTTGCAAAGGAAGCTGCCAAATACCTACCTCAATCCTAGCAGATGCGTTCTTTGCAAGTTGGCTGT
CAAAGACTTGAACCATATTTTCACAACCTGTGCCAATTCGCAAATAGCCTCTGGGTCAAACTGCACGACAAAATT
GGTGGAAACTTTGATACAAACAGTATCAAAGCCCTCTGTTGGTCTCTTGGCTCGCTGAAACAATCAAACAGAAAG
AACATCATTCTCTCGATGTAGGTGTGGATCTTCTTTAGTCCATTTGGGTGGAAAGAAACAATAGGATTTTCATAG
ACACAGAAGAAGCTTAGTCACATTTGGGAAGATATCGAAACTTTGATTGGACCATGGTCGAGTAGAAACAAAAT
GTTCAAAGACTACAATCCAACATCAATCTTTAAACTTTAGAGCTTTGTTAGATTAATGTTTGTTGTATATGGCTT
CCCTGTAGCCAAAGAAATATACATTGTAACAATGGTTTGATGAAATGATAATGAAGTGGTATGGTGTGTTTCAAT
TGCAAAAAATATGATTCTTCAAGAAAGGCCGAGAGGATAAGATTGTGATCGTGCCATGCGCTTGGGTTGTGATTT
AATTACAAATATATTCATATAGTATTTGGAGCAAAACAGTCCTAATTAATTAAATATAATGCGTTATTTTATTTT
TCTGAATAAGTTAAATTTAACCACTAGAAATTTTTTTACTAAGTGAACATTTTCATAGCACTTTCATAATCCCCA
CTTCATTAAAATGAATCAATAAAGTTCAAGGAAAGTGTAGAATGATGAATCTAAAAGAAACAAAAAACAAGGTAT
ATAAGTTTAAAGCAACGGTGGTAGCACTGTAATGATCCGAGGGAGTACACATTTTTTCATAAATTATTTTATTAT
CATCAATAGAAGAATTCGAATTTCTTTTATCTTTTAATTGATAATATAATTTCATAATTAGCTATAAGTGGATTT
TTCAAATGATTGGATCCACATACATATCAACTTCGATCAAATTATTAAAGGTATAATTTTAAATCACTAAGAAGA
AAAGGATTGATGGTGGGCCTTATGCTATTATACACTTTGAGTACCCTCTCGGCCTCAACAAGATTCCCAAGTTCA
ATAATTGAAACTTTGAAAAATGTGTGCAATCACATGTATTCAATTTCTATGTCGGTATCACATATTTTCATGTTT
CCATACGTTTAATTTCCATATAAAAGTGAATCCATAATTTTATTATATTGCGAAAAAATCTACCAAACATGGAAA
TTAGCTATGAAAATATTAGTAATATAAATAATGGATATGTTGACTTATTTGAAAAAAATTAAAAAAATATTCATT
TATGGGTTTAAATTTATTTTTAAATTTTTTGTTTTTATATATTATTTTAAAAATATATATTGAAATTAATATTTT
ATTGATATTATATCATCAAAATTTTTGTAAAATTAAGATCATTAATATAACGCCCCAGACCCAAGATTTGGAATT
CGGATCCCTGACATTCTTTTGCATCCACTGTGATCTGATAACATCATCTTTACTTGTCTTAAATTATTAGACTGA
AAGTTCTCTCCACAAAACAATAGGAGTCATTTCAACATACTTTGTCCTCACTCACAGCATCCCTATCACTCATAA
TTAATGTAAAATTTTATTATATTTGTAAATATGTTTTGGTGTACTTTGCCATATATTAAAACATACTACTAAACA
AAACGAAATGATTAAAAAGGAAGGGAAGGTATTAAAAATTATAAATTTTAAGAAAGGAAAAGAAGAAGAAGGAAA
AAAAAAAAAAAAGAGAATGATGAGTGAGAGGCACCAAGTGAGGACATATACTACTCTTTGAGTACATAACCTAA
TGGTTAAGAAAAAAAAAAATCTCATATCAAATTCAAAGTGCCATGCTATTATTACTTAATATTTTATATGGAAGT
TAAATAAATTGTTAGAGAGAAGTCTTGTTTTCTGTCTGTTTGTTAACTCATTTTTGTAATTAATGTTTAATTTGA
TCATTGTCATTCCAATTAATTGTAACATAATTTTCTGCCCAATTTATCTCTTTTGCTTTCGTTTTTGTTTAGATA
CCCTACTCGGCTACTCCTCAACTTTTCCTCATTTCATTTTCAGTTGG
```

FIG. 1 (end)

```
             10        20        30        40        50        60
Vat   ATGGACATCCTTATTTCAGTCACTGCAAAAATTGCCGAATACACTGTTGAGCCTGTTGGA
      ::::::::::::::::::::::::::::::::: :::::::::::::::::::::::::::
Vat1  ATGGACATCCTTATTTCAGTCACTGCAAAAATTGCTGAATACACTGTTGAGCCTGTTGGA
             10        20        30        40        50        60
             70        80        90       100       110       120
Vat   CGCCAACTTGGTTATGTATTTTTCATTCGTTCCAACTTTCAAAAACTTAAGACTCAAGTA
      ::::::::::::::::::::::::::::::::::::::::::::::::::::::::::::
Vat1  CGCCAACTTGGTTATGTATTTTTCATTCGTTCCAACTTTCAAAAACTTAAGACTCAAGTA
             70        80        90       100       110       120
            130       140       150       160       170       180
Vat   GAAAAGCTGAAGATTACAAGAGAGTCTGTGCAACACAAGATCCATAGTGCAAGAAGAAAT
      ::::::::::::::::::::::::::::::::::::::::::::::::::::::::::::
Vat1  GAAAAGCTGAAGATTACAAGAGAGTCTGTGCAACACAAGATCCATAGTGCAAGAAGAAAT
            130       140       150       160       170       180
            190       200       210       220       230       240
Vat   GCTGAAGACATAAAACCTGCCGTTGAGGAATGGTTGAAAAAGGTCGATGACTTTGTCCGA
      ::::::::::::::::::::::::::::::::::::::::::::::::::::::::: ::
Vat1  GCTGAAGACATAAAACCTGCCGTTGAGGAATGGTTGAAAAAGGTCGATGACTTTGTTCGA
            190       200       210       220       230       240
            250       260       270       280       290       300
Vat   GAATCTGACGAGATATTAGCCAATGAAGGTGGACATGGTGGACTCTGTTCCACCTATTTG
      ::::::::::::::::::::::::::::::::::::::::::::::::::::::::::::
Vat1  GAATCTGACGAGATATTAGCCAATGAAGGTGGACATGGTGGACTCTGTTCCACCTATTTG
            250       260       270       280       290       300
            310       320       330       340       350       360
Vat   GTCCAACGACACAAGTTAAGTAGAAAAGCAAGCAAAATGGTAGATGAGGTTCTTGAGATG
      ::::::::::::::::::::::::::::::::::::::::::::::::::::::::::::
Vat1  GTCCAACGACACAAGTTAAGTAGAAAAGCAAGCAAAATGGTAGATGAGGTTCTTGAGATG
            310       320       330       340       350       360
            370       380       390       400       410       420
Vat   AAAAATGAGGGGGAAAGTTTTGATATGGTATCCTATAAAAGTGTTATCCCATCAGTTGAT
      ::::::::::::::::::::::::::::::::::::::::::::::::::::::::::::
Vat1  AAAAATGAGGGGGAAAGTTTTGATATGGTATCCTATAAAAGTGTTATCCCATCAGTTGAT
            370       380       390       400       410       420
            430       440       450       460       470       480
Vat   TGTTCACTTCCAAAAGTGCCTGACTTTCTTGACTTTGAGTCAAGAAAGTCGATTATGGAA
      :::::::::::::::::::::::::::::::: :::::::::::::::::::::::::::
Vat1  TGTTCACTTCCAAAAGTGCCTGACTTTATTGACTTTGAGTCAAGAAAGTCGATTATGGAA
            430       440       450       460       470       480
            490       500       510       520       530       540
Vat   CAAATCATGGATGCACTATCTGATGGTAATGTCCATAGGATTGGAGTATATGGGATGGGG
      ::::::::::::::::::::::::::::::::::::::::::::::::::::::::::::
Vat1  CAAATCATGGATGCACTATCTGATGGTAATGTCCATAGGATTGGAGTATATGGGATGGGG
            490       500       510       520       530       540
            550       560       570       580       590       600
Vat   GGTGTTGGCAAAACAATGCTAGTGAAGGATATTTTAAGAAAAATTGTGGAGAGTAAGAAG
      ::::::::::::::::::::::::::::::::::::::::::::::::::::::::::::
Vat1  GGTGTTGGCAAAACAATGCTAGTGAAGGATATTTTAAGAAAAATTGTGGAGAGTAAGAAG
            550       560       570       580       590       600
            610       620       630       640       650       660
Vat   CCTTTTGATGAGGTGGTAACATCCACGATCAGCCAAACACCAGATTTTAGAAGTATCCAA
      ::::::::::::::::::::::::::::::::::::::::::::::::::::::::::::
Vat1  CCTTTTGATGAGGTGGTAACATCCACGATCAGCCAAACACCAGATTTTAGAAGTATCCAA
            610       620       630       640       650       660
```

FIG. 2

```
              670        680        690        700        710        720
Vat    GGACAACTAGCTGACAAGCTAGGTTTGAAATTCGAACAAGAAACAATAGAAGGAAGGGCT
       ::::::::::::::::::::::::::::::::::::::::::::::::::::::::::::
Vat1   GGACAACTAGCTGACAAGCTAGGTTTGAAATTCGAACAAGAAACAATAGAAGGAAGGGCT
              670        680        690        700        710        720
              730        740        750        760        770        780
Vat    ACTATTCTACGAAAGAGGTTAAAGATGGAGAGAAGTATCCTAGTTGTGTTGGATGATGTT
       ::::::::::::::::::::::::::::::::::::::::::::::::::::::::::::
Vat1   ACTATTCTACGAAAGAGGTTAAAGATGGAGAGAAGTATCCTAGTTGTGTTGGATGATGTT
              730        740        750        760        770        780
              790        800        810        820        830        840
Vat    TGGGAGTATATTGATTTGGAAACTATAGGAATTCCAAGTGTTGAAGATCATACGGGGTGC
       ::::::::::::::::::::::::::::::::::::::::::::::::::::::::::::
Vat1   TGGGAGTATATTGATTTGGAAACTATAGGAATTCCAAGTGTTGAAGATCATACGGGGTGC
              790        800        810        820        830        840
              850        860        870        880        890        900
Vat    AAGATCTTGTTTACCACTAGGATTAAACATTTGATCTCAAATCAAATGTGCGCCAATAAA
       ::::::::::::::::::::::::::::::::::::::::::::::::::::::::::::
Vat1   AAGATCTTGTTTACCACTAGGATTAAACATTTGATCTCAAATCAAATGTGCGCCAATAAA
              850        860        870        880        890        900
              910        920        930        940        950        960
Vat    ATTTTTGAGATAAAAGTTTTAGGAAAAGATGAGTCATGGAATTTATTTAAGGCAATGGCA
       ::::::::::::::::::::::::::::::::::::::::::::::::::::::::::::
Vat1   ATTTTTGAGATAAAAGTTTTAGGAAAAGATGAGTCATGGAATTTATTTAAGGCAATGGCA
              910        920        930        940        950        960
              970        980        990       1000       1010       1020
Vat    GGTGACATTGTTGATGCAAGTGATTTGAAGCCTATAGCCATTCGAATTGTGAGAGAATGT
       ::::::::::::::::::::::::::::::::::::::::::::::::::::::::::::
Vat1   GGTGACATTGTTGATGCAAGTGATTTGAAGCCTATAGCCATTCGAATTGTGAGAGAATGT
              970        980        990       1000       1010       1020
             1030       1040       1050       1060       1070       1080
Vat    GCAGGTTTGCCTATTGCTATTACTACTGTTGCTAAGGCATTACGAAATAAACCTTCCGAC
       ::::::::::::::::::::::::::::::::::::::::::::::::::::::::::::
Vat1   GCAGGTTTGCCTATTGCTATTACTACTGTTGCTAAGGCATTACGAAATAAACCTTCCGAC
             1030       1040       1050       1060       1070       1080
             1090       1100       1110       1120       1130       1140
Vat    ATTTGGAATGATGCCTTAGATCAGCTTAAAACTGTTGATGTGGGTATGGCAAACATTGGA
       ::::::::::::::::::::::::::::: ::::::::::::::::::::::::::::::
Vat1   ATTTGGAATGATGCCTTAGATCAGCTTAAAAGTGTTGATGTGGGTATGGCAAACATTGGA
             1090       1100       1110       1120       1130       1140
             1150       1160       1170       1180       1190       1200
Vat    GAAATGGAAAGAAAGTGTATTTGTCACTAAAACTGAGTTACGATTGCTTGGGATATGAA
       ::::::::::::::::::::::::::::::::::::::::::::::::::::::::::::
Vat1   GAAATGGAAAGAAAGTGTATTTGTCACTAAAACTGAGTTACGATTGCTTGGGATATGAA
             1150       1160       1170       1180       1190       1200
             1210       1220       1230       1240       1250       1260
Vat    GAGGTGAAGTTATTATTCTTGTTATGCAGCATGTTTCCAGAAGACTTTAGCATTGACGTG
       ::::::::::::::::::::::::::::::::::::::::::::::::::::::::::::
Vat1   GAGGTGAAGTTATTATTCTTGTTATGCAGCATGTTTCCAGAAGACTTTAGCATTGACGTG
             1210       1220       1230       1240       1250       1260
             1270       1280       1290       1300       1310       1320
Vat    GAAGGGTTGCATGTATATGCCATGGGCATGGGATTCTTACATGGTGTTGATACTGTGGTA
       ::::::::::::::::::::::::::::::::::::::::::::::::::::::::::::
Vat1   GAAGGGTTGCATGTATATGCCATGGGCATGGGATTCTTACATGGTGTTGATACTGTGGTA
             1270       1280       1290       1300       1310       1320
```

FIG. 2 (continued)

```
         1330      1340      1350      1360      1370      1380
Vat  AAAGGACGACGTAGGATAAAAAAATTGGTTGATGATCTTATATCTTCTTCTTTGCTTCAA
     ::::::::::::::::::::::::::::::::::::::::::::::::::::::::::::
Vat1 AAAGGACGACGTAGGATAAAAAAATTGGTTGATGATCTTATATCTTCTTCTTTGCTTCAA
         1330      1340      1350      1360      1370      1380
         1390      1400      1410      1420      1430      1440
Vat  CAATATTCTGAGTATGGGTGCAATTATGTGAAAATGCATGATATGGTTCGTGATGTAGCC
     ::::::::::::::::::::::::::::::::::::::::::::::::::::::::::::
Vat1 CAATATTCTGAGTATGGGTGCAATTATGTGAAAATGCATGATATGGTTCGTGATGTAGCC
         1390      1400      1410      1420      1430      1440
         1450      1460      1470      1480      1490      1500
Vat  CTATTAATTGCATCTAAGAATGAACACGTACGTACATTGAGCTATGTGAAAAGATCGAAT
     ::::::::::::::::::::::::::::::::::::::::::::::::::::::::::::
Vat1 CTATTAATTGCATCTAAGAATGAACACGTACGTACATTGAGCTATGTGAAAAGATCGAAT
         1450      1460      1470      1480      1490      1500
         1510      1520      1530      1540      1550      1560
Vat  GAAGAATGGGAAGAAGAGAAACTATTGGGTAATCATACCGCAGTGTTCATTGATGGTTTA
     ::::::::::::::::::::::::::::::::::::::::::: ::::::::::::::::
Vat1 GAAGAATGGGAAGAAGAGAAACTATTGGGTAATCATACTGCAGTGTTCATTGATGGTTTA
         1510      1520      1530      1540      1550      1560
         1570      1580      1590      1600      1610      1620
Vat  CATTATCCTCTCCCGAAGTTAACGTTACCCAAAGTTCAATTATTAAGGTTAGTTGCAAAA
     ::::::::::::::::::::::::::::::::::::::::::::::::::::::::: ::
Vat1 CATTATCCTCTCCCGAAGTTAACGTTACCCAAAGTTCAATTATTAAGGTTAGTTGCACAA
         1570      1580      1590      1600      1610      1620
         1630      1640      1650      1660      1670      1680
Vat  TATTGTTGGGAACATAATAAGCGTGTGTCGGTGGTAGAAACTTTTTTTGAAGAAATGAAA
     : ::::::::::::::::::::::::::::::::::::::::::::::::::::::::::
Vat1 GATTGTTGGGAACATAATAAGCGTGTGTCGGTGGTAGAAACTTTTTTTGAAGAAATGAAA
         1630      1640      1650      1660      1670      1680
         1690      1700      1710      1720      1730      1740
Vat  GAGCTCAAAGGTTTAGTAGTAGAAAACGTAAATATATCATTGATGCAACGACCATCTGAT
     :::::::::::::::::::: ::: ::::::::::::::::::::::::::: ::::::::
Vat1 GAGCTCAAAGGTTTAGTATTAGCAAACGTAAATATATCATTGATGCAACGAACATCTGAT
         1690      1700      1710      1720      1730      1740
         1750      1760      1770      1780      1790      1800
Vat  GTTTACTCCTTAGCAAACATCAGAGTATTACGTTTGGAAAGATGTCAATTATTAGGGAGC
     : ::::::::::::::::::::::::::::::::::::  :::: :: : ::::::::::
Vat1 CTTTACTCCTTAGCAAACATCAGAGTATTACGTTTGCAAAGCTGTAATTTATTAGGGAGC
         1750      1760      1770      1780      1790      1800
         1810      1820      1830      1840      1850      1860
Vat  ATAGATTGGATTGGTGAATTAAAAAAGCTTGAAATTCTTGATTTTAGTGAATCTAACATC
     :::::::::::::::::::::::::::::::::::::::::::::::: : :::::::::
Vat1 ATAGATTGGATTGGTGAATTAAAAAAGCTTGAAATTCTTGATTTTATAGGATCTAACATC
         1810      1820      1830      1840      1850      1860
         1870      1880      1890      1900      1910      1920
Vat  ACACAAATTCCTACAACCATGAGCCAATTGACACAGCTAAAAGTGTTGAATTTATCTTCT
     ::::::::::::::::::::::::::::::::::::::: :: :::::::: ::::::::
Vat1 ACACAAATTCCTACAACCATGAGCCAATTGACACAACTCAAAGTGTTAAATTTATCTTCT
         1870      1880      1890      1900      1910      1920
         1930      1940      1950      1960      1970      1980
Vat  TGTGAACAACTTGAGGTAATTCCACCAAATATTCTTTCAAAGTTGACAAAATTGGAAGAA
     ::: : :::::  :::::::::::::::::::::::::::::::::::::::::::::::
Vat1 TGTCATCAACTCAAGGTAATTCCACCAAATATTCTTTCAAAGTTGACAAAACTGGAAGAA
         1930      1940      1950      1960      1970      1980
```

FIG. 2 (continued)

```
            1990       2000       2010       2020       2030       2040
Vat    TTAGATCTGGAAACTTTTGATGGATGGGAAGGAGAAGAATGGTATGAAGGAAGGAAAAAT
       ::: :::::::::::::  ::::::::::::::::::::::::::::::::::::::::
Vat1   TTAAGTCTGGAAACTTTTGATAGATGGGAAGGAGAAGAATGGTATGAAGGAAGGAAAAAT
            1990       2000       2010       2020       2030       2040
            2050       2060       2070       2080       2090       2100
Vat    GCTAGCCTTTCTGAACTCAAGTGCTTGCGACACCTTTATGCTTTAAACTTAACCATTCAA
       ::::::::::::::::::::::::::::::::::: ::::::::::: ::::::::::::
Vat1   GCTAGCCTTTCTGAACTCAAGTGCTTGCGACATCTTTATGCTTTAAATTTAACCATTCAA
            2050       2060       2070       2080       2090       2100
            2110       2120       2130       2140       2150       2160
Vat    GATGAAGAAATTATGCCAGAAAACTTGTTCTTAGTTGGGAAGTTGAAGCTTCAAAAATTC
       :::::::::::::::::::: ::: ::::: ::::  :: :: :::::::::::::::::
Vat1   GATGAAGAAATTATGCCAAAAGATTTGTTTTTAGCTGAGGAGTTGAAGCTTCAAAAATTC
            2110       2120       2130       2140       2150       2160
            2170       2180       2190       2200       2210       2220
Vat    AACATTTGTATTGGTTGCGAAAGCAAATTAAAGTATACTTTTGCATACAAGAACAGAATC
       ::::::::::::::::::: : :::::::::::::::::::::::  : :: :::::::::
Vat1   AACATTTGTATTGGTTACCAAAGCAAATTAAAGTATACTTTTGGACCCACAAACAGAATC
            2170       2180       2190       2200       2210       2220
            2230       2240       2250       2260       2270       2280
Vat    AAAAACTTCATTGGAATCAAGATGGAATCAGGAAGGTGCTTGGATGATTGGATAAAAAAT
       :::::::::::: ::::::::::::::::::::::::::::::::: :::::::::::::
Vat1   AAAAACTTCATTGCAATCAAGATGGAATCAGGAAGGTGCTTGGATAATTGGATAAAAAAT
            2230       2240       2250       2260       2270       2280
            2290       2300       2310       2320       2330       2340
Vat    TTGTTAAAGAGGTCGGACAATGTGCTTTTGGAAGGATCAGTTTGTTCAAAGGTTCTCCAC
       :::::::::::::::::::::::::: :::::::::::: :::::::::::::::::::::
Vat1   TTGTTAAAGAGGTCGGACAATGTGTTTTTGGAAGGATCAATTTGTTCAAAGGTTCTCCAC
            2290       2300       2310       2320       2330       2340
            2350       2360       2370       2380       2390       2400
Vat    TCAGAATTGGTAGGTGCCAATAACTTCGTATCACTTCCTAATTTGGAGAAGTTGGAAATT
       ::::::::::::::::::: ::: ::::::::::::::::::::::::::::::::::::
Vat1   TCAGAATTGGTAGGTGCAAATGACTTCGTATCGCTTCCTAATTTGGAGAAGTTGGAAATT
            2350       2360       2370       2380       2390       2400
            2410       2420       2430       2440       2450       2460
Vat    GTGAATGCAAAGAGTTTGAAGATGATATGGAGCAATAACGTGCCAATTCTTAATTCCTTT
       ::::::::::::::::::::::::::::::::::::::::::::::::::::::::::::
Vat1   GTGAATGCAAAGAGTTTGAAGATGATATGGAGCAATAACGTGCCAATTCTTAATTCCTTT
            2410       2420       2430       2440       2450       2460
            2470       2480       2490       2500       2510       2520
Vat    TCCAAACTCGAGGAAATAAAAATTTATTCATGCAACAATCTTCAAAAGTATTATTTCCT
       ::::::::::::::::::::::::::::::::::::::::::::::::::::::::::::
Vat1   TCCAAACTCGAGGAAATAAAAATTTATTCATGCAACAATCTTCAAAAGTATTATTTCCT
            2470       2480       2490       2500       2510       2520
            2530       2540       2550       2560       2570       2580
Vat    CCAAATATGATGGACATTCTCACATGCCTTAAAGTCTTAGAGATCAAAAATTGTGATTTG
       ::::::::::::::::::::::::::::::::::::::::::::::::::::::::::::
Vat1   CCAAATATGATGGACATTCTCACATGCCTTAAAGTCTTAGAGATCAAAAATTGTGATTTG
            2530       2540       2550       2560       2570       2580
            2590       2600       2610       2620       2630       2640
Vat    TTGGAAGGGATATTTGAAGCGCAAGAGCCAATTAGTGTTGTTGAGAGCAATAATTTACCC
       ::::::::::::::::::::::::::::::::::::::::::::::::::::::::::::
Vat1   TTGGAAGGGATATTTGAAGCGCAAGAGCCAATTAGTGTTGTTGAGAGCAATAATTTACCC
            2590       2600       2610       2620       2630       2640
```

FIG. 2 (continued)

```
              2650       2660       2670       2680       2690       2700
Vat     ATTCTTAATTCCTTTTCCAAACTCGAGGAAATAAGAATTTGGTCATGCAACAATCTTCAA
        ::::::::::::::::::::::::::::::::::::::::::::::::::::::::::::
Vat1    ATTCTTAATTCCTTTTCCAAACTCGAGGAAATAAGAATTTGGTCATGCAACAATCTTCAA
              2650       2660       2670       2680       2690       2700
              2710       2720       2730       2740       2750       2760
Vat     AAAGTATTATTTCCTTCAAATATGATGGGCATTCTTCCATGCCTTAAAGTCTTAGATATT
        ::::::::::::::::::::::::::::::::::::::::::::::::::::::::::::
Vat1    AAAGTATTATTTCCTTCAAATATGATGGGCATTCTTCCATGCCTTAAAGTCTTAGATATT
              2710       2720       2730       2740       2750       2760
              2770       2780       2790       2800       2810       2820
Vat     AGAGGTTGTGAATTGTTGGAAGGGATATTTGAAGTGCAAGAGCCAATTAGTGTTGTTGAG
        ::::::::::::::::::::::::::::::::::::::::::::::::::::::::::::
Vat1    AGAGGTTGTGAATTGTTGGAAGGGATATTTGAAGTGCAAGAGCCAATTAGTGTTGTTGAG
              2770       2780       2790       2800       2810       2820
              2830       2840       2850       2860       2870       2880
Vat     AGCAATAGTGTACCCATTCTTAATTCCTTTTCCAAACTCGAGAAAATAAGAATTTGGTCA
        ::::::::::::::::::::::::::::::::::::::::::::::::::::::::::::
Vat1    AGCAATAGTGTACCCATTCTTAATTCCTTTTCCAAACTCGAGAAAATAAGAATTTGGTCA
              2830       2840       2850       2860       2870       2880
              2890       2900       2910       2920       2930       2940
Vat     TGCAACAATCTTCAAAAAATATTATTTCCTTCAAATATGATGGGCATTCTTACATGCCTT
        ::::::::::::::::::::::::::::::::::::::::::::::::::::::::::::
Vat1    TGCAACAATCTTCAAAAAATATTATTTCCTTCAAATATGATGGGCATTCTTACATGCCTT
              2890       2900       2910       2920       2930       2940
              2950       2960       2970       2980       2990       3000
Vat     AAAGTCTTAGAGATCAGAGATTGTGAATTGTTGGAAGGGATATTTGAAGTGCAAGAGCCA
        ::::::::::::::::::::::::::::::::::::::::::::::::::::::::::::
Vat1    AAAGTCTTAGAGATCAGAGATTGTGAATTGTTGGAAGGGATATTTGAAGTGCAAGAGCCA
              2950       2960       2970       2980       2990       3000
              3010       3020       3030       3040       3050       3060
Vat     ATTAGTGTTGTTGAGAGCAATAATTTACCCATTCTTAATTCCTTTTCCAAACTCGAGGAA
        :::::::::::::::
Vat1    ATTAGTGTTGTTGA----------------------------------------------
              3010
              3070       3080       3090       3100       3110       3120
Vat     ATAAGAATTGGGTCATGCAACAATCTTCAAAAGTATTATTTCCTCCAAATATGATGGGC

Vat1    ------------------------------------------------------------

3130       3140       3150       3160       3170       3180
Vat     ATTCTTACATGCCTTAAAGTCTTAGAGATTAGACATTGTAATTTGTTGGAAGGGATATTT

Vat1    ------------------------------------------------------------

3190       3200       3210       3220       3230       3240
Vat     GAAGTGCAAGAGCCAATTAGTATTGTTGAAGCGAGTCCTATCTTGCTCCAAAATTTATCT
                                           :::::::::::::  :::::::::: :
Vat1    -------------------------------AGCGAGTCCTATCGTGCTCCAAAATTAATT
                                               3020       3030       3040
              3250       3260       3270       3280       3290       3300
Vat     TCGTTGATGTTATGTAATCTTCCAAACCTTGAGTACGTGTGGAGCAAAAATCCTTATGAA
        ::::        ::::  ::::::::::::::::::::::::::::::::::::  :::
Vat1    AGGTTGGAATTATATAATCTTCCAAACCTTGAGTACGTGTGGAGCAAAAATCCTTGTGAG
              3050       3060       3070       3080       3090       3100
```

FIG. 2 (continued)

```
              3310       3320       3330       3340       3350       3360
Vat   CTTCTGAGTTTGGAAAATATAAAAAGTTTGACCATTGATAAATGTCCAAGACTTAGAAGA
      ::::::::::::::::::::::::::::::::::::::::   :::::::::::::::::::
Vat1  CTTCTGAGTTTGGAAAATATAAAAAGTTTGACCATTGAGGAATGTCCAAGACTTAGAAGA
      3110       3120       3130       3140       3150       3160
              3370       3380       3390       3400       3410       3420
Vat   GAATACTCAGTCAAAATTCTAAAGCAACTTGAAGATGTAAGCATAGATATCAAACAATTG
      :::::::::::::::::: : :::: :::: :: :::::::::::::::::::::::::::
Vat1  GAATACTCAGTCAAAATTTTCAAGCCACTTCAATATGTAAGCATAGATATCAAACAATTG
      3170       3180       3190       3200       3210       3220
              3430       3440       3450       3460       3470       3480
Vat   ATGAAGGTTATTGAGAAGGAAAAGTCAGCACATCATAATATGTTGGAATCAAAGCAATGG
      :::::::::::::::::::::::::::::::: ::::::::::::::::::::::::::::
Vat1  ATGAAGGTTATTGAGAAGGAAAAGTCAGCAGATCATAATATGTTGGAATCAAAGCAATGG
      3230       3240       3250       3260       3270       3280
              3490       3500       3510       3520       3530       3540
Vat   GAGACTTCATCTTCTTCTAAGGATGGGGTTCTACGGCTGGGAGATGGTTCTAAGTTGTTT
      :::::::: ::::::::::::::::::::::::::::::::::::::::::::::::::::
Vat1  GAGACTTCTTCTTCTTCTAAGGATGGGGTTCTACGGCTGGGAGATGGTTCTAAGTTGTTT
      3290       3300       3310       3320       3330       3340
              3550       3560       3570       3580       3590       3600
Vat   CCAAATCTTAAAAGTTTGAAGCTATATGGTTTTGTTGATTATAACTCAACCCATTTACCA
      ::::::::::::::::::::::::::::::::::::::::::::::::::::::::::::
Vat1  CCAAATCTTAAAAGTTTGAAGCTATATGGTTTTGTTGATTATAACTCAACCCATTTACCA
      3350       3360       3370       3380       3390       3400
              3610       3620       3630       3640       3650       3660
Vat   ATGGAAATGTTGCAAATCTTATTCCAACTTGTAGTCTTTGAATTGGAAGGAGCATTTCTT
      :::::::::::::::::::::::::::::   :  :::::::::::::::::::::::: ::
Vat1  ATGGAAATGTTGCAAATCTTATTCCAACTTAAACACTTTGAATTGGAAGGAGCATTTATT
      3410       3420       3430       3440       3450       3460
              3670       3680       3690       3700       3710       3720
Vat   GAAGAAATTTTCCCCAGCAACATACTGATTCCAAGCTATATGGTTTTAAGAAGATTAGCT
      ::::::::::::::::::: :::::::::::: ::::: :::::: ::  :: ::  :::
Vat1  GAAGAAATTTTCCCCAGCAATATACTGATTTCAAGCTCTATGGATTTACAGAGTTTGGCT
      3470       3480       3490       3500       3510       3520
              3730       3740       3750       3760       3770       3780
Vat   CTATCTAAACTACCCAAGCTTAAGCATTTGTGGAGTGAAGAATGCTCACAAAACAATATC
      :::: :::::::::::::::::::::::::::::::::::::::::::::: ::::::::
Vat1  CTATATAAACTACCCAAGCTTAAGCATTTGTGGAGTGAAGAATGCTCACGAAACAATATC
      3530       3540       3550       3560       3570       3580
              3790       3800       3810       3820       3830       3840
Vat   ACCTCAGTTCTTCAACATTTGATTTCTCTAAGAATTTCAGAATGTGGAAGATTGAGTAGT
      :::::::::::::::::::::::: :::::::::::::::: ::::::::::::::::::
Vat1  ACCTCAGTTCTTCAACATTTGATTTTTCTAAGAATTTCAGATTGTGGAAGATTGAGTAGT
      3590       3600       3610       3620       3630       3640
                       3850       3860       3870       3880       3890
Vat   TTAC------TGTCGTCAATAGTGTGTTTTACAAACTTGAAACATCTTCGGGTTTATAAA
      :::       ::::  :::  :::::::::::::::::::::    :::  :::::::::
Vat1  TTAACTTTAGTGTCATCATTAGTGTGTTTTACAAACTTGAAAAGTCTTGCGGTTTATAAA
      3650       3660       3670       3680       3690       3700
              3900       3910       3920       3930       3940       3950
Vat   TGTGATGGACTAACCCATTTGCTGAATCCTTCGGTGGCTACAACGCTTGTGCAACTTGAG
      ::::::  ::::::::::::::::::::::::: ::::::::::::::::::::::::: :
Vat1  TGTGATAGACTAACCCATTTGCTGAATCCTTCGATGGCTACAACGCTTGTGCAACTTCAA
      3710       3720       3730       3740       3750       3760
```

FIG. 2 (continued)

```
              3960       3970       3980       3990       4000       4010
Vat   TCTTTGACAATAGAAGAATGCAAAAGGATGAGTAGTGTAATTGAGGGAGGATCAACCGAA
      :::::::: ::::::::::::: ::::: ::::::::::: ::::::::::::::::
Vat1  GATTTGACAATAAAAGAATGCAAAAGAATGAGAAGTGTAATTGAGGAAGGATCAACCGAA
              3770       3780       3790       3800       3810       3820
              4020       4030       4040       4050       4060       4070
Vat   GAAGATGGAAATGATGAAATGGTTGTATTCAACAACCTACAACATTTATACATTTTAAT
      :::::::::::::::::::::::::::::::::::::::::: :::::::::::::::::
Vat1  GAAGATGGAAATGATGAAATGGTTGTATTCAACAACCTACGACATTTATACATTTTAAT
              3830       3840       3850       3860       3870       3880
              4080       4090       4100       4110       4120       4130
Vat   TGTTCCAACCTAACAAGCTTTTATTGTGGGAGATGCATTATTAAATTTCCATGTTTGAGG
      ::::::::::::::::::::::::::::::::::::::  ::::::: :::::::::
Vat1  TGTTCCAACCTAACAAGCTTTTATTGTGGGAGATGCATCGTTAAATTCCCATGTTTGGAA
              3890       3900       3910       3920       3930       3940
              4140       4150       4160       4170       4180       4190
Vat   CAAGTAGACATTTGGAACTGTTCTGAAATGAAGGTCTTTTCGCTTGGAATTGTAAGCACA
      ::::  ::::  ::  :::  ::::::::::::::::::: :::::::::::::::::::
Vat1  AGAGTATTCATTCAAAATTGTCCTGAAATGAAGGTCTTTTCACTTGGAATTGTAAGCACG
              3950       3960       3970       3980       3990       4000
              4200       4210       4220       4230       4240       4250
Vat   CCTCGATTGAAATATGAAAATTTTTCTTTAAAGAATGATTACGATGATGAACGGTGTCAT
      :::::  :::::::::::::::  :::::: :::::::::::::::::::: ::::::::::
Vat1  CCTCGTTTGAAATATGAAAAGTTTACTTTAATGAATGATTACGATGATAAATGGTGTCAT
              4010       4020       4030       4040       4050       4060
              4260       4270       4280       4290       4300       4310
Vat   CCAAAATATCCCAAAGATATGTTGGTGGAAGATATGAATGTCATCACCAGAGAATATTGG
      :   ::::::::::::: ::::::::::::::::::::::::::::::::::::::::::
Vat1  CTGAAATATCCCAAATATATGTTGGTGGAAGATATGAATGTCATCACCAGAGAATATTGG
              4070       4080       4090       4100       4110       4120
              4320       4330       4340       4350       4360       4370
Vat   GAGGATAATGTTGATACCGGAATTCCAAATTTATTTGCCGAACAGAGTTTGGAGGAAAAC
      ::::::::::::::::::::::::::::::::::::::::::::::::::::::::::::
Vat1  GAGGATAATGTTGATACCGGAATTCCAAATTTATTTGCCGAACAGAGTTTGGAGGAAAAC
              4130       4140       4150       4160       4170       4180
              4380       4390       4400       4410       4420
Vat   CGATCTGAAAATTCTTCTTCTTCGAAGAATAATGTTGAGAAAGAATAA
      :::::::::::::::::::::::: :::::::::::::::::::::::
Vat1  CGATCTGAAAATTCTTCTTCTTCAAAGAATAATGTTGAGAAAGAATAA
              4190       4200       4210       4220       4230
```

FIG. 2 (end)

```
           10        20        30        40        50        60
Vat    MDILISVTAKIAEYTVEPVGRQLGYVFFIRSNFQKLKTQVEKLKITRESVQHKIHSARRN
       ::::::::::::::::::::::::::::::::::::::::::::::::::::::::::::
Vat1   MDILISVTAKIAEYTVEPVGRQLGYVFFIRSNFQKLKTQVEKLKITRESVQHKIHSARRN
           10        20        30        40        50        60
           70        80        90       100       110       120
Vat    AEDIKPAVEEWLKKVDDFVRESDEILANEGGHGGLCSTYLVQRHKLSRKASKMVDEVLEM
       ::::::::::::::::::::::::::::::::::::::::::::::::::::::::::::
Vat1   AEDIKPAVEEWLKKVDDFVRESDEILANEGGHGGLCSTYLVQRHKLSRKASKMVDEVLEM
           70        80        90       100       110       120
          130       140       150       160       170       180
Vat    KNEGESFDMVSYKSVIPSVDCSLPKVPDFLDFESRKSIMEQIMDALSDGNVHRIGVYGMG
       :::::::::::::::::::::::::::::::.::::::::::::::::::::::::::::
Vat1   KNEGESFDMVSYKSVIPSVDCSLPKVPDFIDFESRKSIMEQIMDALSDGNVHRIGVYGMG
          130       140       150       160       170       180
          190       200       210       220       230       240
Vat    GVGKTMLVKDILRKIVESKKPFDEVVTSTISQTPDFRSIQGQLADKLGLKFEQETIEGRA
       ::::::::::::::::::::::::::::::::::::::::::::::::::::::::::::
Vat1   GVGKTMLVKDILRKIVESKKPFDEVVTSTISQTPDFRSIQGQLADKLGLKFEQETIEGRA
          190       200       210       220       230       240
          250       260       270       280       290       300
Vat    TILRKRLKMERSILVVLDDVWEYIDLETIGIPSVEDHTGCKILFTTRIKHLISNQMCANK
       ::::::::::::::::::::::::::::::::::::::::::::::::::::::::::::
Vat1   TILRKRLKMERSILVVLDDVWEYIDLETIGIPSVEDHTGCKILFTTRIKHLISNQMCANK
          250       260       270       280       290       300
          310       320       330       340       350       360
Vat    IFEIKVLGKDESWNLFKAMAGDIVDASDLKPIAIRIVRECAGLPIAITTVAKALRNKPSD
       ::::::::::::::::::::::::::::::::::::::::::::::::::::::::::::
Vat1   IFEIKVLGKDESWNLFKAMAGDIVDASDLKPIAIRIVRECAGLPIAITTVAKALRNKPSD
          310       320       330       340       350       360
          370       380       390       400       410       420
Vat    IWNDALDQLKTVDVGMANIGEMEKKVYLSLKLSYDCLGYEEVKLLFLLCSMFPEDFSIDV
       :::::::::::.::::::::::::::::::::::::::::::::::::::::::::::::
Vat1   IWNDALDQLKSVDVGMANIGEMEKKVYLSLKLSYDCLGYEEVKLLFLLCSMFPEDFSIDV
          370       380       390       400       410       420
          430       440       450       460       470       480
Vat    EGLHVYAMGMGFLHGVDTVVKGRRRIKKLVDDLISSSLLQQYSEYGCNYVKMHDMVRDVA
       ::::::::::::::::::::::::::::::::::::::::::::::::::::::::::::
Vat1   EGLHVYAMGMGFLHGVDTVVKGRRRIKKLVDDLISSSLLQQYSEYGCNYVKMHDMVRDVA
          430       440       450       460       470       480
          490       500       510       520       530       540
Vat    LLIASKNEHVRTLSYVKRSNEEWEEEKLLGNHTAVFIDGLHYPLPKLTLPKVQLLRLVAK
       :::::::::::::::::::::::::::::::::::::::::::::::::::::::::::.
Vat1   LLIASKNEHVRTLSYVKRSNEEWEEEKLLGNHTAVFIDGLHYPLPKLTLPKVQLLRLVAQ
          490       500       510       520       530       540
          550       560       570       580       590       600
Vat    YCWEHNKRVSVVETFFEEMKELKGLVVENVNISLMQRPSDVYSLANIRVLRLERCQLLGS
       .::::::::::::::::::::::::::::. :::::::::: ..:::::::::. :::::
Vat1   DCWEHNKRVSVVETFFEEMKELKGLVLANVNISLMQRTSDLYSLANIRVLRLQSCNLLGS
          550       560       570       580       590       600
          610       620       630       640       650       660
Vat    IDWIGELKKLEILDFSESNITQIPTTMSQLTQLKVLNLSSCEQLEVIPPNILSKLTKLEE
       ::::::::::::::::::.:::::::::::::::::::::::.::.::::::::::::::
Vat1   IDWIGELKKLEILDFIGSNITQIPTTMSQLTQLKVLNLSSCHQLKVIPPNILSKLTKLEE
          610       620       630       640       650       660
```

FIG. 3

```
              670        680        690        700        710        720
Vat   LDLETFDGWEGEEWYEGRKNASLSELKCLRHLYALNLTIQDEEIMPENLFLVGKLKLQKF
      :.::::: :::::::::::::::::::::::::::::::::::::..:::  ..:::::
Vat1  LSLETFDRWEGEEWYEGRKNASLSELKCLRHLYALNLTIQDEEIMPKDLFLAEELKLQKF
              670        680        690        700        710        720
              730        740        750        760        770        780
Vat   NICIGCESKLKYTFAYKNRIKNFIGIKMESGRCLDDWIKNLLKRSDNVLLEGSVCSKVLH
      ::::: .:::::::.:: :::::::::.::::::::.::::::::::: :::: :::::
Vat1  NICIGYQSKLKYTFGPTNRIKNFIAIKMESGRCLDNWIKNLLKRSDNVFLEGSICSKVLH
              730        740        750        760        770        780
              790        800        810        820        830        840
Vat   SELVGANNFVSLPNLEKLEIVNAKSLKMIWSNNVPILNSFSKLEEIKIYSCNNLQKVLFP
      :::::::.::::::::::::::::::::::::::::::::::::::::::::::::::::
Vat1  SELVGANDFVSLPNLEKLEIVNAKSLKMIWSNNVPILNSFSKLEEIKIYSCNNLQKVLFP
              790        800        810        820        830        840
              850        860        870        880        890        900
Vat   PNMMDILTCLKVLEIKNCDLLEGIFEAQEPISVVESNNLPILNSFSKLEEIRIWSCNNLQ
      ::::::::::::::::::::::::::::::::::::::::::::::::::::::::::::
Vat1  PNMMDILTCLKVLEIKNCDLLEGIFEAQEPISVVESNNLPILNSFSKLEEIRIWSCNNLQ
              850        860        870        880        890        900
              910        920        930        940        950        960
Vat   KVLFPSNMMGILPCLKVLDIRGCELLEGIFEVQEPISVVESNSVPILNSFSKLEKIRIWS
      ::::::::::::::::::::::::::::::::::::::::::::::::::::::::::::
Vat1  KVLFPSNMMGILPCLKVLDIRGCELLEGIFEVQEPISVVESNSVPILNSFSKLEKIRIWS
              910        920        930        940        950        960
              970        980        990       1000       1010       1020
Vat   CNNLQKILFPSNMMGILTCLKVLEIRDCELLEGIFEVQEPISVVESNNLPILNSFSKLEE
      ::::::::::::::::::::::::::::::::::::::::::::::
Vat1  CNNLQKILFPSNMMGILTCLKVLEIRDCELLEGIFEVQEPISVVE---------------
              970        980        990       1000
             1030       1040       1050       1060       1070       1080
Vat   IRIGSCNNLQKVLFPPNMMGILTCLKVLEIRHCNLLEGIFEVQEPISIVEASPILLQNLS
                                                         :::::.::::
Vat1  --------------------------------------------------ASPIVLQNLI
                                                              1010
             1090       1100       1110       1120       1130       1140
Vat   SLMLCNLPNLEYVWSKNPYELLSLENIKSLTIDKCPRLRREYSVKILKQLEDVSIDIKQL
      : : :::::::::::::: :::::::::::::..:::::::::::.: :. ::::::::
Vat1  RLELYNLPNLEYVWSKNPCELLSLENIKSLTIEECPRLRREYSVKIFKPLQYVSIDIKQL
             1020       1030       1040       1050       1060       1070
             1150       1160       1170       1180       1190       1200
Vat   MKVIEKEKSAHHNMLESKQWETSSSSKDGVLRLGDGSKLFPNLKSLKLYGFVDYNSTHLP
      :::::::::::.::::::::::::::::::::::::::::::::::::::::::::::::
Vat1  MKVIEKEKSADHNMLESKQWETSSSSKDGVLRLGDGSKLFPNLKSLKLYGFVDYNSTHLP
             1080       1090       1100       1110       1120       1130
             1210       1220       1230       1240       1250       1260
Vat   MEMLQILFQLVVFELEGAFLEEIFPSNILIPSYMVLRRLALSKLPKLKHLWSEECSQNNI
      ::::::::::: :::::::.::::::::::: : :. ::: :::::::::::::::.:::
Vat1  MEMLQILFQLKHFELEGAFIEEIFPSNILISSSMDLQSLALYKLPKLKHLWSEECSRNNI
             1140       1150       1160       1170       1180       1190
             1270       1280       1290       1300       1310
Vat   TSVLQHLISLRISECGRLSSL--LSSIVCFTNLKHLRVYKCDGLTHLLNPSVATTLVQLE
      :::::::: :.::::::::::    :::.:::::::::.::::.::::::::::::::::.
Vat1  TSVLQHLIFLRISDCGRLSSLTLVSSLVCFTNLKSLAVYKCDRLTHLLNPSMATTLVQLQ
             1200       1210       1220       1230       1240       1250
```

FIG. 3 (continued)

```
         1320      1330      1340      1350      1360      1370
Vat    SLTIEECKRMSSVIEGGSTEEDGNDEMVVFNNLQHLYIFNCSNLTSFYCGRCIIKFPCLR
       .:::.::::: :::: :::::::::::::::.:::::::::::::::::::.:::::.
Vat1   DLTIKECKRMRSVIEEGSTEEDGNDEMVVFNNLRHLYIFNCSNLTSFYCGRCIVKFPCLE
         1260      1270      1280      1290      1300      1310

1380      1390      1400      1410      1420      1430
Vat    QVDIWNCSEMKVFSLGIVSTPRLKYENFSLKNDYDDERCHPKYPKDMLVEDMNVITREYW
       .: : :: ::::::::::::::::::::.:. :::::. :: :::: :::::::::::::
Vat1   RVFIQNCPEMKVFSLGIVSTPRLKYEKFTLMNDYDDKWCHLKYPKYMLVEDMNVITREYW
         1320      1330      1340      1350      1360      1370

1440      1450      1460      1470
Vat    EDNVDTGIPNLFAEQSLEENRSENSSSSKNNVEKE
       :::::::::::::::::::::::::::::::::::
Vat1   EDNVDTGIPNLFAEQSLEENRSENSSSSKNNVEKE
         1380      1390      1400      1410
```

FIG. 3 (end)

GENE RESISTANT TO *APHIS GOSSYPII*

CROSS REFERENCE TO RELATED APPLICATIONS

This application is a national stage application filed under 35 U.S.C. 371 of International Application No. PCT/FR2004/00050, filed Jan. 13, 2004, which claims priority from French patent application 03 00287, filed Jan. 13, 2003.

FIELD AND BACKGROUND OF THE INVENTION

The present invention relates to novel means for combating insect pests, and in particular for combating aphids.

Insect pests constitute one of the main preoccupations in agriculture. Besides the damage produced by the insects themselves, attack by these insects very often promotes transmission and infection of the plants with bacterial, viral or fungal diseases.

Among pests, aphids (also called greenfly) are the most common. There are more than 4000 species of them, the most widespread of which are *Myzus persicae* and *Aphis gossypii*.

Each species has a specific life cycle and a set of preferred hosts. Aphids are extremely dynamic organisms, which adapt rapidly to environmental conditions. This rapid adaptation is essentially due to the various reproductive strategies developed by aphids. Depending on the climatic conditions, aphids reproduce sexually or asexually and are oviparous or viviparous. They may or may not be winged, thus facilitating their passage from one plant to another. Due to this great ability to adapt and to reproduce, complete infestation of a crop in the open field and a fortiori in a greenhouse is extremely rapid. A single individual gives birth to between 40 and 100 larvae.

The cotton or melon aphid *Aphis gossypii* is present in most regions of the world, with the exception of the most northern. It is capable of performing a complete developmental cycle and of reproducing in less than a week. Because of its abilities to adapt and to reproduce, a large number of generations can be produced in a season, whatever the climatic conditions thereof. The melon aphid has a broad spectrum of hosts (approximately 700 cultivated or wild plants, including about 50 in France). Among these, the most sensitive are the Cucurbitaceae, including, for example, the melon, the courgette and the cucumber, the Malvaceae, such as the cotton plant or the hibiscus, and, to a lesser extent, the Solanaceae and the Rutaceae, such as citrus trees.

The melon aphid mainly colonizes the lower face of the leaves, the buds and the young shoots. By taking the nutritive elements thereof from the phloem, the aphid diverts the plant's resources and weakens it. The colonized tissues become chlorotic, the leaves roll up on themselves and the photosynthetic yield decreases. The aphid secretes a highly sugar-rich honeydew that serves as a substrate for saprophytic fungi, such as sooty mold, which deposits a black veil over the leaf, further reducing the photosynthetic capacities of the plant and causing a substantial commercial depreciation of the fruit and vegetables affected. In addition, the aphid is a vector for many viruses that it introduces directly into the phloem of the plant when it stabs the vessels.

Chemical control is currently still the most widespread technique. However, it has many drawbacks. The products used frequently have a broad spectrum of action and destroy beneficial insects at the same time as the aphids. The risks of polluting the environment are also considerable: aphicides are in fact among the most toxic products for humans, useful fauna and the environment (Recueil des effets non intentionnels des produits phytosanitaires [Collection of unintentional effects of plant protection products], Acta, 1998, p 256, Berger and Van Holst, 2001, Environ. Sci. Pollut. Res. Int., 8, 109-112). Moreover, the aphid *Aphis gossypii* has, in certain regions, developed resistances to the chemical compounds used, such as organophosphates, carbamates, pyrethroids and organochlorinated products (Larry et al., The Journal of Cotton Science, 5, 22-29, 2201; Delorme, Pesticide Science, 49, 90-96, 1997).

Biological control consists in using the natural predators and parasites of *Aphis gossypii*, for instance ladybugs, certain Hemiptera or pathogenic fungi. It can, however, only be used for greenhouse crops.

Another approach is based on the search for varieties that are naturally resistant to aphids, and on their use for varietal improvement and the creation of hybrids.

Aphid-resistant varieties have thus been found in particular in wheat, the apple tree, fodder pea, lettuce, tomato, etc.

In the melon (*Cucumis melo*), the existence of a dominant locus that confers resistance to the aphid *Aphis gossypii* has been discovered in melon lines originating from the Far East or from India. This locus, which was called Ag (for *Aphis gossypii* resistance) or Vat (for virus aphid transmission resistance), confers a double resistance phenotype: resistance to infestation of the plant with *Aphis gossypii* and resistance to transmission, by this aphid, of the viruses for which it is the vector (Kishaba et al., J. Econ. Entomol., 64, 935-937, 1971; Bohn et al., J. Amer. Soc. Hort. Science, 98, 37-40, 1973; Lecoq et al., Phytopathology, 69, 1223-1225, 1979; Pitrat and Lecoq, Phytopathology, 70, 958-961, 1980).

The resistance-promoting Vat locus has been introduced, by crossing, into various commercially available varieties of melon; however, the creation of aphid-resistant melon varieties by means of the usual techniques for varietal improvement remains lengthy and expensive.

SUMMARY OF THE INVENTION

It therefore appears to be desirable to precisely identify and to clone the Vat gene, in order in particular to make it possible:
- to transfer the resistance-promoting Vat allele, by transgenesis, to *Aphis gossypii*-sensitive melon varieties and also to other species sensitive to this aphid and for which no natural resistance has been detected, such as, for example, the courgette, the cucumber or the cotton plant; the resistance-promoting Vat gene allele can also be transferred into plant species sensitive to viral transmission by aphids, for instance the Solanaceae, in particular the tomato;
- to search for orthologues of the Vat gene in species other than the melon;
- to define novel markers that can be used in particular in the context of conventional techniques for varietal selection, in order to facilitate the identification of resistant varieties, and/or the monitoring of the introgression of the resistance characteristic in varieties of agronomic interest.

BRIEF DESCRIPTION OF THE DRAWING

FIG. 1 shows a sequence of a DNA fragment containing the Vat gene in which the 4 exons are double underlined and the 3 introns are single underlined (SEQ ID No. 1).

FIG. 2 shows the sequence alignment between the Vat cDNA (SEQ ID No. 2) and the Vat-like cCNA (SEQ ID No. 4).

FIG. 3 shows the alignment of the deduced Vat and Vat-like protein sequences (SEQ ID No. and SEQ ID No. 6).

DETAILED DESCRIPTION

Figure 4:
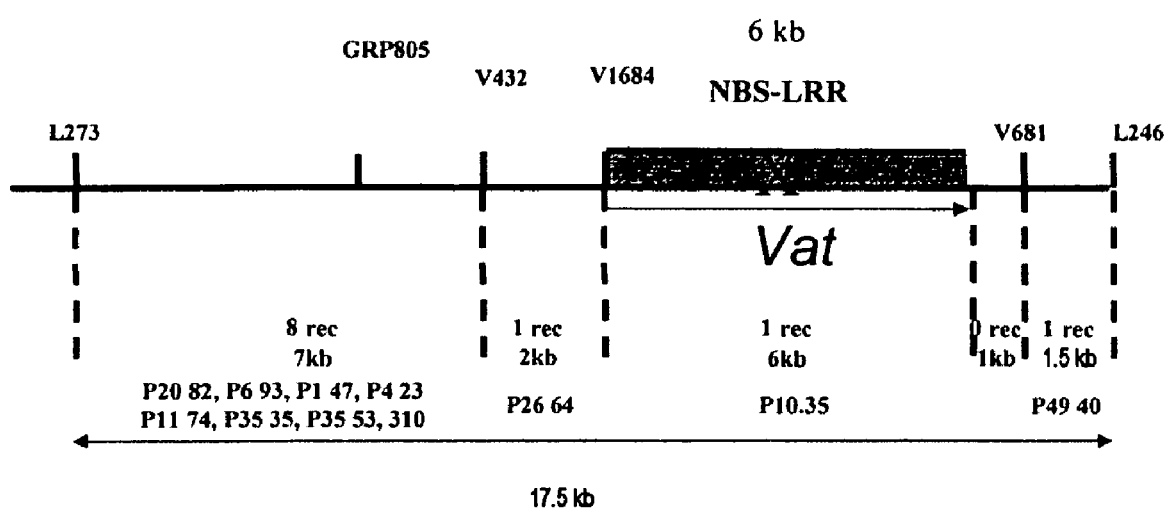
FIG. 4 illustrates the results of amplifying the DNA of backcross plants which exhibit recombination events in proximity to the Vat locus.

The Vat gene has been localized on melon chromosome V in the sub-telomeric position (Perin et al., Theor. Appl. Genet., 104, 1017-1034, 2002). Several sequences homologous to resistance genes have been mapped in this region (Klinger et al., J. Amer. Soc. Hort. Sci., 126, 56-63, 2001; Brotman et al., Theor. Apl. Genet., 104, 1055-1063, 2002), thus making it possible to imagine that the Vat gene belongs to the NSB-LRR superfamily, to which a large number of resistance genes that are currently being cloned belong.

This superfamily groups together genes containing a nucleotide-binding site (NBS) and leucine-rich repeats (LRRs). It has been observed that sequences homologous to NBS-LRRs are linked to the Vat locus (Klingler et al., J. Amer. Soc. Hort. Sci., 126, 56-63, 2001). Among these resistance gene homologues, NBS-2, NBS46-7, NBS5a and NBS5b have been localized, respectively, at 4.75, 7.5, 10 and 11 cM from Vat; however, none of them cosegregates with the Vat locus (Brotman et al., Theor. Appl. Genet., 104, 1055-1063, 2002).

The inventors have constructed a BAC (bacterial artificial chromosome) library from melon genomic DNA homozygotes for the Vat allele that promotes resistance to *Aphis gossypii* and resistance to viral transmission by this vector. They have, in parallel, defined markers that border the Vat locus more precisely than the markers known in the prior art. Screening the BAC library with these markers has made it possible to identify clones carrying the entire Vat locus.

The subcloning of one of these clones has made it possible to obtain a genomic DNA fragment of approximately 11000 bp containing the Vat gene. The sequence of this fragment is represented in FIG. 1 (the 4 exons are double underlined and the 3 introns are underlined), and also in the attached sequence listing under the number SEQ ID No.: 1. The corresponding cDNA sequence has also been obtained and the corresponding polypeptide sequence has been determined. These cDNA and polypeptide sequences are respectively represented in the attached sequence listing under the numbers SEQ ID No.: 2 and SEQ ID No.: 3.

A paralogue of the Vat gene, hereinafter referred to as Vat-like, has also been isolated from the BAC library. The sequence of this Vat-like gene is represented in the attached sequence listing under the number SEQ ID No.: 4. The cDNA sequence and the deduced polypeptide sequence are respectively represented in the appendix under the numbers SEQ ID No.: 5 and SEQ ID No.: 6.

FIG. 2 shows the sequence alignment between the Vat cDNA and the Vat-like cDNA. The Vat cDNA comprises 4422 bp whereas the Vat-like cDNA comprises only 4233 bp, due to a 195 bp deletion located between positions 3014 and 3210 of the Vat sequence and a 6 bp addition located between positions 3649 and 3656 of the Vat-like sequence. The Vat and Vat-like sequences exhibit 92.4% identity with one another.

FIG. 3 shows the alignment of the deduced Vat and Vat-like protein sequences which are made up of 1473 amino acids and 1410 amino acids, respectively. The Vat and Vat-like sequences exhibit approximately 90% identity with one another.

The Vat and Vat-like genes are genetically and physically linked (separated by 17 kb). Plants that are recombinant between Vat and Vat-like have been identified by genetic analysis. The plants carrying only the Vat-like gene are sensitive to colonization and to transmission of viruses by *A. gossypii*. Conversely, the plants carrying only the Vat gene are resistant to colonization and to transmission of viruses by *A. gossypii*. The Vat gene is therefore necessary and sufficient to confer the double phenotype described above.

A subject of the present invention is an isolated polynucleotide chosen from:

a) a polynucleotide encoding a polypeptide involved in resistance to the aphid *Aphis gossypii* and/or to viral transmission by said aphid, which polypeptide is at least 80%, preferably at least 90%, and most preferably at least 95% identical to the polypeptide SEQ ID No.: 3;

b) a polynucleotide complementary to the polynucleotide a);

c) a polynucleotide capable of hybridizing selectively, under stringent conditions, with the polynucleotide a); or the polynucleotide b).

Unless otherwise specified, the percentage sequence identities indicated here for the nucleotide or peptides sequences refer to the value obtained, over a window of comparison consisting of the entire reference sequence, with the BLAST software series (Altschul et al., Nucleic Acids Res., 25, 3389-3402, 1997) using the default parameters, over a window of comparison consisting of the entire reference sequence.

A polynucleotide "encoding" a given polypeptide is defined as any polynucleotide containing the genetic information allowing the synthesis of said polypeptide.

Thus, polynucleotides in accordance with the invention encoding a polypeptide involved in resistance to the aphid *Aphis gossypii* and/or to viral transmission by said aphid comprise in particular the polynucleotide of sequence SEQ ID No.: 1 and the polynucleotide of sequence SEQ ID No.: 2.

The present invention also includes any fragment of at least 10 bp, preferably at least 20 bp, and most preferably at least 50 bp, of a polynucleotide a) or b) above, or capable of hybridizing selectively, under stringent conditions, with a polynucleotide a) or b) above. Preferred fragments are those of any one of the polynucleotides of sequence SEQ ID No.: 1, SEQ ID No.: 2, SEQ ID No.: 4 or SEQ ID No.: 5 or those capable of hybridizing selectively, under stringent conditions, with one of these polynucleotides or the polynucleotide complementary thereto. Other preferred fragments are those of any one of the polynucleotides SEQ ID No.: 1 or SEQ ID No.: 2, which are not present in the polynucleotides SEQ ID No.: 4 or SEQ ID No.: 5, or fragments which are capable of hybridizing selectively with one of the polynucleotides SEQ ID No.: 1 or SEQ ID No.: 2, without hybridizing with the polynucleotides SEQ ID No.: 4 or SEQ ID No.: 5.

Stringent hybridization conditions, for a given nucleotide, can be identified by those skilled in the art according to the size and the base composition of the polynucleotide concerned, and also according to the composition of the hybridization mixture (in particular pH and ionic strength). Generally, stringent conditions, for a polynucleotide of given size and given sequence, are obtained by carrying out procedures at a temperature approximately 5° C. to 10° C. below the melting temperature (Tm) of the hybrid formed, in the same reaction mixture, by this polynucleotide and the polynucleotide complementary thereto.

A "polynucleotide capable of hybridizing selectively with a polynucleotide a) or b) in accordance with the invention" is here defined as any polynucleotide which, when it is hybridized under stringent conditions with a melon nucleic acid library (in particular a genomic DNA or cDNA library), produces a detectable hybridization signal (i.e. at least twice as great, preferably at least five times as great, as the background noise) with said polynucleotide, but produces no detectable signal with other sequences of said library, and in particular with sequences encoding other proteins of the NBS-LRR family.

A subject of the present invention is also polynucleotide probes or amplification primers obtained from polynucleotides a) or b) in accordance with the invention or fragments thereof.

The present invention also encompasses any polynucleotide encoding a polypeptide involved in resistance to the aphid *Aphis gossypii* and/or to viral transmission by said aphid, and which can be obtained from a plant genomic DNA or cDNA library by screening said library with probes or primers in accordance with the invention.

This includes in particular other alleles of the melon Vat gene, and in particular other alleles capable of conferring resistance to the aphid *Aphis gossypii* and/or to viral transmission by said aphid, and also orthologues of the Vat gene in plants other than the melon, in particular in other Cucurbitaceae, such as the courgette and the cucumber, and more generally in plants capable of being infected by *Aphis gossypii* (for example Malvaceae, such as the cotton plant) and/or sensitive to viral transmission by said aphid (for example Solanaceae, such as the tomato).

The present invention also encompasses genetic markers for detecting the presence or the absence, in a plant, and in particular in the melon, of an allele of the Vat gene that promotes resistance to colonization by the aphid *Aphis gossypii* and/or resistance to viral transmission by said aphid.

Genetic markers in accordance with the invention comprise in particular the following markers: L273, L246, V681, V1684, V432, GRP805, M8, marker E, marker D.

The markers E and D can more particularly be used to differentiate the Vat and Vat-like genes in PI161375.

These markers can be used especially in the Cucurbitaceae, in particular the melon. They can also be used in other plants, for example Malvaceae, such as the cotton plant or the hibiscus, or Solanaceae, such as the tomato.

The markers in accordance with the invention are respectively defined by the following primers:

L273:

F2-B2:
GGAGAGAGAATCCGGGACTAAGTGACT    (SEQ ID No.: 7)
F2-Br:
TAACCACCTTTTCCGATCAAATTTCGTAC  (SEQ ID No.: 8)

L246:

FR-B2 Eco:
ATTGATGAATCTACACTCCTCGATCTCTTC (SEQ ID No.: 9)
F2 Eco:
GAGTTCAATCCATTTCAATGATTTAAGATA (SEQ ID No.: 10)

V681:

V681:
GGAATCTTGTTGAGGCCGAGAGGG       (SEQ ID No.: 11)
V681R:
GTTGTATATGGCTTCCCTGTAGCC       (SEQ ID No.: 12)

V1684:

V588:
CAACAGGCTCAACAGTGTATTCGG       (SEQ ID No.: 13)
V551R:
GAAGAAGGTGACGAGAGAGATGCC       (SEQ ID No.: 14)

-continued

V432:

V432:
AACTTCTCCAACTCCCTCCACTGC       (SEQ ID No.: 15)
V432R:
TTAGAGTGGCAAAGGGAAGATGGG       (SEQ ID No.: 16)

GRP805:

GRP805:
ATCCCCTGTTTCCTTCAACAACCC       (SEQ ID No.: 17)
GRP805R:
AACCCCAAGAAGAAGAACAACCC        (SEQ ID No.: 18)

M8:

M8:
CCGACGCATCTCCCGACGCGTTGTTG     (SEQ ID No.: 19)
M8R:
TCGTGAAGGGTTTTGGAGAGTGAGAAA    (SEQ ID No.: 20)

Marker E:

LRR1:
CCTTAGAAGAAGATGAAGTCTCCC       (SEQ ID No.: 21)
LRR842R:
CTCCACTCAGAATTGGTAGGTGCC       (SEQ ID No.: 22)

Marker D:

LRR915:
AACAACTTAGAACCATCTCCCAGC       (SEQ ID No.: 23)
LRR1R:
GTTGTTGAGAGCAATAGTGTACCC       (SEQ ID No.: 24)

Other genetic markers for resistance to the aphid *A. gossypii* and/or to viral transmission by said aphid can also be defined based on the sequences SEQ ID No.: 1 and SEQ ID No.: 2, by comparing these sequences with their homologues obtained from plants sensitive to *A. gossypii* and/or to viral transmission by this aphid, in order to detect the polymorphisms that exist between these sequences, and to determine the form associated with resistance and the form associated with sensitivity.

These polymorphisms may be located in the coding regions of the Vat gene, and may result in modifications of the peptide sequence of the VAT protein. They may also be polymorphisms located in the 5' noncoding region or in the introns of the Vat gene, or polymorphisms located in the coding regions but that do not result in a sequence modification of the VAT protein.

When a polymorphism has thus been identified, it is possible to use it as a genetic marker for resistance or for sensitivity, and to define tools (nucleic acid probes, amplification primers, restriction enzymes) for distinguishing its various forms.

The present invention also encompasses the use of at least one polynucleotide or of at least one genetic marker in accordance with the invention, for detecting the presence, in a plant, of an allele of the Vat gene that promotes resistance to the aphid *Aphis gossypii* and/or resistance to viral transmission by said aphid.

A subject of the present invention is in particular a method for evaluating the resistance or the sensitivity of a plant to the aphid *Aphis gossypii* and/or to viral transmission by said aphid, characterized in that it comprises determining the allelic form of the Vat gene present in said plant.

A subject of the present invention is also oligonucleotide primers that can be used for carrying out the detection methods defined above.

In particular, a subject of the present invention is:
any pair of primers that makes it possible to amplify a region of the Vat gene comprising at least one polymorphism associated with resistance or sensitivity to *Aphis gossypii* and/or to viral transmission by said aphid;
any pair of primers that makes it possible to amplify one of the markers L273, L246, V681, V1684, V432, GRP805, M8, marker E or marker D, mentioned above.

A subject of the present invention is also kits for carrying out a method in accordance with the invention. These kits comprise at least one pair of primers in accordance with the invention, optionally combined with reagents for carrying out an amplification reaction, with means for detecting the amplification product, with one or more restriction enzymes, and/or with positive controls and/or negative controls for amplification.

A subject of the present invention is also:
an expression cassette comprising a polynucleotide in accordance with the invention, and in particular a polynucleotide encoding a polypeptide involved in resistance to the aphid *Aphis gossypii* and/or to viral transmission by said aphid, placed under the transcriptional control of a suitable promoter;
a recombinant vector resulting from the insertion, into a suitable host vector, of a polynucleotide or of an expression cassette in accordance with the invention.

The present invention also encompasses a method for producing a recombinant polypeptide, characterized in that it comprises transforming a prokaryotic or eukaryotic host cell with a polynucleotide in accordance with the invention encoding a polypeptide involved in resistance to the aphid *Aphis gossypii* and/or to viral transmission by said aphid, and recovering said polypeptide produced by said cell.

A subject of the present invention is also a polypeptide involved in resistance to the aphid *Aphis gossypii* and/or to viral transmission by said aphid, which polypeptide is at least 80%, preferably at least 90%, and most preferably at least 95%, identical to the polypeptide SEQ ID No.: 3, and also possesses fragments of at least 5, preferably at least 10, and most preferably at least 15, consecutive amino acids of said polypeptide.

The present invention also encompasses host cells that are genetically transformed with a polynucleotide or an expression cassette in accordance with the invention.

The host cells may be eukaryotic or prokaryotic cells. By way of examples, mention will be made of bacteria, in particular *E. coli* or *Agrobacterium*, yeast, for example *Saccharomyces*, animal cells or, preferably, plant cells.

The present invention also encompasses transgenic plants that are genetically transformed with a polynucleotide in accordance with the invention.

The conventional techniques for constructing recombinant vectors, for transforming host cells or organisms, and for producing recombinant proteins, can be used for implementing the present invention.

The choice of the host vector and of the sequences for regulating expression will be made according to the host cell or the host organism chosen and according to the application envisioned.

The genetic transformation of plants with a polynucleotide in accordance with the invention makes it possible to obtain transgenic plants resistant to the aphid *Aphis gossypii* and/or to viral transmission by said aphid.

A subject of the present invention is thus the use of a polynucleotide in accordance with the invention, for increasing the resistance of a plant to the aphid *Aphis gossypii*.

A subject of the present invention is thus more particularly a method for producing a transgenic plant resistant to the aphid *Aphis gossypii* and/or to viral transmission by said aphid, characterized in that it comprises genetically transforming said plant with a polynucleotide in accordance with the invention.

Said plant is advantageously chosen from species sensitive to *Aphis gossypii*, in particular from the Cucurbitaceae, such as the melon, the cucumber or the courgette, or the Malvaceae, such as the cotton plant or the hibiscus, or from species sensitive to the viruses transmitted by *A. gossypii*, in particular from the Solanaceae, such as the tomato or the capsicum.

In addition, overexpression of the Vat gene at a high level can result in constitutive resistance of the plant to more varied pathogenic agents in the melon or in other plant species (Cucurbitaceae, Solanaceae or Malvaceae). For example, this overexpression may allow the plant to recognize aphids that are phylogenetically distant from *Aphis gossypii* or may make it possible to confer weak constitutive resistance which will delay the infectious cycle of pathogenic agents in general. For this, it is possible to produce transgenic plants which express the Vat gene under the control of a strong promoter (35S) and which therefore will express it at a level higher than that which it has when it is under the control of its own promoter. However, the expression of the gene will necessarily have to be controlled at its minimum level in order to prevent harmful effects on the plant's biology (cell death, for example).

The genetic transformation of the plants can be carried out by conventional methods known, per se, to those skilled in the art.

By way of nonlimiting examples, for the transformation of Cucurbitaceae, and in particular of the melon, use may be made of the techniques described by Guis et al. (Biotechnology and Genetic Engineering Reviews, 15, 289-311, 1998; Scientia horticulturae, 84, 91-99, 2000). For the transformation of the cotton plant, use may be made of the techniques described by Pannetier et al. (Euphytica, 96, 163-166, 1997). For transformation of the tomato, it is possible to use the protocols described by Hamza and Chupeau (J. Exp. Bot., 44, 1837-1845, 1993).

Alternatively, plants having increased resistance to the aphid *Aphis gossypii* and/or to viral transmission by said aphid can be obtained by site-directed mutagenesis, in order to introduce into the allele of the Vat gene present in said plants the modifications necessary to confer this resistance.

Site-directed mutagenesis methods that can be used in the context of the present invention are known, per se, to those skilled in the art; they are, for example, described in the work by D. Tagu (published by INRA, 1999).

The invention also relates to the transformed plants obtained by means of a method of transgenesis or of site-directed mutagenesis in accordance with the invention, and also to the progeny of these plants. The invention also encompasses the products obtained from these plants, such as plant organs or tissues, cells, seeds, etc.

The present invention will be understood more clearly from the further description which follows, which refers to nonlimiting examples illustrating the definition of markers associated with the Vat gene, the cloning of this gene and the use of said gene for obtaining plants resistant to the aphid *A. gossypii* and/or to viral transmission.

EXAMPLE 1

Identification of the Vat Gene by Means of a Genetic Approach

Creation of the BAC Library

A BAC library of genomic DNA from melon (variety PI 161375 resistant to *Aphis gossypii* and to viral transmission by this aphid) representing approximately 29 genome equivalents was constructed. The first part of the BAC library contains 66048 clones (DNA digested with BamHI, HindIII) and the second part contains 56448 clones (DNA digested with EcoRI).

Screening of the BAC Library and Choice of the BAC Clone Carrying the Vat Locus

In order to identify the clone carrying the Vat gene, the library was screened using markers flanking the Vat locus. Several BAC clones covering the Vat locus were identified and organized. Novel markers were generated from these BAC clones. The BAC clone 3.18.9 carrying a 170 kb insertion comprising the Vat locus was chosen in order to identify the Vat gene, and sequenced. This clone comprises the markers L273 and L246 that frame the Vat locus. Ten recombinant plants out of 6000 plants derived from a backcross population [(Vedrantais (sensitive)×PI 161375 (resistant))×Vedrantais] were identified between the marker L273 and the Vat gene, whereas just one was identified between the marker L246 and the Vat gene.

The marker L273 is defined by the primers:

```
F2-B2:
GGAGAGAGAATCCGGGACTAAGTGACT     (SEQ ID No.: 7)
and

F2-Br:
TAACCACCTTTTCCGATCAAATTTCGTAC.  (SEQ ID No.: 8)
```

The amplification product obtained from genomic DNA of the variety Vedrantais (Vilmorin) (sensitive to *Aphis gossypii*) or of the variety PI 161375 (accession of Korean origin, multiplied by INRA) (resistant to *A. gossypii*) is 210 bp long. The amplification product has a BsiWI restriction site in the variety PI 161375, which results in two fragments of 181 bp and 29 bp being obtained. On the other hand, digestion with the BsrGI enzyme restricts the amplified Vedrantais material into three fragments: 153 bp, 28 bp and 29 bp, and the amplified PI 161375 material into two fragments of 182 bp and 28 bp.

The marker L246 is defined by the primers:

```
F2-B2 Eco:
ATTGATGAATCTACACTCCTCGATCTCTTC  (SEQ ID No.: 9)
and

F2 Eco:
GAGTTCAATCCATTTCAATGATTTAAGATA. (SEQ ID No.: 10)
```

The amplification product obtained from the genomic DNA of the variety Vedrantais or of the variety PI 161375 is 173 bp long. The amplification product of the variety PI 161375 has a restriction site for the EcoRV enzyme, which results in two fragments of 144 bp and 29 bp, respectively, being obtained.

Based on the BAC clone 3-18-9 possessing the two markers L273 and L246, oligonucleotides (Table 1) were designated in the region between these two markers in order to reduce the range thereof and to precisely delimit the Vat gene.

The marker V432 is defined by the primers:

```
V432:
AACTTCTCCAACTCCCTCCACTGC        (SEQ ID No.: 15)
and

V432R:
TTAGAGTGGCAAAGGGAAGATGGG.       (SEQ ID No.: 16)
```

The amplification product obtained from the genomic DNA of the variety Vedrantais or of the variety PI 161375 is 432 bp long. The amplification product of the variety PI 161375 has a restriction site for the HaeII enzyme, resulting in two fragments of 223 bp and 209 bp, respectively, being obtained.

This restriction site is absent from the variety Vedrantais.

The marker V681 is defined by the primers:

```
V681:
GGAATCTTGTTGAGGCCGAGAGGG        (SEQ ID No.: 11)
and

V681R:
GTTGTATATGGCTTCCCTGTAGCC.       (SEQ ID No.: 12)
```

The amplification product obtained from the genomic DNA of the variety Vedrantais or of the variety PI 161375 is 681 bp long. The amplification product of the variety PI 161375 has two restriction sites for the RsaI enzyme, resulting in three fragments of 435 bp, 221 bp and 25 bp, respectively, being obtained. These restriction fragments are absent from the variety Vedrantais.

The marker V1684 is defined by the primers:

```
V588:
CAACAGGCTCAACAGTGTATTCGG        (SEQ ID No.: 13)
and

V551R:
GAAGAAGGTGACGAGAGAGATGCC.       (SEQ ID No.: 14)
```

The fragment amplified in the variety Vedrantais measures approximately 1300 bp whereas, in the variety PI 161375, the amplified material measures 1684 bp. In this case, a size polymorphism is involved.

These markers, and also the markers D, E and M8 (cf. example 4 below) and the oligonucleotides defining them, are given in table 1 below:

TABLE 1

| Markers | Oligo-nucleotides | 5' oligonucleotide sequence 3' |
|---------|-------------------|--------------------------------|
| L273    | F2-B2             | GGAGAGAGAATCCGGGACTAAGTGACT (SEQ ID No.: 7) |
|         | F2-Br             | TAACCACCTTTTCCGATCAAATTTCGTAC (SEQ ID No.: 8) |

TABLE 1-continued

| Markers | Oligo-nucleotides | 5' oligonucleotide sequence 3' |
|---|---|---|
| L246 | F2-B2 Eco | ATTGATGAATCTACACTCCTCGATCTCTTC (SEQ ID No.: 9) |
|  | F2 Eco | GAGTTCAATCCATTTCAATGATTTAAGATA (SEQ ID No.: 10) |
| V681 | V681 | GGAATCTTGTTGAGGCCGAGAGGG (SEQ ID No.: 11) |
|  | V681R | GTTGTATATGGCTTCCCTGTAGCC (SEQ ID No.: 12) |
| V1684 | V588 | CAACAGGCTCAACAGTGTATTCGG (SEQ ID No.: 13) |
|  | V551R | GAAGAAGGTGACGAGAGAGATGCC (SEQ ID No.: 14) |
| V432 | V432 | AACTTCTCCAACTCCCTCCACTGC (SEQ ID No.: 15) |
|  | V432R | TTAGAGTGGCAAAGGGAAGATGGG (SEQ ID No.: 16) |
| GRP805 | GRP805 | ATCCCCTGTTTCCTTCAACAACCC (SEQ ID No.: 17) |
|  | GRP805R | AACCCCAAGAAGAAGAACAACCC (SEQ ID No.: 18) |
| M8 | M8 | CCGACGCATCTCCCGACGCGTTGTTG (SEQ ID No.: 19) |
|  | M85 | TCGTGAAGGGTTTTGGAGAGTGAGAAA (SEQ ID No.: 20) |
| Marker E | LRR1 | CCTTAGAAGAAGATGAAGTCTCCC (SEQ ID No.: 21) |
|  | LRR842R | CTCCACTCAGAATTGGTAGGTGCC (SEQ ID No.: 22) |
| Marker D | LRR915 | AACAACTTAGAACCATCTCCCAGC (SEQ ID No.: 23) |
|  | LRR1R | GTTGTTGAGAGCAATAGTGTACCC (SEQ ID No.: 24) |

Combinations of these oligonucleotides (table 2) were used to amplify the DNA of backcross plants derived from the cross [F1 (Vedrantais×PI 161375)×Vedrantais] and which exhibit recombination events in proximity to the Vat locus.

The results are illustrated in table 2 below, and FIG. 4.

TABLE 2

| | Marker | L273 | GRP805 | V432 | V1684 | Vat | V681 | L246 | M8 |
|---|---|---|---|---|---|---|---|---|---|
| | Oligo 1 | F2-B2 | GRP805 | V432 | V588 | Phenotype: resistance to colonization by A. gossypii and to viral transmission | V681 | F2-B2Eco | M8 |
| Amplification after digestion | Oligo 2 Digestion | F2-Br BsrGI | GRP805R SapI | V432R HaeII | V551R No digestion | | V681R RsaI | F2Eco EcoRV | M8R Aat II |
| | Vedrantais | 153 bp + 28 bp + 29 bp | 805 bp | 432 bp | Approx. 1300 bp | | 681 bp | 173 bp | 228 bp |
| | PI 161375 | 182 bp + 28 bp | 805 bp + 508 bp + 297 bp | 223 bp + 209 bp | 1684 bp | | 435 bp + 221 bp + 25 bp | 144 bp + 29 bp | 195 bp + 33 bp |
| Plant No. | P20 82 | − | + | + | + | R | + | + | + |
| | P6 93 | − | − | + | + | R | + | + | + |
| | P1 47 | − | − | + | + | R | + | + | + |
| | 848 | − | − | − | − | S | − | − | + |
| | P4 23 | + | − | − | − | S | − | − | − |
| | P11 74 | + | − | − | − | S | − | − | − |
| | P35 35 | + | − | − | − | S | − | − | − |
| | P35 53 | + | − | − | − | S | − | − | − |
| | 310 | + | + | − | − | S | − | − | − |
| | P26 64 | + | + | + | − | S | − | − | − |
| | P10 35 | + | + | + | + | S | − | − | − |
| | P49 40 | + | + | + | + | R | + | − | − |

These results show that:

Plant P26 64 exhibits a recombination event between the marker V432 and the Vat gene.

Plant P49 40 exhibits a recombination event between the marker L246 and the Vat gene.

Plant P10 35 exhibits a recombination event between the marker V1684 and the Vat gene. Since the marker V1684 includes the ATG of the Vat gene, this plant exhibits an intragenic recombination that destroys the function of the gene.

The marker V681 cosegregates with the Vat gene.

These data therefore make it possible to genetically identify the Vat gene.

EXAMPLE 2

Subcloning and Verification of the Sequence of the Vat Gene

The Vat gene was subcloned into the vector pGEM®3Zf+ (Promega). To do this, the BAC clone 3-18-9 was digested with the MscI restriction enzyme. Each fragment thus generated was ligated into the vector pGEM®3Zf+ (Promega) and then screened with the markers flanking the Vat gene or inside this gene.

A 18185 bp clone containing the Vat gene was identified (clone C7.1). Sequencing of the ends of the C7.1 clone, enzymatic restrictions, and sequencing of the Vat gene with the oligonucleotides in table 1 made it possible to verify that this was indeed the Vat gene. The sequence of a 11097 bp portion of this clone is represented in FIG. 1, and also in the attached sequence listing (SEQ ID No.: 1).

EXAMPLE 3

Obtaining the cDNA of the Vat Gene

The cDNA was obtained using the Marathon™ cDNA clone kit (Clontech). This cDNA is represented in the attached sequence listing under the number SEQ ID No.: 2.

The Vat gene contains 4 exons and 3 introns:

The first exon contains 2367 bp and extends from base 1 of the ATG initiation codon (corresponding to position 2344 according to SEQ ID No.: 1) to base 2367 (corresponding to position 4710 according to SEQ ID No.: 1).

The first intron extends from base 2368 to base 2921 (4711 to 5264 according to SEQ ID No.: 1).

The second exon extends from base 2922 to base 4055 (5265 to 6398 according to SEQ ID No.: 1).

The second intron extends from base 4056 to base 4876 (6399 to 7219 according to SEQ ID No.: 1).

The third exon extends from base 4877 to base 5734 (7220 to 8077 according to SEQ ID No.: 1).

The third intron extends from base 5735 to base 5833 (8078 to 8176 according to SEQ ID No.: 1).

The fourth exon extends from base 5834 to base 5896 (8177 to 8239 according to SEQ ID No.: 1).

EXAMPLE 4

Distinction Between the Vat Gene and the Vat-Like Gene

During the above screening, a clone carrying a homologue of the Vat gene (Vat-like) was identified (93.8% identity at the nucleic acid level and 89.9% at the protein level). The Vat-like sequence is represented in the attached sequence listing under the number SEQ ID No.: 4.

The Vat and Vat-like genes are genetically and physically linked since they are separated by 17 kb.

Two markers (marker D and marker E) make it possible to distinguish the Vat gene from the Vat-like gene in PI 161375.

The marker E is defined by the primers:

```
LRR1:
CCTTAGAAGAAGATGAAGTCTCCC      (SEQ ID No.: 21)
and

LRR842R:
CTCCACTCAGAATTGGTAGGTGCC.     (SEQ ID No.: 22)
```

This marker makes it possible to amplify, in PI 161375, a 1722 bp fragment corresponding to the Vat gene and a 1527 bp fragment corresponding to the Vat-like gene.

The amplification product obtained from the genomic DNA of the variety Vedrantais has a length of approximately 1.3 kb on an agarose gel.

The marker D is defined by the primers:

```
LRR915:
AACAACTTAGAACCATCTCCCAGC      (SEQ ID No.: 23)
and

LRR1R:
GTTGTTGAGAGCAATAGTGTACCC.     (SEQ ID No.: 24)
```

This marker makes it possible to amplify, in PI 161375, a 1549 bp fragment corresponding to the Vat gene and a 1372 bp fragment corresponding to the Vat-like gene. In Vedrantais, the marker makes it possible to amplify 4 DNA fragments of approximately 750 bp, 900 bp, 1100 bp and 1300 bp.

The markers L246 and M8 make it possible to characterize recombinants between the Vat gene and the Vat-like gene and to genetically distinguish these two genes.

The marker M8 is defined by the primers:

```
M8:
CCGACGCATCTCCCGACGCGTTGTTG    (SEQ ID No.: 19)
and

M8R:
TCGTGAAGGGTTTTGGAGAGTGAGAAA.  (SEQ ID No.: 20)
```

The amplification product obtained from the genomic DNA of the variety Vedrantais and PI 161375 is 228 bp long. The amplification product of the variety PI 161375 has a restriction site for the AatII enzyme, resulting in two fragments of 195 bp and 33 bp, respectively, being obtained.

In fact, plants that are recombinant between the Vat and Vat-like genes were identified within the [F1 (Vedrantais×PI 161375)×Vedrantais] backcross population. The plants carrying only the Vat-like gene are sensitive to *Aphis gossypii*; for example, plant 848 (table 2). Conversely, the plants that do not have the Vat-like gene are resistant to the *A. gossypii* aphids; for example, plant P4940 (table 2).

EXAMPLE 5

Construction of an Expression Vector Containing the Vat Gene

The genomic DNA of the Vat gene without its promoter is introduced into the binary vector pBin 61 (Bendahmane et al., The Plant Journal, 32, 195-204, 2002) containing in particular the NOS/NPTII chimeric gene, the kanamycin-resistance selection marker and the p35S promoter. The Vat gene in the sense orientation is introduced after the p35S promoter. The vector pBin61 is introduced into various strains of *Agrobacterium tumefaciens* (LBA4404, C58C1-pch32).

Alternatively, the complete genomic. DNA, comprising approximately 2.5 kb upstream and downstream of the Vat gene in order to be sure that the promoter and the regulatory sequences are present, is introduced, blunt ended, into the vector SLJ7292 (Jones et al., Transgenic Research, 1, 285-30 297, 1992) and pBin 19 (Bevan et al., Nucleic Acids Res., 12, 8711-8721, 1984). The binary vectors SLJ7292 and pBin 19 containing the Vat gene are introduced into various strains of *Agrobacterium tumefaciens* (LBA4404, C58C1-pch32, C58C1-pMP90 (Schweitzer et al., Plasmid, 4(2), 196-204, 1980; Goodner et al., Science, 294 (5550), 2323-2328, 2001), or C58pGV2260 (Deblaere et al., Nucleic Acids Res., 13, 4777-4788, 1985)).

Table 3 gives the constructs used according to the plants.

consisting of the MS medium supplemented with 1 μM of BAP and 0.3 μM of gibberellic acid (GA3) containing 100 mg·l$^{-1}$ of kanamycin and 225 mg·l$^{-1}$ of timentin, and solidified in 0.7 g·l$^{-1}$ of agar.

The buds are then placed in the rooting medium consisting of the MS medium without growth regulator and containing the same amounts of antibiotics and of agar.

As soon as the roots appear, the plantlets are acclimatized according to Guis et al. (Scientia Horticulturae, 69, 199-206, 1997) and transferred into a greenhouse according to the crop practices described by Ayub et al. (Nature Biotechnology, 14, 862-866, 1996).

The regenerated and rooted plants are analyzed by flow cytometry. Only the diploid plants are conserved and studied at the molecular level, by PCR, in order to verify the presence of the transgene.

To reveal the presence of the Vat gene, the pair of primers V1684 (SEQ ID Nos.: 13 and 14) located in the Vat promoter

TABLE 3

| Name | Promoter | Strain | Plasmid | Antibiotics | Plant |
|---|---|---|---|---|---|
| B1-1 | Vat | C58C1-pch32 | pBin 19 | Kanamycin (50 mg/l) | Melon, tomato |
| B1-3 | Vat | C58C1-pMP90 | pBin 19 | Kanamycin (50 mg/l) Gentamycin (20 mg/l) | Melon, tomato, cotton plant |
| pGV2260 Vat-Vat | Vat | C58C1-pGV2260 | pBin 19 | Kanamycin (50 mg/l) Carbencillin (50 mg/l) Rifampycin (50 mg/l) | Cotton plant |
| Vat 11.1 | Vat | LBA4404 | SLJ7292 | Tetracycline (5 mg/l) Streptomycin (300 mg/l) Rifampycin (50 mg/l) | Cotton plant |
| A6-3 | 35S | C58C1-pch32 | pBin 61 | Kanamycin (50 mg/l) Tetracycline (5 mg/l) | Melon, tomato, cotton plant |
| 35C | 35S-GUS | LBA4404 | pBI121 | Kanamycin (50 mg/l) | Melon |

EXAMPLE 6

Functional Validation in the Melon

Obtaining Genetically Transformed Melon Plants

The protocol followed is adapted from that of Guis et al. (Scientia Horticulturae, 84, 91-99, 2000).

Young leaf explants from sensitive melon of the variety Vedrantais (Vilmorin) are incubated with stirring in a suspension of *Agrobacterium tumefaciens* ($10^6$ to $10^8$ cells/ml), for 30 minutes. The transformations are carried out with the constructs described in example 5.

The explants potentially transformed are then transferred onto Whatman paper No. 1 for 10 minutes, and then incubated for 2 days at 27° C. in the dark on a coculture medium containing 1 μM of 6-benzylaminopurine (BAP), 1 μM of 6-(γ,γ-dimethylallylamino)purine (2IP), 0.2 mM of acetosyringone and 0.7 g·l$^{-1}$ of agar.

Regeneration of the foliar explants is obtained using the conditions described by Kathal et al. (Plant Cell Reports, 7, 449-451, 1988) with a few modifications. The foliar explants are transferred onto a regeneration medium composed of Murashige and Skoog (MS) medium (Physiol. Plant, 15, 473-497, 1962) supplemented with 1 μM of 6-benzylaminopurine (BAP), 1 μM of 6-(γ,γ-dimethylallylamino)purine (2iP), containing 100 mg·l$^{-1}$ of kanamycin and 225 mg·l$^{-1}$ of timentin, and solidified in 0.7 g·l$^{-1}$ of agar.

After 3 weeks of culture, the buds formed on the foliar explants are excised and incubated on a development medium and the pair of primers D (SEQ ID Nos.: 23 and 24) located in the middle of the Vat gene, as described in example 1, are used.

The PCR conditions are as follows:

Reaction mixture: water qs for 10 μl; 10× buffer 1 μl; dNTPs (4 mM) 0.6 μl; primer 1 (10 pM) 0.4 μl and primer 2 (10 pM) 0.4 μl; Takara Taq (5 U/μl) 0.08 μl; DNA 1.2 μl.

PCR conditions used:
 step 1: 2 min at 94° C.
 step 2, denaturation: 30 sec at 94° C.
 step 3, pairing: 45 sec at 60° C.
 step 4, elongation: 2 min at 72° C.
 step 5: 30 cycles of step 2 to step 4
 step 6: 10 min at 72° C.

b—To reveal the presence of the nptII gene for kanamycin resistance, the primers

```
Kana II:
5'-CCGGCTACCTGCCCATTC-3'    (SEQ ID No.: 25)
and

Kana III:
5'-GCGATAGAAGGCGATGCG-3'    (SEQ ID No.: 26)
``` are used according to the following conditions:

Reaction mixture: water qs for 10 μl; 10× buffer 1 μl; MgCl$_2$ (25 mM) 0.6 μl; dNTPs (4 mM) 0.2 μl; primer 1 (10 pM) 0.4 μl and primer 2 (10 pM) 0.4 μl; Promega Taq (5 U/μl) 0.04 μl; DNA 1.2 μl.

PCR conditions used:
- step 1: 2 min at 94° C.
- step 2, denaturation: 30 sec at 94° C.
- step 3, pairing: 1 min at 53° C.
- step 4, elongation: 1 min at 72° C.
- step 5: 30 cycles of step 2 to step 4
- step 6: 10 min at 72° C.

c—To verify that no amplification is due to the presence of residual bacteria in the tissues studied, the plants are also tested by PCR with the primers PicA+ (ATGCGCATGAGGCTCGTCTTCGAG; SEQ ID No.: 27) and PicA− (GACGCAACGCATCCTCGATCAGCT; SEQ ID No.: 28) that are specific for the chromosomal DNA of *A. tumefaciens* C58 strains; the reaction mixture and the PCR conditions being identical to those used with respect to the nptII gene.

Several series of transformations are carried out on the melon using the various constructs presented in example 5. The results of these transformations are summarized in table 4.

The in vitro plants derived from the genetic transformation experiments and from the in vitro germinations of the control plants were acclimatized in vivo for 10 days.

The test for resistance to colonization by *A. gossypii* is adapted from Pitrat and Lecoq (Phytopathology, 70, 958-961, 1980). The apterous adults are sampled with a fine brush and left without food for 1 hour in a Petri dish. Ten aphids are deposited onto two spread-out leaves from each plant to be tested. 48 hours after deposition, the number of aphids attached to the leaves is counted. At 48 hours, on the sensitive plants, the 10 aphids deposited are attached, whereas, on the resistant plants, only a few aphids (in general less than 5) remain on the leaves. Then, 7 days after infestation, the number of adult aphids and of larvae, and also their developmental stage, are observed. At the end of this period, on the sensitive plants, a new generation of aphids is produced (more than 100 aphids present on average) and many larvae are present (also more than 100). On the resistant plants, a few adults (in general less than 5) remain on the leaves and only a few

TABLE 4

| Genotype | Construct | Number of explants in culture | Number of diploid rooted plants | nptII | Vat marker V1684 | Vat marker D | PicA+/PicA− |
|---|---|---|---|---|---|---|---|
| Vedrantais | B1-1 | 100 | 2 | 2* | 2* | 2* | 0 |
| Vedrantais | B1-3 | 106 | 0 | 0 | 0 | 0 | 0 |
| Vedrantais | A6-3 | 112 | 0 | 0 | 0 | 0 | 0 |
| Vedrantais sensitive control | | | 0 | 0 | 0 | 0 | 0 |
| PI 161375 resistant control (Vat) | | | 0 | + | + | 0 | |

(Number of diploid plants positive in PCR)

*Two diploid Vedrantais melon plants (M1 and M4) obtained on the same explant using the construct B1-1 are identified as carrying the insert containing the nptII and Vat genes.

Two transformants carrying the Vat gene of the Vedrantais genotype were obtained by means of this first protocol.

The diploid rooted plants are propagated by taking cuttings, in vitro, on antibiotic-free medium, and then separated and acclimatized in a climate-controlled chamber (8 h night at 18° C.-16 h day at 24° C.) for 4 weeks before carrying out the biological tests.

Alternatively, the method for genetically transforming cotyledonous explants described in patent EP 0 412 912 (Limagrain) was also followed. Approximately 10 000 explants of the melon genotype C1Tz1 were inoculated with the C58C1pmp90 bacterium carrying the pvat-Vat gene construct. The plants regenerated and rooted on the medium provided with 100 mg·l$^{-1}$ of kanamycin were analyzed by PCR in order to verify the presence of the transgenes: nptII and Vat. The primers and PCR conditions used are those described above. 27 transformation events were identified as carrying the nptII gene.

In total, 2 transformants carrying the Vat gene of the Vedrantais genotype were obtained by means of the first protocol and 27 transformants were obtained by means of the second protocol.

Measurement of the Resistance to Colonization by *A. gossypii*

The Nm1 clone collected on melons (G. Labonne, INRA, Montpellier) and described as clone 13 (Lupoli et al., Entomologia Experimentalis et Applicata, 65, 291-300, 1992) is used. The *A. gossypii* aphids are bred on the Vedrantais melon in a culture chamber (16 hours day at 24° C. and 8 hours night at 18° C.).

relatively undeveloped larvae are present (less than 30). In each test, the sensitive control used is the Vedrantais cultivar and the resistant control is the Margot cultivar homozygote for the Vat locus.

The results obtained are given in tables 5 and 6:

TABLE 5

| | Observations at 48 h | | Observations at 7 days | |
|---|---|---|---|---|
| Plants | Number of plants tested | Number of resistant plants | Number of sensitive plants | Number of resistant plants | Number of sensitive plants |
| Sensitive control Vedrantais | 10 | 0 | 10 | 0 | 10 |
| Resistant control Margot | 10 | 10 | 0 | 10 | 0 |
| M1 | 8 | 7 | 1 | 7 | 1 |
| M4 | 12 | 12 | 0 | 12 | 0 |

TABLE 6

| | Average number of individuals at 48 h | | Average number of individuals at 7 days | |
|---|---|---|---|---|
| Plants | Adults | Larvae | Adults | Larvae |
| Sensitive control Vedrantais | 9.7 | 84 | 116 | 128 |

TABLE 6-continued

| Plants | Average number of individuals at 48 h | | Average number of individuals at 7 days | |
|---|---|---|---|---|
| | Adults | Larvae | Adults | Larvae |
| Resistant control Margot | 2.5 | 3.2 | 1.1 | 18 |
| M1 | 3.6 | 17* | 8.7* | 34* |
| M4 | 3.2 | 10 | 4.5 | 30 |

*estimated on the resistant plants

Alternatively, 3 aphids instead of 10 can be deposited on the leaves of each plant to be tested. The aphids may or may not be kept in a cage. Seven days after the depositing of the aphids, the number of adult aphids and of larvae present on the plants are counted.

The results obtained are given in table 7:

TABLE 7

| Clone No. | Number of acclimatized plantlets | Number of inoculated plantlets | Number of resistant plantlets | Number of "intermediate" plantlets | Number of sensitive plantlets | Comments |
|---|---|---|---|---|---|---|
| CITz1 | 5 | 5 | 0 | 0 | 5 | Sensitive control |
| CITz3 | 5 | 5 | 5 | 0 | 0 | Resistant control |
| V2.3 | 9 | 9 | 0 | 0 | 9 | Sensitive |
| V2.4 | 6 | 4 | 2 | 2 | 0 | Presence of floral buds |
| V2.12 | 12 | 11 | 0 | 0 | 11 | Sensitive |
| V2.15 | 6 | 6 | 6 | 0 | 0 | Resistant |
| V3.1 | 12 | 12 | 12 | 0 | 0 | Resistant |
| V3.6 | 4 | 4 | 4 | 0 | 0 | Resistant |
| V4.18 | 7 | 7 | 7 | 0 | 0 | Resistant |
| V4.45 | 7 | 7 | 0 | 0 | 7 | Sensitive |
| V7.19 | 7 | 7 | 7 | 0 | 0 | Resistant |
| V7.25 | 7 | 7 | 0 | 0 | 7 | Sensitive |
| V8.26 | 8 | 7 | 0 | 0 | 7 | Sensitive |

These results show that clones M1, M4, V2.15, V3.1, V3.6, V4.18 and V7.19 are resistant to the aphids.

Measurement of the Resistance to Viral Transmission by *A. gossypii*

The viral transmission tests are carried out essentially as described by Pitrat and Lecoq (Phytopathology, 70, 958-961, 1980). The CMV (Cucumber Mosaic Virus) strain I17F can be used for the tests of transmission by *A. gossypii* in the transformed plants and the Vedrantais and Margot control lines. The virus is multiplied on Vedrantais melons by mechanical inoculation. After 1 day without food, the adult aphids are deposited, for 5 minutes of acquisition, on virus-infected leaves placed in a Petri dish. The aphids are then transferred onto the plants to be tested. Approximately 15 minutes after depositing the viruliferous aphids, the aphids are removed with a brush and the plants are then treated with an insecticide and placed in a culture chamber (12 hours day at 24° C. and 12 hours night at 18° C.). Two weeks after inoculation, the plants sensitive to transmission of CMV by *A. gossypii* develop severe mosaic symptoms. The resistant plants show no symptoms and the virus is not detected by ELISA in these plants. The ELISA assay follows the protocol described by Clark and Adams (J. Gen. Virol., 34, 475-483, 1997) with an antibody directed against the CMV capsid protein (Adgen, provided by the company LCA, Bordeaux, France).

EXAMPLE 7

Functional Validation in the Tomato

Tomato Transformation

The transformation protocol is adapted from Hamza and Chupeau (J. Exp. Bot., 44, 1837-1845, 1993) by P. Rousselle (INRA, Montfavet, France) using cotyledons of several Ferum (INRA line) and Montfavet 63.5 (F1 hybrid) genotypes.

The strains used for the transformation are those described in example 5. The regenerated and rooted plants are analyzed by flow cytometry, and only the diploid plants are conserved.

The molecular analyses, the aim of which is to verify the presence of the insert containing the nptII gene and the Vat gene and also the expression thereof in the genome of the regenerated plants, are carried out by PCR and RT-PCR. The PCR conditions used are identical to those described in example 6. Four pairs of primers were used: V1684 (SEQ ID No.: 13 and SEQ ID No.: 14) located in the Vat promoter, the pairs of primers for the markers D (SEQ ID No.: 23 and SEQ ID No.: 24) and E (SEQ ID No.: 21 and SEQ ID No.: 22) located in the middle of the Vat gene and the V632 primers which amplify a fragment located 3' of the gene. The sequences of the V632 primers are as follows:

```
Vat 632R:
CTGGTGATGACATTCATATCTTCC    (SEQ ID No.: 29)

Vat 632F:
CCCAGCAACATACTGATTCCAAGC.   (SEQ ID No.: 30)
```

Several series of transformations are carried out on the tomato using the various constructs (table 8) and on two different Ferum and Montfavet genotypes (INRA).

TABLE 8

| Genotype | Construct | Number of explants in culture | Number of diploid rooted plants | nptII | Vat marker V1684 | Vat marker E | Vat marker D | Vat marker V632 | PicA+/PicA− |
|---|---|---|---|---|---|---|---|---|---|
| Ferum | B1-1 | 120 | 0 | 0 | 0 | 0 | 0 | 0 | 0 |
| Ferum | B1-2 | 105 | 3 | 3 | 3 | 2* | 2* | 2* | 0 |
| Ferum | B1-3 | 90 | 0 | 0 | 0 | 0 | 0 | 0 | 0 |
| Ferum | A6-3 | 120 | 0 | 0 | 0 | 0 | 0 | 0 | 0 |
| Montfavet | B1-1 | 90 | 1 | 1 | 1 | 1 | 1 | 1 | 0 |
| Montfavet | B1-2 | 80 | 6 | 6 | 3 | 4 | 4 | 4 | 0 |
| Montfavet | B1-3 | 80 | 3 | 3 | 3 | 2 | 2 | 2 | 0 |
| Montfavet | A6-3 | 91 | 11 | 10 | ** | 9 | 10 | 10 | 0 |
| Untransformed Ferum sensitive control | | | 0 | 0 | 0 | 0 | 0 | 0 | 0 |
| Montfavet sensitive control | | | 0 | 0 | 0 | 0 | 0 | 0 | 0 |

*Two plants (T2 and T7) integrated the whole insert. In the third plant, only the nptII gene and a fraction of the Vat gene (including the marker V1684) were integrated.
** The A6-3 construct contains the Vat gene under the control of the 35S promoter; the pair of primers V1684 (located on a region of the Vat promoter) does not make it possible to screen the transformants.

The molecular analyses by RT-PCR on plant T7 and a Ferum control with the pair of primers for the marker D (according to the conditions described in example 6) made it possible to reveal the expression of the Vat gene in the transformed plant (T7).

The set of primers used on the transformed plants of the Montfavet genotype makes it possible to determine 14 plants originating from different explants that have integrated the whole transgene.

In total, 2 plants of the Ferum genotype and 14 plants of the Montfavet 63.5 genotype integrated the Vat gene.

Only the transformed plants are propagated by taking cuttings, separated and acclimatized in a climate-controlled chamber (8 h night at 18° C.-16 h day at 24° C.) for 4 weeks before the biological tests are carried out. Only the two Ferum plants have been analyzed to date.

Measurement of Viral Transmission

The same *A. gossypii* strain (Nm1) and the same protocol for transmission by *A. gossypii* as for the tests for viral transmission resistance on the melon are used. The virus chosen is CMV (cucumber mosaic virus) strain I17F, which infects the melon and the tomato. This strain is effectively transmitted to the tomato when it is mechanically inoculated or transmitted by *Myzus persicae* (Jacquemond et al., Molecular Breeding, 8(1), 85-94, 2001). The virus is multiplied on Vedrantais melon plantlets. The acquisition of CMV by *A. gossypii* is carried out on these infected melon plantlets. The transmission is carried out on tomato plantlets derived from in vitro although at the 5-leaf stage, or on plantlets derived from sowing, at the 2-leaf stage (approximately 5 weeks after sowing), by depositing 10 viruliferous aphids onto each plant. The rate of transmission on each genotype (control and transformed tomatoes) is evaluated on at least 2 repetitions of 20 plants. The sensitive control variety is the Ferum variety.

The ELISA assay follows the protocol described by Clark and Adams (J. Gen. Virol., 34, 475-483, 1977) with an antibody directed against the CMV capsid protein (Adgen, provided by the company LCA, Bordeaux, France).

The first results obtained on a small number of plants are described in table 9.

TABLE 9

| | | Evaluation at 21 days after infection | |
|---|---|---|---|
| Plants | Number of plants tested | Number of infected plants | Number of non-infected plants* |
| Ferum sensitive control | 6 | 6 | 0 |
| Ferum T1 | 9 | 9 | 0 |
| Ferum T2 | 3 | 2 | 1 |
| Ferum T7 | 6 | 3 | 3 |

*absence of symptoms and of virus detected by ELISA

The plants of code T1, carrying a truncated Vat gene, and those of the sensitive control are 100% infected. In a few transformed plants of codes T2 and T7, the virus was not transmitted, which suggests that the Vat gene has an effect on resistance to viral transmission by *A. gossypii* in the transgenic tomatoes having integrated Vat.

EXAMPLE 8

Functional Validation in the Cotton Plant

Cotton Plant Transformation

The genetic transformation of the cotton plant (*Gossypium hirsutum* L.) is based on the regeneration of transformants via a process of somatic embryogenesis published by Shoemaker et al. (Plant Cell Reports, 3, 178-181, 1986) and by Trolinder and Goodin (Plant Cell Reports, 6, 231-234, 1987). This method of transformation uses the *Agrobacterium tumefaciens* bacterium as transformation vector according to Umbeck et al. (Biotechnology, 5, 263-266, 1987) and Firoozabady et al. (Plant Molecular Biology, 10, 105-116, 1987) with a few modifications and adaptations with respect to the publications mentioned. The Agrobacterium strains used for the transformation are the same as those described in example 5, and in particular the LBA4404, C58C1pGV2260 and C58C1pMP90 strains. The first strain contains either the plasmid pSLJ7292 composed, inter alia, of the kanamycin resistance gene under the control of the Nos promoter and the Vat gene under the control of its own promoter, or the plasmid pBin 61 which comprises the Vat gene under the control of the 35S promoter. The other two strains carry the plasmid pBin 19 composed, inter alia, of the kanamycin resistance gene under the control of the Nos promoter and the Vat gene under the control of its own promoter.

Cotton Plant Regeneration

Hypocotyl explants (variety Coker 310) taken from young plants cultivated under aseptic conditions are used. They are brought into contact with the *Agrobacterium* for 20 minutes and then placed in culture for 48 hours on a culture medium (basic medium) composed of the Murashige and Skoog (MS) mineral elements, 30 g·l$^{-1}$ of glucose, the Morel and Wetmore vitamins (Am. J. Bot., 38, 141-143, 1951), 0.1 to 0.05 mg·l$^{-1}$ of 2,4-dichlorophenoxyacetic acid and 0.1 to 0.01 mg·l$^{-1}$ of kinetin. This medium contains neither selection agent nor antibiotic whose aim is to halt the growth of the bacterium. After this period of coculture, the explants are subcultured on the same medium supplemented with kanamycin at a concentration of 25 mg·l$^{-1}$ and with cefotaxime at a concentration of 500 mg·l$^{-1}$. The explants are then subcultured every two weeks on this same medium. The calluses derived from the proliferation of the transformed cells appear after 3 to 5 weeks of culture. When their size reaches approximately 0.5 cm in diameter, they are isolated and subcultured on the same medium in which the cefotaxime concentration has been decreased by half and the concentration of growth substances (2,4-dichlorophenoxyacetic acid and kinetin) has also been decreased. Subculturing is then carried out every 2 weeks until the embryonic tissues appear. Depending on the behavior of the calluses, sequences of media that vary in terms of the concentration of growth substances can be applied. The embryonic tissues are isolated on the base medium without the addition of growth substances. On this medium, a certain proportion of the pro-embryos develop into plantlets. The latter are transferred into a tube on a vermiculite support "watered" with the liquid base medium free of growth substances and in which sucrose replaces glucose. When they reach a size of approximately 4-6 cm, they are directly transferred under glass of S2 type.

Molecular analysis, the aim of which is to verify the presence of the Vat gene and its expression in the genome of the regenerated plants, is carried out by PCR. One pair of primers is used to amplify the nptII gene. Two pairs of primers were used for the Vat gene: the first pair, called 632, amplifies a Vat fragment located 3' of the gene, the second, called LRR, amplifies a fragment located in the middle of the gene.

The sequences of the pair of primers used to amplify the nptII gene are as follows:

```
Kana III
GCGATAGAAGGCGATGCG          (SEQ ID No.: 26)

Kana R
CCGGCTACCTGCCATTCG.         (SEQ ID No.: 31)
```

The sequences of the pair of primers 632 are as follows:

```
Vat632F:
CCCAGCAACATACTGATTCCAAGC    (SEQ ID No.: 30)

Vat632R:
CTGGTGATGACATTCATATCTTCC.   (SEQ ID No.: 29)
```

The sequences of the pair of primers LRR are as follows:

```
LRR F:
GTTGTTGAGAGCAATAGTGTAC      (SEQ ID No.: 32)

LRR R:
CCTTAGAGAAGAATGAAGTCTC.     (SEQ ID No.: 33)
```

The PCR conditions are as follows, whatever the primers used:

For 25 µl of reaction medium:

Water: 9.5 µl

10× buffer: 2.5 µl dNTP (2.5 mM): 2 µl

Oligo 1 (10 µM): 2.5 µl

Oligo 2 (10 µM): 2.5 µl

Taq (5 U/µl): 0.25 µl

DNA: 5 µl

Program:

3 minutes at 94° C.

then 35 cycles of: 30 seconds at 94° C.-45 seconds at 59° C.-45 seconds at 72° C.

In total, after 8 months, 12 transformed plants were transferred under glass; they are derived from 5 different embryonic strains. Among these, 2 are derived from 2 different strains for which amplification of the Vat gene was obtained under the PCR conditions presented above. The others are derived from strains for which amplification of the nptII gene was obtained but not that of the Vat gene. It is not impossible that they represent false negatives insofar as, by varying the amount of template, it has been possible to obtain amplification at the correct size with an extract that had previously been found to be negative.

Measurement of the Resistance to Infection by *Aphis gossypii*

An *A. gossypii* clone taken from a cotton plant (origin Reunion) is used and maintained on cotton plants. This is because it has been shown that *A. gossypii* populations are highly structured genetically according to the host plant (Vanlerberghe-Masutti and Chavigny, Molecular Ecology, 7, 905-914, 1998). The test is carried out according to the same protocol as on the melon, but with plant culture conditions adapted to the cotton plant. The cotton plants are maintained under glass of S2 type at a temperature of 28° C. to 30° C., and support lighting, in terms of intensity and duration, is provided for a 12-12 photoperiod.

In addition to the evaluation of resistance carried out as for the melon test, a more precise evaluation of the life history of the aphids on the transformed plants (duration of the various larval stages, duration of adult survival, intrinsic growth rate, etc.) (Xia et al., Entomologia Experimentalis et Applicata, 90, 25-35, 1999) can also be carried out in order to detect possibly weaker effects of the Vat gene on *A. gossypii* in a heterologous situation.

What is claimed is:

1. An isolated polynucleotide selected from the group consisting of: a) a polynucleotide encoding a polypeptide involved in resistance to the aphid *Aphis gossypii* and/or to viral transmission by said aphid, wherein said polypeptide is at least 95% identical to SEQ ID NO: 3; and b) a polynucleotide complementary to the polynucleotide of a).

2. An isolated polynucleotide selected from the group consisting of: a) the polynucleotide sequence of SEQ ID NO: 1;
b) the polynucleotide sequence of SEQ ID NO: 2; and
c) a polynucleotide complementary to the polynucleotide a) or to the polynucleotide b).

3. An isolated polynucleotide encoding a polypeptide involved in resistance to the aphid *Aphis gossypii* and/or to viral transmission by said aphid, wherein said polynucleotide is obtained by screening a plant genomic DNA or cDNA library with the polynucleotide as claimed in claim 1.

4. An expression cassette comprising the polynucleotide as claimed in claim 1, under the transcriptional control of a suitable promoter.

5. A recombinant vector comprising the polynucleotide as claimed in claim 1.

6. A cell that is genetically transformed with the polynucleotide as claimed in claim 1.

7. A method for producing a transgenic plant resistant to the aphid *Aphis gossypii* and/or to viral transmission by said aphid comprising genetically transforming a plant with the polynucleotide as claimed in claim 1.

8. A transgenic plant that is genetically transformed with the polynucleotide as claimed in claim 1.

9. The transgenic plant as claimed in claim 8, said plant is from a family selected from the group consisting of: from the Cucurbitaceae, the Malvaceae and the Solanaceae.

10. A recombinant vector comprising the expression cassette as claimed in claim 4.

11. The isolated polynucleotide as claimed in claim 1, wherein said polypeptide is at least 98% identical to the polypeptide sequence of SEQ ID NO: 3.

12. The isolated polynucleotide as claimed in claim 1, wherein said polypeptide is at least 99% identical to the polypeptide sequence of SEQ ID NO: 3.

* * * * *

UNITED STATES PATENT AND TRADEMARK OFFICE
CERTIFICATE OF CORRECTION

PATENT NO. : 7,576,264 B2 Page 1 of 1
APPLICATION NO. : 10/542337
DATED : August 18, 2009
INVENTOR(S) : Dogimont et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 585 days.

Signed and Sealed this

Seventh Day of September, 2010

David J. Kappos
*Director of the United States Patent and Trademark Office*

SEQUENCE LISTING

<160> NUMBER OF SEQ ID NOS: 33

<210> SEQ ID NO 1
<211> LENGTH: 10922
<212> TYPE: DNA
<213> ORGANISM: Cucumis melo
<220> FEATURE:
<221> NAME/KEY: exon
<222> LOCATION: (2344)..(4710)
<223> OTHER INFORMATION:
<220> FEATURE:
<221> NAME/KEY: Intron
<222> LOCATION: (4711)..(5264)
<223> OTHER INFORMATION:
<220> FEATURE:
<221> NAME/KEY: exon
<222> LOCATION: (5265)..(6398)
<223> OTHER INFORMATION:
<220> FEATURE:
<221> NAME/KEY: Intron
<222> LOCATION: (6399)..(7219)
<223> OTHER INFORMATION:
<220> FEATURE:
<221> NAME/KEY: exon
<222> LOCATION: (7220)..(8077)
<223> OTHER INFORMATION:
<220> FEATURE:
<221> NAME/KEY: Intron
<222> LOCATION: (8078)..(8176)
<223> OTHER INFORMATION:
<220> FEATURE:
<221> NAME/KEY: exon
<222> LOCATION: (8177)..(8239)
<223> OTHER INFORMATION:

<400> SEQUENCE: 1

```
ccggagtgta cataataagg agacaccatc acaagtcttg aagctttggc gctcttgaaa        60
ttcagctttt aaattaatta gtcatgtttt tcaaatatat aacataggag aatatgagtt       120
ttgcgtcaaa tcccatcttg gcagagtgta ttttgatgaa attccttatt ggaaggaact       180
gccatatttt tagaatttgg aatctgtaaa gttattctca tgtggttttt tgggcagtgg       240
agggagttgg agaagttgat tggtgtgcag atctatgtat aggacagatc attgaagagg       300
aaaaaagaat tggaatatta gggatttggt taattaagca atatgggaag ttggatttca       360
gaattgcaat tcatgattgg gtttcgattt aggaagaatg gacttgcaaa ttcaatttaa       420
cataaaattt cttttttttt tcctaaatta atttttattt gatcttcgga ctcatccaat       480
gcaatttaca ggtcactaca aacaatatcc atgtcagcac acataacgtg tctagtagac       540
attacgttaa cttaatgtag gaaacaaaaa gaaaaacgaa aaaggcaaga aatgaaaaag       600
gaaacgttgt gtatgatgat taaaatgtac gttgatagct aaattcaact ttgttcttca       660
ttagcaacaa caagggacaa caaaatgaaa atttcagcac agttatggaa tgttgaagaa       720
gaaggtgacg agagagatgc cacatcataa aaaattaata ttataatcat ttttgtcaca       780
tcagttttct gattacttat atttaaccta cacatcattt tgccgttact caactaacga       840
tcgatatgac ctttaaagct cgatgattaa aatgtttatt ttgaactttc agggactata       900
taaatgtata tatatcaact tcaaatctta gcggtcaaaa gtgcattttg ttttagttta       960
aaacaccgag atgtgacgat taataatgcc tacacactca cgtactcaca catgcagtga      1020
gttttttatg ttttttttac acacattaga cgcaaattga attcctaatt ccattcccta      1080
agacaagttt ctaatgactt atacaattca cataggcatg catgcagaac aagcgaaaaa      1140
cgacgaattt accttaagaa aatggcccaa ccaaccactt acacaatctc aggcatacca      1200
```

```
ttccccggga tgaaagaatt ttgcctgtaa ttcattcgat ctcaggcata caatgcatcg   1260
agaagacgca aaatgaaaga caaaagtata gaacaacaca atcctgtact tcattttaaa   1320
cgatagtttt caaatttaac gatcgtgtag atcatgatac acgatctcga gccttagtgg   1380
caccgagatg gcccgagatg aaagaattat gtctttattt tattcgatat taagcataca   1440
ttacttcgag atgaaagacc tctacccttta gttattcgat ctcgagcctt aattgaatcg   1500
agatgaccca agattgatag atcgcaaaga agatatatat cgtaagggca tatatgaaat   1560
ttatgaaaat acgatcatgt gtcataaact tttcttattt tgttatatag accgtaaata   1620
ttatagattt tggttacatt tgtgtaaatt actctatttt tttttagtaa aacaaatgaa   1680 ttaaatttt taaaaaaaaa ttattgagag ttgaagtaat tgggtgtttt ctaaaagatt   1740
gaaataaata cctttattaa ctttgcaaat atattttcaa agaggctaac aaatcaaata   1800
tattttctaa aaaaatcaca ttgcgttggg gataaggtaa gagtaatgga aaaatgaaag   1860
gttgtgaaca attcgtactc ttacttatga gatttgacag aacaaatatt tttcaaatac   1920 tcttttacg ttttctttt taaaattaaa taacaaatac ttttccactg cttttctttt   1980
cttccattga ctcctcaact aataattttg gtcttcccat tattatcttc ttcttcttca   2040
tttttctctg cactgtctct tctccatttc aacatcttct tatatcttca ttcaggttaa   2100
atatttcatc ccttaccatt tttatttaca ttttccatct gatcatttct atacttataa   2160
actcgataat ttgtttagac tttctttaga tagttttttac ttggtgatct gtatgtgttc   2220
actcctactt ttctgttagg caaaatcttc aaaattatta tggttcattc ctcgtggttt   2280
tttagctctt caagtatttt tgtaggtttt gatcctttc aagctcaaga acagaggata   2340 ata atg gac atc ctt att tca gtc act gca aaa att gcc gaa tac act   2388
    Met Asp Ile Leu Ile Ser Val Thr Ala Lys Ile Ala Glu Tyr Thr
    1               5                   10                  15 gtt gag cct gtt gga cgc caa ctt ggt tat gta ttt ttc att cgt tcc   2436
Val Glu Pro Val Gly Arg Gln Leu Gly Tyr Val Phe Phe Ile Arg Ser
            20                  25                  30 aac ttt caa aaa ctt aag act caa gta gaa aag ctg aag att aca aga   2484
Asn Phe Gln Lys Leu Lys Thr Gln Val Glu Lys Leu Lys Ile Thr Arg
        35                  40                  45 gag tct gtg caa cac aag atc cat agt gca aga aga aat gct gaa gac   2532
Glu Ser Val Gln His Lys Ile His Ser Ala Arg Arg Asn Ala Glu Asp
    50                  55                  60 ata aaa cct gcc gtt gag gaa tgg ttg aaa aag gtc gat gac ttt gtc   2580
Ile Lys Pro Ala Val Glu Glu Trp Leu Lys Lys Val Asp Asp Phe Val
65                  70                  75 cga gaa tct gac gag ata tta gcc aat gaa ggt gga cat ggt gga ctc   2628
Arg Glu Ser Asp Glu Ile Leu Ala Asn Glu Gly Gly His Gly Gly Leu
80                  85                  90                  95 tgt tcc acc tat ttg gtc caa cga cac aag tta agt aga aaa gca agc   2676
Cys Ser Thr Tyr Leu Val Gln Arg His Lys Leu Ser Arg Lys Ala Ser
                100                 105                 110 aaa atg gta gat gag gtt ctt gag atg aaa aat gag ggg gaa agt ttt   2724
Lys Met Val Asp Glu Val Leu Glu Met Lys Asn Glu Gly Glu Ser Phe
            115                 120                 125 gat atg gta tcc tat aaa agt gtt atc cca tca gtt gat tgt tca ctt   2772
Asp Met Val Ser Tyr Lys Ser Val Ile Pro Ser Val Asp Cys Ser Leu
        130                 135                 140 cca aaa gtg cct gac ttt ctt gac ttt gag tca aga aag tcg att atg   2820
Pro Lys Val Pro Asp Phe Leu Asp Phe Glu Ser Arg Lys Ser Ile Met
    145                 150                 155
```

```
                                                        -continued gaa caa atc atg gat gca cta tct gat ggt aat gtc cat agg att gga      2868
Glu Gln Ile Met Asp Ala Leu Ser Asp Gly Asn Val His Arg Ile Gly
160             165                 170                 175 gta tat ggg atg ggg ggt gtt ggc aaa aca atg cta gtg aag gat att      2916
Val Tyr Gly Met Gly Gly Val Gly Lys Thr Met Leu Val Lys Asp Ile
        180                 185                 190 tta aga aaa att gtg gag agt aag aag cct ttt gat gag gtg gta aca      2964
Leu Arg Lys Ile Val Glu Ser Lys Lys Pro Phe Asp Glu Val Val Thr
    195                 200                 205 tcc acg atc agc caa aca cca gat ttt aga agt atc caa gga caa cta      3012
Ser Thr Ile Ser Gln Thr Pro Asp Phe Arg Ser Ile Gln Gly Gln Leu
210                 215                 220 gct gac aag cta ggt ttg aaa ttc gaa caa gaa aca ata gaa gga agg      3060
Ala Asp Lys Leu Gly Leu Lys Phe Glu Gln Glu Thr Ile Glu Gly Arg
            225                 230                 235 gct act att cta cga aag agg tta aag atg gag aga agt atc cta gtt      3108
Ala Thr Ile Leu Arg Lys Arg Leu Lys Met Glu Arg Ser Ile Leu Val
240                 245                 250                 255 gtg ttg gat gat gtt tgg gag tat att gat ttg gaa act ata gga att      3156
Val Leu Asp Asp Val Trp Glu Tyr Ile Asp Leu Glu Thr Ile Gly Ile
                260                 265                 270 cca agt gtt gaa gat cat acg ggg tgc aag atc ttg ttt acc act agg      3204
Pro Ser Val Glu Asp His Thr Gly Cys Lys Ile Leu Phe Thr Thr Arg
            275                 280                 285 att aaa cat ttg atc tca aat caa atg tgc gcc aat aaa att ttt gag      3252
Ile Lys His Leu Ile Ser Asn Gln Met Cys Ala Asn Lys Ile Phe Glu
        290                 295                 300 ata aaa gtt tta gga aaa gat gag tca tgg aat tta ttt aag gca atg      3300
Ile Lys Val Leu Gly Lys Asp Glu Ser Trp Asn Leu Phe Lys Ala Met
305                 310                 315 gca ggt gac att gtt gat gca agt gat ttg aag cct ata gcc att cga      3348
Ala Gly Asp Ile Val Asp Ala Ser Asp Leu Lys Pro Ile Ala Ile Arg
320                 325                 330                 335 att gtg aga gaa tgt gca ggt ttg cct att gct att act act gtt gct      3396
Ile Val Arg Glu Cys Ala Gly Leu Pro Ile Ala Ile Thr Thr Val Ala
                340                 345                 350 aag gca tta cga aat aaa cct tcc gac att tgg aat gat gcc tta gat      3444
Lys Ala Leu Arg Asn Lys Pro Ser Asp Ile Trp Asn Asp Ala Leu Asp
            355                 360                 365 cag ctt aaa act gtt gat gtg ggt atg gca aac att gga gaa atg gaa      3492
Gln Leu Lys Thr Val Asp Val Gly Met Ala Asn Ile Gly Glu Met Glu
        370                 375                 380 aag aaa gtg tat ttg tca cta aaa ctg agt tac gat tgc ttg gga tat      3540
Lys Lys Val Tyr Leu Ser Leu Lys Leu Ser Tyr Asp Cys Leu Gly Tyr
385                 390                 395 gaa gag gtg aag tta tta ttc ttg tta tgc agc atg ttt cca gaa gac      3588
Glu Glu Val Lys Leu Leu Phe Leu Leu Cys Ser Met Phe Pro Glu Asp
400                 405                 410                 415 ttt agc att gac gtg gaa ggg ttg cat gta tat gcc atg ggc atg gga      3636
Phe Ser Ile Asp Val Glu Gly Leu His Val Tyr Ala Met Gly Met Gly
                420                 425                 430 ttc tta cat ggt gtt gat act gtg gta aaa gga cga cgt agg ata aaa      3684
Phe Leu His Gly Val Asp Thr Val Val Lys Gly Arg Arg Arg Ile Lys
            435                 440                 445 aaa ttg gtt gat gat ctt ata tct tct tct ttg ctt caa caa tat tct      3732
Lys Leu Val Asp Asp Leu Ile Ser Ser Ser Leu Leu Gln Gln Tyr Ser
        450                 455                 460 gag tat ggg tgc aat tat gtg aaa atg cat gat atg gtt cgt gat gta      3780
Glu Tyr Gly Cys Asn Tyr Val Lys Met His Asp Met Val Arg Asp Val
465                 470                 475
```

```
gcc cta tta att gca tct aag aat gaa cac gta cgt aca ttg agc tat    3828
Ala Leu Leu Ile Ala Ser Lys Asn Glu His Val Arg Thr Leu Ser Tyr
480                 485                 490                 495 gtg aaa aga tcg aat gaa gaa tgg gaa gaa gag aaa cta ttg ggt aat    3876
Val Lys Arg Ser Asn Glu Glu Trp Glu Glu Glu Lys Leu Leu Gly Asn
                500                 505                 510 cat acc gca gtg ttc att gat ggt tta cat tat cct ctc ccg aag tta    3924
His Thr Ala Val Phe Ile Asp Gly Leu His Tyr Pro Leu Pro Lys Leu
            515                 520                 525 acg tta ccc aaa gtt caa tta tta agg tta gtt gca aaa tat tgt tgg    3972
Thr Leu Pro Lys Val Gln Leu Leu Arg Leu Val Ala Lys Tyr Cys Trp
        530                 535                 540 gaa cat aat aag cgt gtg tcg gtg gta gaa act ttt ttt gaa gaa atg    4020
Glu His Asn Lys Arg Val Ser Val Val Glu Thr Phe Phe Glu Glu Met
    545                 550                 555 aaa gag ctc aaa ggt tta gta gta gaa aac gta aat ata tca ttg atg    4068
Lys Glu Leu Lys Gly Leu Val Val Glu Asn Val Asn Ile Ser Leu Met
560                 565                 570                 575 caa cga cca tct gat gtt tac tcc tta gca aac atc aga gta tta cgt    4116
Gln Arg Pro Ser Asp Val Tyr Ser Leu Ala Asn Ile Arg Val Leu Arg
                580                 585                 590 ttg gaa aga tgt caa tta tta ggg agc ata gat tgg att ggt gaa tta    4164
Leu Glu Arg Cys Gln Leu Leu Gly Ser Ile Asp Trp Ile Gly Glu Leu
            595                 600                 605 aaa aag ctt gaa att ctt gat ttt agt gaa tct aac atc aca caa att    4212
Lys Lys Leu Glu Ile Leu Asp Phe Ser Glu Ser Asn Ile Thr Gln Ile
        610                 615                 620 cct aca acc atg agc caa ttg aca cag cta aaa gtg ttg aat tta tct    4260
Pro Thr Thr Met Ser Gln Leu Thr Gln Leu Lys Val Leu Asn Leu Ser
    625                 630                 635 tct tgt gaa caa ctt gag gta att cca cca aat att ctt tca aag ttg    4308
Ser Cys Glu Gln Leu Glu Val Ile Pro Pro Asn Ile Leu Ser Lys Leu
640                 645                 650                 655 aca aaa ttg gaa gaa tta gat ctg gaa act ttt gat gga tgg gaa gga    4356
Thr Lys Leu Glu Glu Leu Asp Leu Glu Thr Phe Asp Gly Trp Glu Gly
                660                 665                 670 gaa gaa tgg tat gaa gga agg aaa aat gct agc ctt tct gaa ctc aag    4404
Glu Glu Trp Tyr Glu Gly Arg Lys Asn Ala Ser Leu Ser Glu Leu Lys
            675                 680                 685 tgc ttg cga cac ctt tat gct tta aac tta acc att caa gat gaa gaa    4452
Cys Leu Arg His Leu Tyr Ala Leu Asn Leu Thr Ile Gln Asp Glu Glu
        690                 695                 700 att atg cca gaa aac ttg ttc tta gtt ggg aag ttg aag ctt caa aaa    4500
Ile Met Pro Glu Asn Leu Phe Leu Val Gly Lys Leu Lys Leu Gln Lys
    705                 710                 715 ttc aac att tgt att ggt tgc gaa agc aaa tta aag tat act ttt gca    4548
Phe Asn Ile Cys Ile Gly Cys Glu Ser Lys Leu Lys Tyr Thr Phe Ala
720                 725                 730                 735 tac aag aac aga atc aaa aac ttc att gga atc aag atg gaa tca gga    4596
Tyr Lys Asn Arg Ile Lys Asn Phe Ile Gly Ile Lys Met Glu Ser Gly
                740                 745                 750 agg tgc ttg gat gat tgg ata aaa aat ttg tta aag agg tcg gac aat    4644
Arg Cys Leu Asp Asp Trp Ile Lys Asn Leu Leu Lys Arg Ser Asp Asn
            755                 760                 765 gtg ctt ttg gaa gga tca gtt tgt tca aag gtt ctc cac tca gaa ttg    4692
Val Leu Leu Glu Gly Ser Val Cys Ser Lys Val Leu His Ser Glu Leu
        770                 775                 780 gta ggt gcc aat aac ttc gtaagtttgc agtatctcta cctttatgat          4740
Val Gly Ala Asn Asn Phe
```

```
                                                                             -continued
      785 aattcaaaat ttcaacattt tatcaacgtt agcaatacca tcaacattga agaatcattt            4800 tttagtgaaa tggtaaattt catcaacaca tttttctatg tttctatata cacatcaaaa            4860 tttataaatc acctgtttgt tcattttat tgttccttcc acaagttcct tctaacattt             4920 gtggttagta atgatattag ggataagatt ctattcttct ttgttttaga aggctcttct            4980 cttggtgtag agagactctt tcttgtttca tacattaatg ataatatata attttagact            5040 tctaaaatat ataaatgcat gtcaggtgat attccaagaa aatttaaaga agtttattag            5100 atatttccta tctaaggaag caaatttgaa gtaatcattt tacacaattt gttatggtaa            5160 ttttaaaaca ctatataaat tatatgttgt tagttagcat cagttgtgat gatatggtta            5220 attacgttgt cacaaactga acttttaagg acgtaaattt gtag gta tca ctt cct             5276
                                                    Val Ser Leu Pro
                                                        790 aat ttg gag aag ttg gaa att gtg aat gca aag agt ttg aag atg ata             5324
Asn Leu Glu Lys Leu Glu Ile Val Asn Ala Lys Ser Leu Lys Met Ile
    795                 800                 805 tgg agc aat aac gtg cca att ctt aat tcc ttt tcc aaa ctc gag gaa             5372
Trp Ser Asn Asn Val Pro Ile Leu Asn Ser Phe Ser Lys Leu Glu Glu
810                 815                 820                 825 ata aaa att tat tca tgc aac aat ctt caa aaa gta tta ttt cct cca             5420
Ile Lys Ile Tyr Ser Cys Asn Asn Leu Gln Lys Val Leu Phe Pro Pro
                830                 835                 840 aat atg atg gac att ctc aca tgc ctt aaa gtc tta gag atc aaa aat             5468
Asn Met Met Asp Ile Leu Thr Cys Leu Lys Val Leu Glu Ile Lys Asn
            845                 850                 855 tgt gat ttg ttg gaa ggg ata ttt gaa gcg caa gag cca att agt gtt             5516
Cys Asp Leu Leu Glu Gly Ile Phe Glu Ala Gln Glu Pro Ile Ser Val
        860                 865                 870 gtt gag agc aat aat tta ccc att ctt aat tcc ttt tcc aaa ctc gag             5564
Val Glu Ser Asn Asn Leu Pro Ile Leu Asn Ser Phe Ser Lys Leu Glu
    875                 880                 885 gaa ata aga att tgg tca tgc aac aat ctt caa aaa gta tta ttt cct             5612
Glu Ile Arg Ile Trp Ser Cys Asn Asn Leu Gln Lys Val Leu Phe Pro
890                 895                 900                 905 tca aat atg atg ggc att ctt cca tgc ctt aaa gtc tta gat att aga             5660
Ser Asn Met Met Gly Ile Leu Pro Cys Leu Lys Val Leu Asp Ile Arg
                910                 915                 920 ggt tgt gaa ttg ttg gaa ggg ata ttt gaa gtg caa gag cca att agt             5708
Gly Cys Glu Leu Leu Glu Gly Ile Phe Glu Val Gln Glu Pro Ile Ser
            925                 930                 935 gtt gtt gag agc aat agt gta ccc att ctt aat tcc ttt tcc aaa ctc             5756
Val Val Glu Ser Asn Ser Val Pro Ile Leu Asn Ser Phe Ser Lys Leu
        940                 945                 950 gag aaa ata aga att tgg tca tgc aac aat ctt caa aaa ata tta ttt             5804
Glu Lys Ile Arg Ile Trp Ser Cys Asn Asn Leu Gln Lys Ile Leu Phe
    955                 960                 965 cct tca aat atg atg ggc att ctt aca tgc ctt aaa gtc tta gag atc             5852
Pro Ser Asn Met Met Gly Ile Leu Thr Cys Leu Lys Val Leu Glu Ile
970                 975                 980                 985 aga gat tgt gaa ttg ttg gaa ggg ata ttt gaa gtg caa gag cca  att            5900
Arg Asp Cys Glu Leu Leu Glu Gly Ile Phe Glu Val Gln Glu Pro  Ile
                990                 995                 1000 agt gtt gtt gag  agc aat aat tta ccc  att ctt aat tcc ttt  tcc              5945
Ser Val Val Glu  Ser Asn Asn Leu Pro  Ile Leu Asn Ser Phe  Ser
                1005                 1010                 1015 aaa ctc gag gaa  ata aga att ggg tca  tgc aac aat ctt caa  aaa              5990
```

```
                                                          -continued

Lys Leu Glu Glu  Ile Arg Ile Gly  Ser Cys Asn Asn  Leu Gln Lys
        1020              1025              1030 gta tta ttt cct  cca aat atg atg  ggc att ctt aca  tgc ctt aaa           6035
Val Leu Phe Pro  Pro Asn Met Met  Gly Ile Leu Thr  Cys Leu Lys
        1035              1040              1045 gtc tta gag att  aga cat tgt aat  ttg ttg gaa ggg  ata ttt gaa           6080
Val Leu Glu Ile  Arg His Cys Asn  Leu Leu Glu Gly  Ile Phe Glu
        1050              1055              1060 gtg caa gag cca  att agt att gtt  gaa gcg agt cct  atc ttg ctc           6125
Val Gln Glu Pro  Ile Ser Ile Val  Glu Ala Ser Pro  Ile Leu Leu
        1065              1070              1075 caa aat tta tct  tcg ttg atg tta  tgt aat ctt cca  aac ctt gag           6170
Gln Asn Leu Ser  Ser Leu Met Leu  Cys Asn Leu Pro  Asn Leu Glu
        1080              1085              1090 tac gtg tgg agc  aaa aat cct tat  gaa ctt ctg agt  ttg gaa aat           6215
Tyr Val Trp Ser  Lys Asn Pro Tyr  Glu Leu Leu Ser  Leu Glu Asn
        1095              1100              1105 ata aaa agt ttg  acc att gat aaa  tgt cca aga ctt  aga aga gaa           6260
Ile Lys Ser Leu  Thr Ile Asp Lys  Cys Pro Arg Leu  Arg Arg Glu
        1110              1115              1120 tac tca gtc aaa  att cta aag caa  ctt gaa gat gta  agc ata gat           6305
Tyr Ser Val Lys  Ile Leu Lys Gln  Leu Glu Asp Val  Ser Ile Asp
        1125              1130              1135 atc aaa caa ttg  atg aag gtt att  gag aag gaa aag  tca gca cat           6350
Ile Lys Gln Leu  Met Lys Val Ile  Glu Lys Glu Lys  Ser Ala His
        1140              1145              1150 cat aat atg ttg  gaa tca aag caa  tgg gag act tca  tct tct tct           6395
His Asn Met Leu  Glu Ser Lys Gln  Trp Glu Thr Ser  Ser Ser Ser
        1155              1160              1165 aag gtacgtatat attctacaag aaaacatgtt tgttcaattt aattttcaga              6448
Lys aaataaattg ttttcaagaa ttagttgaac agaattggtt ctgttagttg aacagagttt        6508
taaagaaaac aaattattat gtttgttcta gaaacctatg gaaattagtg ttattagggg        6568
ttaattattt acctgaatta aaaaagaata agcaagtaaa ccgcttaatt ttaatatgtt        6628
tatcaataga aattaggatc cgtttggatt gacttgaatg atatgttttc ctggaaagaa        6688
actcattttt gtttgaactc atttttatga aaattggcta aaatatattt aaaaaattag        6748
gtggctttca aatattcaat ttttttttta aaataactta ttttttgaat taaacactcc        6808
aaaatgtaat tcaaaaacac ccctaagtta attagatata taattaatac ataaattaat        6868
taattttatt tagttgagtt aaattagttt taatgcaaac aataatatat ttttatagcc        6928
aatatacaag aatgaaagta agaaaagaag acaaaaaaaa atgatatgtt aattagaatt        6988
ttacataaag aatgatctga ttaaaagcta atctctatcg atatagtttt ttaattatat        7048
taaatatagt aagtagtcca ttataataat tgaattttt tgtaccaaat taattaaact        7108
aattcttttt actaattatt gaatatttaa gatattttg gctaattaat taataatttg        7168
tgtgcaaata taagttatta ttgcatttat ttaatagatt ttgatcatca g gat ggg        7225
                                                         Asp Gly gtt cta cgg ctg gga gat ggt tct aag ttg ttt cca aat ctt aaa             7270
Val Leu Arg Leu  Gly Asp Gly Ser  Lys Leu Phe Pro  Asn Leu Lys
1170             1175              1180 agt ttg aag cta tat ggt ttt gtt gat tat aac tca acc cat tta             7315
Ser Leu Lys Leu  Tyr Gly Phe Val  Asp Tyr Asn Ser  Thr His Leu
1185             1190              1195 cca atg gaa atg ttg caa atc tta ttc caa ctt gta gtc ttt gaa             7360
Pro Met Glu Met  Leu Gln Ile Leu  Phe Gln Leu Val  Val Phe Glu
```

-continued

```
            1200                   1205                  1210
ttg  gaa  gga  gca  ttt  ctt  gaa  gaa  att  ttc  ccc  agc  aac  ata  ctg    7405
Leu  Glu  Gly  Ala  Phe  Leu  Glu  Glu  Ile  Phe  Pro  Ser  Asn  Ile  Leu
1215                1220                    1225 att  cca  agc  tat  atg  gtt  tta  aga  aga  tta  gct  cta  tct  aaa  cta    7450
Ile  Pro  Ser  Tyr  Met  Val  Leu  Arg  Arg  Leu  Ala  Leu  Ser  Lys  Leu
1230                1235                    1240 ccc  aag  ctt  aag  cat  ttg  tgg  agt  gaa  gaa  tgc  tca  caa  aac  aat    7495
Pro  Lys  Leu  Lys  His  Leu  Trp  Ser  Glu  Glu  Cys  Ser  Gln  Asn  Asn
1245                1250                    1255 atc  acc  tca  gtt  ctt  caa  cat  ttg  att  tct  cta  aga  att  tca  gaa    7540
Ile  Thr  Ser  Val  Leu  Gln  His  Leu  Ile  Ser  Leu  Arg  Ile  Ser  Glu
1260                1265                    1270 tgt  gga  aga  ttg  agt  agt  tta  ctg  tcg  tca  ata  gtg  tgt  ttt  aca    7585
Cys  Gly  Arg  Leu  Ser  Ser  Leu  Leu  Ser  Ser  Ile  Val  Cys  Phe  Thr
1275                1280                    1285 aac  ttg  aaa  cat  ctt  cgg  gtt  tat  aaa  tgt  gat  gga  cta  acc  cat    7630
Asn  Leu  Lys  His  Leu  Arg  Val  Tyr  Lys  Cys  Asp  Gly  Leu  Thr  His
1290                1295                    1300 ttg  ctg  aat  cct  tcg  gtg  gct  aca  acg  ctt  gtg  caa  ctt  gag  tct    7675
Leu  Leu  Asn  Pro  Ser  Val  Ala  Thr  Thr  Leu  Val  Gln  Leu  Glu  Ser
1305                1310                    1315 ttg  aca  ata  gaa  gaa  tgc  aaa  agg  atg  agt  agt  gta  att  gag  gga    7720
Leu  Thr  Ile  Glu  Glu  Cys  Lys  Arg  Met  Ser  Ser  Val  Ile  Glu  Gly
1320                1325                    1330 gga  tca  acc  gaa  gaa  gat  gga  aat  gat  gaa  atg  gtt  gta  ttc  aac    7765
Gly  Ser  Thr  Glu  Glu  Asp  Gly  Asn  Asp  Glu  Met  Val  Val  Phe  Asn
1335                1340                    1345 aac  cta  caa  cat  tta  tac  att  ttt  aat  tgt  tcc  aac  cta  aca  agc    7810
Asn  Leu  Gln  His  Leu  Tyr  Ile  Phe  Asn  Cys  Ser  Asn  Leu  Thr  Ser
1350                1355                    1360 ttt  tat  tgt  ggg  aga  tgc  att  att  aaa  ttt  cca  tgt  ttg  agg  caa    7855
Phe  Tyr  Cys  Gly  Arg  Cys  Ile  Ile  Lys  Phe  Pro  Cys  Leu  Arg  Gln
1365                1370                    1375 gta  gac  att  tgg  aac  tgt  tct  gaa  atg  aag  gtc  ttt  tcg  ctt  gga    7900
Val  Asp  Ile  Trp  Asn  Cys  Ser  Glu  Met  Lys  Val  Phe  Ser  Leu  Gly
1380                1385                    1390 att  gta  agc  aca  cct  cga  ttg  aaa  tat  gaa  aat  ttt  tct  tta  aag    7945
Ile  Val  Ser  Thr  Pro  Arg  Leu  Lys  Tyr  Glu  Asn  Phe  Ser  Leu  Lys
1395                1400                    1405 aat  gat  tac  gat  gat  gaa  cgg  tgt  cat  cca  aaa  tat  ccc  aaa  gat    7990
Asn  Asp  Tyr  Asp  Asp  Glu  Arg  Cys  His  Pro  Lys  Tyr  Pro  Lys  Asp
1410                1415                    1420 atg  ttg  gtg  gaa  gat  atg  aat  gtc  atc  acc  aga  gaa  tat  tgg  gag    8035
Met  Leu  Val  Glu  Asp  Met  Asn  Val  Ile  Thr  Arg  Glu  Tyr  Trp  Glu
1425                1430                    1435 gat  aat  gtt  gat  acc  gga  att  cca  aat  tta  ttt  gcc  gaa  cag          8077
Asp  Asn  Val  Asp  Thr  Gly  Ile  Pro  Asn  Leu  Phe  Ala  Glu  Gln
1440                1445                    1450 gtttgtatat ttaattacct tttcatattt ggtaataatt aattttttatt atttgtgtgt             8137 tagagtatga actttaatga atttatttaa ttaatgcag  agt  ttg  gag  gaa  aac           8191
                                            Ser  Leu  Glu  Glu  Asn
                                                      1455 cga  tct  gaa  aat  tct  tct  tct  tcg  aag  aat  aat  gtt  gag  aaa  gaa    8236
Arg  Ser  Glu  Asn  Ser  Ser  Ser  Ser  Lys  Asn  Asn  Val  Glu  Lys  Glu
       1460                1465                    1470 taa  ggaattatat ggatattgtt gtacactact taatatatca tttcatccac                    8289
aaggaaaagg tcagaatctt gaaatcctcc attctttttt atgagagaat atcatccaat              8349
```

```
gtcaaattga aaagtctcga tagatttgtt aaattaactt ttgatacaag tcataaaatg   8409
ttaattagta taataataat atatctgatc ccatcaaatt aattagaagt aacgacaaat   8469
ttaacttctg taatatcaat tcaatttgat gtctcaatca actgcataaa atttgatgtc   8529
acaaatttaa cttctgtaat gtgaatcttt tttttttttc cctttgcaca taaaaccaac   8589
aagttaaaat agatataaca aagaatttaa ttcacatata ataaattcat ccaatataat   8649
gttctttcac cttttctct ctttcacaaa actgtaataa taatatctac cacaaaaggt    8709
aaaccattaa tatgattctt caagaaggtt gtttatttgg tcaaattttc atgaaagtat   8769
taatacagtg tatgttttgc aaaggaagct gccaaatacc tacctcaatc ctagcagatg   8829
cgttctttgc aagttggctg tcaaagactt gaaccatatt ttcacaacct gtgccaattc   8889
gcaaatagcc tctgggtcaa actgcacgac aaaattggtg gaactttga tacaaacagt    8949 atcaaagccc tctgttggtc tcttggctcg ctgaaacaat caaacagaaa gaacatcatt   9009
ctctcgatgt aggtgtggat cttctttagt ccatttgggt ggaagaaac aataggattt    9069 tcatagacac agaaagaagc ttagtcacat ttgggaagat atcgaaactt tgattggacc   9129
atggtcgagt agaaacaaaa tgttcaaaga ctacaatcca acatcaatct ttaaacttta   9189
gagctttgtt agattaatgt ttgttgtata tggcttccct gtagccaaag aaatatacat   9249
tgtaacaatg gtttgatgaa atgataatga agtggtatgg tgtgtttcaa ttgcaaaaaa   9309
tatgattctt caagaaaggc cgagaggata agattgtgat cgtgccatgc gcttgggttg   9369
tgatttaatt acaaatatat tcatatagta tttggagcaa acagtccta attaattaaa    9429 tataatgcgt tattttattt ttctgaataa gttaaattta accactagaa atttttttac   9489
taagtgaaca ttttcatagc actttcataa tccccacttc attaaaatga atcaataaag   9549
ttcaaggaaa gtgtagaatg atgaatctaa aagaaacaaa aaacaaggta tataagttta   9609
aagcaacggt ggtagcactg taatgatccg agggagtaca catttttca taaattattt    9669 tattatcatc aatagaagaa ttcgaatttc ttttatcttt taattgataa tataatttca   9729
taattagcta taagtggatt tttcaaatga ttggatccac atacatatca acttcgatca   9789
aattattaaa ggtataattt taaatcacta agaagaaaag gattgatggt gggccttatg   9849
ctattataca ctttgagtac cctctcggcc tcaacaagat tcccaagttc aataattgaa   9909
actttgaaaa atgtgtgcaa tcacatgtat tcaatttcta tgtcggtatc acatattttc   9969
atgtttccat acgtttaatt tccatataaa agtgaatcca taattttatt atattgcgaa   10029
aaaatctacc aaacatggaa attagctatg aaaatattag taatataaat aatggatatg   10089
ttgacttatt tgaaaaaaat taaaaaaata ttcatttatg ggtttaaatt tattttttaaa  10149 ttttttgttt ttatatatta ttttaaaaat atatattgaa attaatattt tattgatatt   10209
atatcatcaa aatttttgta aaattaagat cattaatata acgccccaga cccaagattt   10269
ggaattcgga tccctgacat tcttttgcat ccactgtgat ctgataacat catctttact   10329
tgtcttaaat tattagactg aaagttctct ccacaaaaca ataggagtca tttcaacata   10389
ctttgtcctc actcacagca tccctatcac tcataattaa tgtaaaattt tattatattt   10449
gtaaatatgt tttggtgtac tttgccatat attaaaacat actactaaac aaaacgaaat   10509
gattaaaaag gaagggaagg tattaaaaat tataaatttt aagaaaggaa agaagaaga    10569 aggaaaaaaa aaaaaaaaag agaatgatga gtgagaggca ccaagtgagg acatatacta   10629
ctctttgagt acataaccta atggttaaga aaaaaaaaa tctcatatca aattcaaagt    10689
```

-continued

```
gccatgctat tattacttaa tattttatat ggaagttaaa taaattgtta gagagaagtc    10749
ttgttttctg tctgtttgtt aactcatttt tgtaattaat gtttaatttg atcattgtca    10809
ttccaattaa ttgtaacata attttctgcc caatttatct cttttgcttt cgttttttgtt   10869 tagataccct actcggctac tcctcaactt ttcctcattt cattttcagt tgg           10922

<210> SEQ ID NO 2
<211> LENGTH: 5085
<212> TYPE: DNA
<213> ORGANISM: Cucumis melo

<400> SEQUENCE: 2
attattatgg ttcattcctc gtggtttttt agctcttcaa gtattttgt aggttttgat       60 cctttttcaag ctcaagaaca gaggataata atggacatcc ttatttcagt cactgcaaaa    120
attgccgaat acactgttga gcctgttgga cgccaacttg gttatgtatt tttcattcgt     180
tccaactttc aaaaacttaa gactcaagta gaaaagctga agattacaag agagtctgtg    240
caacacaaga tccatagtgc aagaagaaat gctgaagaca taaaacctgc cgttgaggaa    300
tggttgaaaa aggtcgatga ctttgtccga gaatctgacg agatattagc caatgaaggt    360
ggacatggtg gactctgttc cacctatttg gtccaacgac acaagttaag tagaaaagca    420
agcaaaatgg tagatgaggt tcttgagatg aaaaatgagg gggaaagttt tgatatggta    480
tcctataaaa gtgttatccc atcagttgat tgttcacttc caaaagtgcc tgactttctt    540
gactttgagt caagaaagtc gattatgaaa caaatcatgg atgcactatc tgatggtaat    600
gtccatagga ttggagtata tgggatgggg ggtgttggca aaacaatgct agtgaaggat    660 atttaagaa aaattgtgga gagtaagaag cctttttgatg aggtggtaac atccacgatc    720
agccaaacac cagattttag aagtatccaa ggacaactag ctgacaagct aggtttgaaa    780
ttcgaacaag aaacaataga aggaagggct actattctac gaaagaggtt aaagatggag    840
agaagtatcc tagttgtgtt ggatgatgtt tgggagtata ttgatttgga aactatagga    900
attccaagtg ttgaagatca tacggggtgc aagatcttgt ttaccactag gattaaacat    960
ttgatctcaa atcaaatgtg cgccaataaa attttgaga taaaagtttt aggaaaagat    1020
gagtcatgga atttatttaa ggcaatggca ggtgacattg ttgatgcaag tgatttgaag    1080
cctatagcca ttcgaattgt gagagaatgt gcaggtttgc ctattgctat tactactgtt    1140
gctaaggcat tacgaaataa accttccgac atttggaatg atgccttaga tcagcttaaa    1200
actgttgatg tgggtatggc aaacattgga gaaatgaaa agaaagtgta tttgtcacta    1260
aaactgagtt acgattgctt gggatatgaa gaggtgaagt tattattctt gttatgcagc    1320
atgtttccag aagactttag cattgacgtg aagggttgc atgtatatgc catgggcatg    1380
ggattcttac atggtgttga tactgtggta aaaggacgac gtaggataaa aaaattggtt    1440
gatgatctta tcttcttc tttgcttcaa caatattctg agtatgggtg caattatgtg    1500
aaaatgcatg atatggttcg tgatgtagcc ctattaattg catctaagaa tgaacacgta    1560
cgtacattga gctatgtgaa aagatcgaat gaagaatggg aagaagagaa actattgggt    1620
aatcataccg cagtgttcat tgatggttta cattatcctc tcccgaagtt aacgttaccc    1680
aaagttcaat tattaaggtt agttgcaaaa tattgttggg aacataataa gcgtgtgtcg    1740
gtggtagaaa cttttttttga agaaatgaaa gagctcaaag gtttagtagt agaaaacgta    1800
aatatatcat tgatgcaacg accatctgat gtttactcct tagcaaacat cagagtatta    1860
cgtttggaaa gatgtcaatt attagggagc atagattgga ttggtgaatt aaaaaagctt    1920
```

```
gaaattcttg attttagtga atctaacatc acacaaattc ctacaaccat gagccaattg    1980
acacagctaa aagtgttgaa tttatcttct tgtgaacaac ttgaggtaat tccaccaaat    2040
attctttcaa agttgacaaa attggaagaa ttagatctgg aaactttga tggatgggaa     2100 ggagaagaat ggtatgaagg aaggaaaaat gctagccttt ctgaactcaa gtgcttgcga    2160
cacctttatg ctttaaactt aaccattcaa gatgaagaaa ttatgccaga aaacttgttc    2220
ttagttggga agttgaagct tcaaaaattc aacatttgta ttggttgcga aagcaaatta    2280
aagtatactt ttgcatacaa gaacagaatc aaaaacttca ttggaatcaa gatggaatca    2340
ggaaggtgct tggatgattg gataaaaaat ttgttaaaga ggtcggacaa tgtgcttttg    2400
gaaggatcag tttgttcaaa ggttctccac tcagaattgg taggtgccaa taacttcgta    2460
tcacttccta atttggagaa gttggaaatt gtgaatgcaa agagtttgaa gatgatatgg    2520
agcaataacg tgccaattct taattccttt tccaaactcg aggaaataaa aatttattca    2580
tgcaacaatc ttcaaaaagt attatttcct ccaaatatga tggacattct cacatgcctt    2640
aaagtcttag agatcaaaaa ttgtgatttg ttggaaggga tatttgaagc gcaagagcca    2700
attagtgttg ttgagagcaa taatttaccc attcttaatt ccttttccaa actcgaggaa    2760
ataagaattt ggtcatgcaa caatcttcaa aaagtattat ttccttcaaa tatgatgggc    2820
attcttccat gccttaaagt cttagatatt agaggttgtg aattgttgga agggatattt    2880
gaagtgcaag agccaattag tgttgttgag agcaatagtg tacccattct taattccttt    2940
tccaaactcg agaaaataag aatttggtca tgcaacaatc ttcaaaaaat attatttcct    3000
tcaaatatga tggcattct tacatgcctt aaagtcttag agatcagaga ttgtgaattg     3060
ttggaaggga tatttgaagt gcaagagcca attagtgttg ttgagagcaa taatttaccc    3120
attcttaatt ccttttccaa actcgaggaa ataagaattg ggtcatgcaa caatcttcaa    3180
aaagtattat ttcctccaaa tatgatgggc attcttacat gccttaaagt cttagagatt    3240
agacattgta atttgttgga agggatattt gaagtgcaag agccaattag tattgttgaa    3300
gcgagtccta tcttgctcca aaatttatct tcgttgatgt tatgtaatct tccaaacctt    3360
gagtacgtgt ggagcaaaaa tccttatgaa cttctgagtt tggaaaatat aaaaagtttg    3420
accattgata aatgtccaag acttagaaga gaatactcag tcaaaattct aaagcaactt    3480
gaagatgtaa gcatagatat caaacaattg atgaaggtta ttgagaagga aaagtcagca    3540
catcataata tgttggaatc aaagcaatgg gagacttcat cttcttctaa ggatggggtt    3600
ctacggctgg gagatggttc taagttgttt ccaaatctta aaagtttgaa gctatatggt    3660
tttgttgatt ataactcaac ccatttacca atggaaatgt tgcaaatctt attccaactt    3720
gtagtctttg aattggaagg agcatttctt gaagaaattt tccccagcaa catactgatt    3780
ccaagctata tggttttaag aagattagct ctatctaaac tacccaagct taagcatttg    3840
tggagtgaag aatgctcaca aaacaatatc acctcagttc ttcaacattt gatttctcta    3900
agaatttcag aatgtggaag attgagtagt ttactgtcgt caatagtgtg ttttacaaac    3960
ttgaaacatc ttcgggttta aaatgtgat ggactaaccc atttgctgaa tccttcggtg     4020
gctacaacgc ttgtgcaact tgagtctttg acaatagaag aatgcaaaag gatgagtagt    4080
gtaattgagg gaggatcaac cgaagaagat ggaaatgatg aaatggttgt attcaacaac    4140
ctacaacatt tatacatttt taattgttcc aacctaacaa gcttttattg tgggagatgc    4200
attattaaat ttccatgttt gaggcaagta gacatttgga actgttctga aatgaaggtc    4260
```

-continued

```
ttttcgcttg gaattgtaag cacacctcga ttgaaatatg aaatttttc tttaaagaat    4320 gattacgatg atgaacggtg tcatccaaaa tatcccaaag atatgttggt ggaagatatg    4380
aatgtcatca ccagagaata ttgggaggat aatgttgata ccggaattcc aaatttattt    4440
gccgaacaga gtttggagga aaaccgatct gaaaattctt cttcttcgaa gaataatgtt    4500
gagaaagaat aaggaattat atggatattg ttgtacacta cttaatatat catttcatcc    4560
acaaggaaaa ggaagctgcc aaatacctac ctcaatccta gcagatgcgt tctttgcaag    4620
ttggctgtca aagacttgaa ccatattttc acaacctgtg ccaattcgca aatagcctct    4680
gggtcaaact gcacgacaaa attggtgaaa actttgatac aaacagtatc aaagccctct    4740
gttggtctct tggctcgctg aaacaatcaa acagaaagaa catcattctc tcgatgtagg    4800
tgtggatctt ctttagtcca tttggtggaa agaaacaat aggattttca tagacacaga    4860
aagaagctta gtcacatttg gaagatatc gaaactttga ttggaccatg gtcgagtaga    4920
aacaaaatgt tcaaagacta caatccaaca tcaatcttta aactttagag ctttgttaga    4980
ttaatgtttg ttgtatatgg cttccctgta gccaagaaaa tatacattgt aacaatggtt    5040
tgatgaaatg ataatgaagt ggtatggtgt gtttcaattg caaaa                     5085
```

<210> SEQ ID NO 3
<211> LENGTH: 1473
<212> TYPE: PRT
<213> ORGANISM: Cucumis melo

<400> SEQUENCE: 3

```
Met Asp Ile Leu Ile Ser Val Thr Ala Lys Ile Ala Glu Tyr Thr Val
1               5                   10                  15

Glu Pro Val Gly Arg Gln Leu Gly Tyr Val Phe Phe Ile Arg Ser Asn
            20                  25                  30

Phe Gln Lys Leu Lys Thr Gln Val Glu Lys Leu Lys Ile Thr Arg Glu
        35                  40                  45

Ser Val Gln His Lys Ile His Ser Ala Arg Arg Asn Ala Glu Asp Ile
    50                  55                  60

Lys Pro Ala Val Glu Glu Trp Leu Lys Lys Val Asp Asp Phe Val Arg
65                  70                  75                  80

Glu Ser Asp Glu Ile Leu Ala Asn Glu Gly His Gly Gly Leu Cys
                85                  90                  95

Ser Thr Tyr Leu Val Gln Arg His Lys Leu Ser Arg Lys Ala Ser Lys
            100                 105                 110

Met Val Asp Glu Val Leu Glu Met Lys Asn Glu Gly Glu Ser Phe Asp
        115                 120                 125

Met Val Ser Tyr Lys Ser Val Ile Pro Ser Val Asp Cys Ser Leu Pro
    130                 135                 140

Lys Val Pro Asp Phe Leu Asp Phe Glu Ser Arg Lys Ser Ile Met Glu
145                 150                 155                 160

Gln Ile Met Asp Ala Leu Ser Asp Gly Asn Val His Arg Ile Gly Val
                165                 170                 175

Tyr Gly Met Gly Gly Val Gly Lys Thr Met Leu Val Lys Asp Ile Leu
            180                 185                 190

Arg Lys Ile Val Glu Ser Lys Lys Pro Phe Asp Glu Val Val Thr Ser
        195                 200                 205

Thr Ile Ser Gln Thr Pro Asp Phe Arg Ser Ile Gln Gly Gln Leu Ala
    210                 215                 220

Asp Lys Leu Gly Leu Lys Phe Glu Gln Glu Thr Ile Glu Gly Arg Ala
```

```
              225                 230                 235                 240
Thr Ile Leu Arg Lys Arg Leu Lys Met Glu Arg Ser Ile Leu Val Val
                245                 250                 255
Leu Asp Asp Val Trp Glu Tyr Ile Asp Leu Glu Thr Ile Gly Ile Pro
                260                 265                 270
Ser Val Glu Asp His Thr Gly Cys Lys Ile Leu Phe Thr Thr Arg Ile
                275                 280                 285
Lys His Leu Ile Ser Asn Gln Met Cys Ala Asn Lys Ile Phe Glu Ile
                290                 295                 300
Lys Val Leu Gly Lys Asp Glu Ser Trp Asn Leu Phe Lys Ala Met Ala
305                 310                 315                 320
Gly Asp Ile Val Asp Ala Ser Asp Leu Lys Pro Ile Ala Ile Arg Ile
                325                 330                 335
Val Arg Glu Cys Ala Gly Leu Pro Ile Ala Ile Thr Thr Val Ala Lys
                340                 345                 350
Ala Leu Arg Asn Lys Pro Ser Asp Ile Trp Asn Asp Ala Leu Asp Gln
                355                 360                 365
Leu Lys Thr Val Asp Val Gly Met Ala Asn Ile Gly Glu Met Glu Lys
                370                 375                 380
Lys Val Tyr Leu Ser Leu Lys Leu Ser Tyr Asp Cys Leu Gly Tyr Glu
385                 390                 395                 400
Glu Val Lys Leu Leu Phe Leu Leu Cys Ser Met Phe Pro Glu Asp Phe
                405                 410                 415
Ser Ile Asp Val Glu Gly Leu His Val Tyr Ala Met Gly Met Gly Phe
                420                 425                 430
Leu His Gly Val Asp Thr Val Val Lys Gly Arg Arg Ile Lys Lys
                435                 440                 445
Leu Val Asp Asp Leu Ile Ser Ser Leu Leu Gln Gln Tyr Ser Glu
                450                 455                 460
Tyr Gly Cys Asn Tyr Val Lys Met His Asp Met Val Arg Asp Val Ala
465                 470                 475                 480
Leu Leu Ile Ala Ser Lys Asn Glu His Val Arg Thr Leu Ser Tyr Val
                485                 490                 495
Lys Arg Ser Asn Glu Glu Trp Glu Glu Glu Lys Leu Leu Gly Asn His
                500                 505                 510
Thr Ala Val Phe Ile Asp Gly Leu His Tyr Pro Leu Pro Lys Leu Thr
                515                 520                 525
Leu Pro Lys Val Gln Leu Leu Arg Leu Val Ala Lys Tyr Cys Trp Glu
                530                 535                 540
His Asn Lys Arg Val Ser Val Val Glu Thr Phe Phe Glu Glu Met Lys
545                 550                 555                 560
Glu Leu Lys Gly Leu Val Val Glu Asn Val Asn Ile Ser Leu Met Gln
                565                 570                 575
Arg Pro Ser Asp Val Tyr Ser Leu Ala Asn Ile Arg Val Leu Arg Leu
                580                 585                 590
Glu Arg Cys Gln Leu Leu Gly Ser Ile Asp Trp Ile Gly Glu Leu Lys
                595                 600                 605
Lys Leu Glu Ile Leu Asp Phe Ser Glu Ser Asn Ile Thr Gln Ile Pro
                610                 615                 620
Thr Thr Met Ser Gln Leu Thr Gln Leu Lys Val Leu Asn Leu Ser Ser
625                 630                 635                 640
Cys Glu Gln Leu Glu Val Ile Pro Pro Asn Ile Leu Ser Lys Leu Thr
                645                 650                 655
```

```
Lys Leu Glu Glu Leu Asp Leu Glu Thr Phe Asp Gly Trp Glu Gly Glu
        660                 665                 670

Glu Trp Tyr Glu Gly Arg Lys Asn Ala Ser Leu Ser Glu Leu Lys Cys
        675                 680                 685

Leu Arg His Leu Tyr Ala Leu Asn Leu Thr Ile Gln Asp Glu Glu Ile
        690                 695                 700

Met Pro Glu Asn Leu Phe Leu Val Gly Lys Leu Lys Leu Gln Lys Phe
705                 710                 715                 720

Asn Ile Cys Ile Gly Cys Glu Ser Lys Leu Lys Tyr Thr Phe Ala Tyr
                725                 730                 735

Lys Asn Arg Ile Lys Asn Phe Ile Gly Ile Lys Met Glu Ser Gly Arg
        740                 745                 750

Cys Leu Asp Asp Trp Ile Lys Asn Leu Leu Lys Arg Ser Asp Asn Val
        755                 760                 765

Leu Leu Glu Gly Ser Val Cys Ser Lys Val Leu His Ser Glu Leu Val
        770                 775                 780

Gly Ala Asn Asn Phe Val Ser Leu Pro Asn Leu Glu Lys Leu Glu Ile
785                 790                 795                 800

Val Asn Ala Lys Ser Leu Lys Met Ile Trp Ser Asn Val Pro Ile
                805                 810                 815

Leu Asn Ser Phe Ser Lys Leu Glu Glu Ile Lys Ile Tyr Ser Cys Asn
                820                 825                 830

Asn Leu Gln Lys Val Leu Phe Pro Pro Asn Met Met Asp Ile Leu Thr
        835                 840                 845

Cys Leu Lys Val Leu Glu Ile Lys Asn Cys Asp Leu Leu Glu Gly Ile
        850                 855                 860

Phe Glu Ala Gln Glu Pro Ile Ser Val Val Glu Ser Asn Asn Leu Pro
865                 870                 875                 880

Ile Leu Asn Ser Phe Ser Lys Leu Glu Glu Ile Arg Ile Trp Ser Cys
                885                 890                 895

Asn Asn Leu Gln Lys Val Leu Phe Pro Ser Asn Met Met Gly Ile Leu
                900                 905                 910

Pro Cys Leu Lys Val Leu Asp Ile Arg Gly Cys Glu Leu Leu Glu Gly
        915                 920                 925

Ile Phe Glu Val Gln Glu Pro Ile Ser Val Val Glu Ser Asn Ser Val
        930                 935                 940

Pro Ile Leu Asn Ser Phe Ser Lys Leu Glu Lys Ile Arg Ile Trp Ser
945                 950                 955                 960

Cys Asn Asn Leu Gln Lys Ile Leu Phe Pro Ser Asn Met Met Gly Ile
                965                 970                 975

Leu Thr Cys Leu Lys Val Leu Glu Ile Arg Asp Cys Glu Leu Leu Glu
        980                 985                 990

Gly Ile Phe Glu Val Gln Glu Pro Ile Ser Val Val Glu Ser Asn Asn
        995                 1000                1005

Leu Pro Ile Leu Asn Ser Phe Ser Lys Leu Glu Glu Ile Arg Ile
        1010                1015                1020

Gly Ser Cys Asn Asn Leu Gln Lys Val Leu Phe Pro Pro Asn Met
        1025                1030                1035

Met Gly Ile Leu Thr Cys Leu Lys Val Leu Glu Ile Arg His Cys
        1040                1045                1050

Asn Leu Leu Glu Gly Ile Phe Glu Val Gln Glu Pro Ile Ser Ile
        1055                1060                1065
```

-continued

Val Glu Ala Ser Pro Ile Leu Leu Gln Asn Leu Ser Ser Leu Met
1070                1075                1080

Leu Cys Asn Leu Pro Asn Leu Glu Tyr Val Trp Ser Lys Asn Pro
1085                1090                1095

Tyr Glu Leu Leu Ser Leu Glu Asn Ile Lys Ser Leu Thr Ile Asp
1100                1105                1110

Lys Cys Pro Arg Leu Arg Arg Glu Tyr Ser Val Lys Ile Leu Lys
1115                1120                1125

Gln Leu Glu Asp Val Ser Ile Asp Ile Lys Gln Leu Met Lys Val
1130                1135                1140

Ile Glu Lys Glu Lys Ser Ala His His Asn Met Leu Glu Ser Lys
1145                1150                1155

Gln Trp Glu Thr Ser Ser Ser Lys Asp Gly Val Leu Arg Leu
1160                1165                1170

Gly Asp Gly Ser Lys Leu Phe Pro Asn Leu Lys Ser Leu Lys Leu
1175                1180                1185

Tyr Gly Phe Val Asp Tyr Asn Ser Thr His Leu Pro Met Glu Met
1190                1195                1200

Leu Gln Ile Leu Phe Gln Leu Val Val Phe Glu Leu Glu Gly Ala
1205                1210                1215

Phe Leu Glu Glu Ile Phe Pro Ser Asn Ile Leu Ile Pro Ser Tyr
1220                1225                1230

Met Val Leu Arg Arg Leu Ala Leu Ser Lys Leu Pro Lys Leu Lys
1235                1240                1245

His Leu Trp Ser Glu Glu Cys Ser Gln Asn Asn Ile Thr Ser Val
1250                1255                1260

Leu Gln His Leu Ile Ser Leu Arg Ile Ser Glu Cys Gly Arg Leu
1265                1270                1275

Ser Ser Leu Leu Ser Ser Ile Val Cys Phe Thr Asn Leu Lys His
1280                1285                1290

Leu Arg Val Tyr Lys Cys Asp Gly Leu Thr His Leu Leu Asn Pro
1295                1300                1305

Ser Val Ala Thr Thr Leu Val Gln Leu Glu Ser Leu Thr Ile Glu
1310                1315                1320

Glu Cys Lys Arg Met Ser Ser Val Ile Glu Gly Gly Ser Thr Glu
1325                1330                1335

Glu Asp Gly Asn Asp Glu Met Val Val Phe Asn Asn Leu Gln His
1340                1345                1350

Leu Tyr Ile Phe Asn Cys Ser Asn Leu Thr Ser Phe Tyr Cys Gly
1355                1360                1365

Arg Cys Ile Ile Lys Phe Pro Cys Leu Arg Gln Val Asp Ile Trp
1370                1375                1380

Asn Cys Ser Glu Met Lys Val Phe Ser Leu Gly Ile Val Ser Thr
1385                1390                1395

Pro Arg Leu Lys Tyr Glu Asn Phe Ser Leu Lys Asn Asp Tyr Asp
1400                1405                1410

Asp Glu Arg Cys His Pro Lys Tyr Pro Lys Asp Met Leu Val Glu
1415                1420                1425

Asp Met Asn Val Ile Thr Arg Glu Tyr Trp Glu Asp Asn Val Asp
1430                1435                1440

Thr Gly Ile Pro Asn Leu Phe Ala Glu Gln Ser Leu Glu Glu Asn
1445                1450                1455

Arg Ser Glu Asn Ser Ser Ser Ser Lys Asn Asn Val Glu Lys Glu

<210> SEQ ID NO 4
<211> LENGTH: 10773
<212> TYPE: DNA
<213> ORGANISM: Cucumis melo

<400> SEQUENCE: 4

| | | | | | |
|---|---|---|---|---|---|
| tcaacctccc | aattaccata | agtgcaaaat | tcttttgtcg | tccatattat | tgttaatgaa | 60 |
| gaacaaagat | gaatttaacc | aatcaccata | cattttattt | agatcgtatg | caacattttc | 120 |
| tttttcattt | ctagcctaaa | tccctcatat | tttcccctaa | aattcctctg | tttttctctt | 180 |
| cttcttctaa | ttcttgatct | ctctctctct | cttttggtt | tcttcttcta | actcttctct | 240 |
| cttcctcgca | aatccaagaa | aaagaaccat | agaatagttt | caagattttt | ttcaggggaa | 300 |
| gggggttgg | attttaattt | tcaaagtggg | ttattaattt | gttctattta | tgttttgtt | 360 |
| aatgattatt | agatgacgaa | gttgttttgg | gctacctaaa | gtcgaatctt | caaagctgta | 420 |
| agttttgtta | ttaagagtgg | atgagaaaga | aacttccagg | caaatttcca | atgatttta | 480 |
| cgcttacaca | tactgatatt | accttcttaa | cttactcttg | ccatttctca | ctctattaac | 540 |
| aacaaaatga | gtgtatgtaa | gtgataatat | tggttggacg | aaaaagaaaa | aaaaaaaaa | 600 |
| aggttctagg | aaacaaaaag | aaaaacgaaa | aaggcaagaa | atggaaaagg | aaacgttgtg | 660 |
| tatgatgatt | aaaatgtacg | ttgatagcta | aattcaactt | tgttcttcat | tagcaacaac | 720 |
| aagggacaac | aaaatgaaaa | tttcagcaca | gttatggagg | gttgaagaag | aaggtgacga | 780 |
| gagagatgcc | acatcataaa | aaattaatat | tataatcatt | tttgtcacat | tagttttctg | 840 |
| attacttata | tttaacctac | acatcatttt | gccgttactc | aactaacgat | caatatgacc | 900 |
| tttaaagctc | gatgattaaa | atgtttattt | tgaactttca | gggactatat | aaatgtatat | 960 |
| atatcaactt | caaatcttag | cggtcaaaag | tgcattttgt | tttagtttaa | agaccgaga | 1020 |
| tgtgaccatt | aataatgcct | acacacacat | atccccgtac | tcacacatgc | agtgagtttt | 1080 |
| ttatgttttt | tttacacaca | ttagacagca | aattgaattc | ctaattccat | tccctaagac | 1140 |
| aagtttctaa | tgacttatac | aattcacata | ggcatgcatg | cagaacaagc | gaaaaacgac | 1200 |
| gaatttacct | taagaaaatg | gcccaaccaa | ccacttacac | aatctcaggc | ataccattcc | 1260 |
| ccgggatgaa | agaattttc | ctgtaattca | ttcgatctca | ggcatacaat | gcatcgagaa | 1320 |
| gacgcaaaat | gaaagacaaa | agtatagaac | aacacaatcc | tgtacttcat | tttaaacgat | 1380 |
| agttttcaaa | tttaacgatc | gtgtagatca | tgatacacga | tctcgagcct | tagtggcacc | 1440 |
| gagatggccc | gagatgaaag | acctctacct | ttagttattc | gatctcgagc | cttaattgaa | 1500 |
| tcgagatgac | ccaagattaa | tagatcggaa | agaagatata | tatcgtaagg | gcatatatga | 1560 |
| aattatgaa | aatacgatca | tgtgtcataa | acttttctta | ttttgttata | tagaccgtaa | 1620 |
| atattataga | ttttggttac | atttgtgtaa | attactctat | tttttttag | taaaacaaat | 1680 |
| gaattaaatt | aaaaaaaaaa | ttattaagag | ttgaagtaat | tgggtgtttt | ctaaaagatt | 1740 |
| gaaataaata | cctttattaa | ctttgcaaat | atattttcaa | agaggctaac | aaatcaaata | 1800 |
| tattttctaa | aaaatcaca | ttgcgttggg | gataaggtaa | gagtaatgga | aaatgaaag | 1860 |
| gttgtgaaca | attcgtactc | ttacttatga | gatttgacag | aacaaatatt | ttcaaatac | 1920 |
| tcttttacg | ttttcttttt | taaaattaaa | taacaaatac | ttttccactg | cttttctttt | 1980 |
| cttccattga | ctcctcaact | aataattttg | gtcttcccat | tattatcttc | ttcttcttca | 2040 |
| tttttctctg | cactgtctct | tctccatttc | aacatcttct | tatatcttca | ttcaggttaa | 2100 |

-continued

```
atatttcatc ccttaccatt tttatttaca ttttccatct gatcatttct atacttataa    2160
actcgataat ttgtttagac tttctttaga tagtttttac tcggtgatct gtatgtgttc    2220
actcctactt ttctgttagg caaaatcttc aaaattatta tggttcattc ctcgtggttt    2280
tttagctctt caagtatttt tgtaggtttt gatccttttc aagctcaaga acagaggata    2340
ataatggaca tccttatttc agtcactgca aaaattgctg aatacactgt tgagcctgtt    2400
ggacgccaac ttggttatgt atttttcatt cgttccaact ttcaaaaact taagactcaa    2460
gtagaaaagc tgaagattac aagagagtct gtgcaacaca agatccatag tgcaagaaga    2520
aatgctgaag acataaaacc tgccgttgag gaatggttga aaaggtcga tgactttgtt    2580 cgagaatctg acgagatatt agccaatgaa ggtggacatg gtggactctg ttccacctat    2640
ttggtccaac gacacaagtt aagtagaaaa gcaagcaaaa tggtagatga ggttcttgag    2700
atgaaaaatg agggggaaag ttttgatatg gtatcctata aaagtgttat cccatcagtt    2760
gattgttcac ttccaaaagt gcctgacttt attgactttg agtcaagaaa gtcgattatg    2820
gaacaaatca tggatgcact atctgatggt aatgtcccata ggattggagt atatgggatg    2880
gggggtgttg gcaaaacaat gctagtgaag gatatttaa gaaaaattgt ggagagtaag    2940 aagcctttg atgaggtggt aacatccacg atcagccaaa caccagattt tagaagtatc    3000
caaggacaac tagctgacaa gctaggtttg aaattcgaac aagaaacaat agaaggaagg    3060
gctactattc tacgaaagag gttaaagatg gagagaagta tcctagttgt gttggatgat    3120
gtttgggagt atattgattt ggaaactata ggaattccaa gtgttgaaga tcatacgggg    3180
tgcaagatct tgtttaccac taggattaaa catttgatct caaatcaaat gtgcgccaat    3240 aaaattttg agataaaagt tttaggaaaa gatgagtcat ggaatttatt taaggcaatg    3300
gcaggtgaca ttgttgatgc aagtgatttg aagcctatag ccattcgaat tgtgagagaa    3360
tgtgcaggtt tgcctattgc tattactact gttgctaagg cattacgaaa taaaccttcc    3420
gacatttgga atgatgcctt agatcagctt aaaagtgttg atgtgggtat ggcaaacatt    3480
ggagaaatga aaaagaaagt gtatttgtca ctaaaactga gttacgattg cttgggatat    3540
gaagaggtga agttattatt cttgttatgc agcatgtttc cagaagactt tagcattgac    3600
gtggaagggt tgcatgtata tgccatgggc atgggattct tacatggtgt tgatactgtg    3660
gtaaaaggac gacgtaggat aaaaaaattg gttgatgatc ttatatcttc ttctttgctt    3720
caacaatatt ctgagtatgg gtgcaattat gtgaaaatgc atgatatggt tcgtgatgta    3780
gccctattaa ttgcatctaa gaatgaacac gtacgtacat tgagctatgt gaaaagatcg    3840
aatgaagaat gggaagaaga gaaactattg ggtaatcata ctgcagtgtt cattgatggt    3900
ttacattatc ctctcccgaa gttaacgtta cccaaagttc aattattaag gttagttgca    3960
caagattgtt gggaacataa taagcgtgtg tcggtggtag aaactttttt tgaagaaatg    4020
aaagagctca aaggtttagt attagcaaac gtaaatatat cattgatgca acgaacatct    4080
gatctttact ccttagcaaa catcagagta ttacgtttgc aaagctgtaa tttattaggg    4140
agcatagatt ggattggtga attaaaaaag cttgaaattc ttgattttat aggatctaac    4200
atcacacaaa ttcctacaac catgagccaa ttgacacaac tcaaagtgtt aaatttatct    4260
tcttgtcatc aactcaaggt aattccacca aatattcttt caaagttgac aaaactggaa    4320
gaattaagtc tggaaacttt tgatagatgg gaaggagaag aatggtatga aggaaggaaa    4380
aatgctagcc tttctgaact caagtgcttg cgacatcttt atgctttaaa tttaaccatt    4440
```

-continued

```
caagatgaag aaattatgcc aaaagatttg ttttttagctg aggagttgaa gcttcaaaaa   4500
ttcaacattt gtattggtta ccaaagcaaa ttaaagtata cttttggacc cacaaacaga   4560
atcaaaaact tcattgcaat caagatggaa tcaggaaggt gcttggataa ttggataaaa   4620
aatttgttaa agaggtcgga caatgtgttt ttggaaggat caatttgttc aaaggttctc   4680
cactcagaat tggtaggtgc aaatgacttc gtaaatttga agtatctcta cctttattat   4740
aattcaaaat ttcaacattt tatcaacgtt agcaatacca tcaacattga agaatcattt   4800
tttagtgaaa tggtaaattt catcaacaca ttttttctatg tttctatata cacatcaaaa  4860
tttataaatc acctgtttgt tcattttat tgttccttcc acaagttcct tctaacattt    4920
gtggttagta atgatagtag ggataagatt ctattcttct tgttttaga aggctcttct    4980 cttggtgtag agagactctt tcttgtttca tacattaatg ataatatata attttagact   5040
tctaaaatat ataaatgcat gtcaggtgat attccaagaa aatttaaaga agtttattag   5100
atatttccta tctaaggaag cagatttgaa gtaatcattt tacacaattt gttatggtaa   5160
ttttaaaaca ctatataaat tatatgttgt tagttagcat cagttgtgat gatatggtta   5220
attacgttgt cacaaactga acttttaagg acgtaaattt gtaggtatcg cttcctaatt   5280
tggagaagtt ggaaattgtg aatgcaaaga gtttgaagat gatatggagc aataacgtgc   5340
caattcttaa ttccttttcc aaactcgagg aaataaaaat ttattcatgc aacaatcttc   5400
aaaaagtatt atttcctcca aatatgatgg acattctcac atgccttaaa gtcttagaga   5460
tcaaaaattg tgatttgttg aagggggatat ttgaagcgca agagccaatt agtgttgttg   5520
agagcaataa tttacccatt cttaattcct tttccaaact cgaggaaata agaatttggt   5580
catgcaacaa tcttcaaaaa gtattatttc cttcaaatat gatgggcatt cttccatgcc   5640
ttaaagtctt agatattaga ggttgtgaat tgttggaagg gatatttgaa gtgcaagagc   5700
caattagtgt tgttgagagc aatagtgtac ccattcttaa ttccttttcc aaactcgaga   5760
aaataagaat ttggtcatgc aacaatcttc aaaaaatatt atttccttca aatatgatgg   5820
gcattcttac atgccttaaa gtcttagaga tcagagattg tgaattgttg aagggggatat  5880 ttgaagtgca agagccaatt agtgttgttg aagcgagtcc tatcgtgctc caaaatttaa   5940
ttaggttgga attatataat cttccaaacc ttgagtacgt gtggagcaaa aatccttgtg   6000
agcttctgag tttggaaaat ataaaaagtt tgaccattga ggaatgtcca agacttagaa   6060
gagaatactc agtcaaaatt ttcaagccac ttcaatatgt aagcatagat atcaaacaat   6120
tgatgaaggt tattgagaag gaaaagtcag cagatcataa tatgttggaa tcaaagcaat   6180
gggagacttc ttcttcttct aaggtacgta tatattctac aacaaaacat gtttgttcaa   6240
tttaattttc agaaaatata taaattgttt tcaagacctt agttgaacag aattggttct   6300
gttagttgaa cagagtttta aagaaaacaa attattatgt tgttctaga aacctatgga   6360 aattagtgtt attaggggtt aattatttac ctgaattaaa aaagaataag caacgtaaac   6420
cgcttaattt taatatgttt atcaatagaa attaggatcc gtttggattg acttgaatga   6480
tatgttttcc tggaaagaaa ctcattttg tttgaactca ttttatgaa aattggctaa     6540 aatacattta aaaaatgagg tggctttcaa atattcaatt ttttttttaa ataacttatt   6600
ttttgaatta aacactccaa aatgtaattc aaaaacaccc atataagtta attagatata   6660
taattaatac ataaattaat taattttatt tagtttgagt taaattagtt ttaatgcaaa   6720
caataatata tttttatagc caatatacaa gaatgaaagt aagaaaagaa gacaaaaaaa   6780
aaaaaaaaaa tgatatgtta attagaattt tacataaaga atgatctgat taaagctaat   6840
```

```
ctctatcgat atagttttt  aattatatta aatatagtaa gtagtccatt ataataattg   6900
aatttttttg taccaaatta attaaactaa ttcttttac  taattattga atatttaaga   6960
tattttggc  taattaatta ataatttgtg tggatatata agttattatt gcatttattt   7020
aatagatatt tttgatcatc aggatggggt tctacggctg ggagatggtt ctaagttgtt   7080
tccaaatctt aaaagtttga agctatatgg ttttgttgat tataactcaa cccatttacc   7140
aatggaaatg ttgcaaatct tattccaact taaacacttt gaattggaag gagcatttat   7200
tgaagaaatt ttccccagca atatactgat ttcaagctct atggatttac agagtttggc   7260
tctatataaa ctacccaagc ttaagcattt gtggagtgaa gaatgctcac gaaacaatat   7320
cacctcagtt cttcaacatt tgatttttct aagaatttca gattgtggaa gattgagtag   7380
tttaacttta gtgtcatcat tagtgtgttt tacaaacttg aaaagtcttg cggtttataa   7440
atgtgataga ctaacccatt tgctgaatcc ttcgatggct acaacgcttg tgcaacttca   7500
agatttgaca ataaaagaat gcaaagaatt gagaagtgta attgaggaag gatcaaccga   7560
agaagatgga aatgatgaaa tggttgtatt caacaaccta cgacatttat acatttttaa   7620
ttgttccaac ctaacaagct tttattgtgg gagatgcatc gttaaattcc catgtttgga   7680
aagagtattc attcaaaatt gtcctgaaat gaaggtcttt tcacttggaa ttgtaagcac   7740
gcctcgtttg aaatatgaaa agtttacttt aatgaatgat tacgatgata aatggtgtca   7800
tctgaaatat cccaaatata tgttggtgga agatatgaat gtcatcacca gagaatattg   7860
ggaggataat gttgataccg gaattccaaa tttatttgcc gaacaggttt gtatatttaa   7920
ttacctttc  atatttggta ataattaatt tttattattt gtgtgttaga gtatgaactt   7980
taatgaattt atttaattaa tgcagagttt ggaggaaaac cgatctgaaa attcttcttc   8040
ttcaaagaat aatgttgaga agaataagg  aattatatgg atattgttgt acactactta   8100
atatatcatt tcatccacaa ggaaaaggtc agactcttga aatcctccat tcttttttat   8160
gagagaatat catccaatgt caaattgaaa agtctcgata gatttgttaa attaattttt   8220
gatacaagtc ataaaatgtt aattagtata ataataatat atctgatccc atcaaattaa   8280
ttagaagtaa cgacaaattt aacttctgta atatcaattc aatttgatgt ctgcataaaa   8340
tttgatgtca caaatttaac ttctgtaatg tgaatctttt ttttttcctt tggacataaa   8400
accaacaagt taaatagat  ataacaatga atttaactca catataataa attcatccaa   8460
tataatgttc tttcacctt  ttctctcttt cacaaaactg taataataat atctaccaca   8520
aaaggtaaac aattaatatg attcttcaag aaggttgttt atttggtcaa attttcatga   8580
aagtattaat acagtgtatg ttttgcaaag gaagctgcca aataacctac tcaatcctag   8640
cagatgcgtt ctttgcaagc cggctgtcga agacttgaac catattttca caacctgtgc   8700
caattcgcaa atagcctctg ggtcaaactg cacgacaaaa ttggtggaaa ctttgataca   8760
aacagtatca aagccctctg ttggtctctt ggctcgctga acaatcaaa  cagaaagaac   8820
atcattctct cgatgtaggt gtggatcttc ttttgtccat ttgggtggaa agaaacaata   8880
ggatttcat  agacatagaa agaagcttag tcacatttgg gaagatatcg aaactttgat   8940
tggaccatgg tcgagtagaa acaaaatgtt caaagactac aatccaacat caatcttaa   9000
actttagagc tttgttagat taatgtttgt tgtatatggc ttccctgtgg ccaaagaaat   9060
atacattgta acaatggttt gatgaaatga taatgaagtg gtatggtgtt aaaatcacct   9120
ttatcactct gtgtttcaat ttcaaaaaat atgatttga  acattttcat agtactttca   9180
```

```
taatccccac ttcattgata tgaatcaata aagtctaagg aaagtggaga atgatgaatc      9240
aataaagttc atgaaaagtg cagaatgatg aatccaaaat gaaaaaaaaa caaggtcgat      9300
aagtttaaag taacggtggt agcattgtaa tgatcacaag ggagcacaca tttccccaca      9360
aattatttta ttatcattca cataacaatt caaatttctt atcttttaat tgatatataa      9420
tttcataatc agttataatt gaattttca aatgattgga tccatatatc aacgtcaatc       9480
aaatttttaa aggtaaagtt ttaaatttta aaatgtttaa ttagtataaa attgagaaat      9540
cacaaagaat aatttctctt cgatatatga gatttgaacc aaccttttg tttggagact       9600 aaatgtgcaa tataatttta tataatttta taaacatgca atattgaaa ttagattcaa       9660 aagtatgtat aataacaatt ttttttttt aaatcgtaaa tgtagcaaaa tttattagag       9720
tatttattaa taattgaaat gtgaaccata ttgcaaaaat tggttctatc actaatagat      9780
cataagagtc tttaaaaaaa atgattaaaa atagtttgtt gctaacaaac tttgttattt      9840
ttataatttt ttttaaata ttattatata cttaattaaa tgtctaaaat tattaccatt       9900
ataattaatg agatattaca cgtggattga tggtgggccc ttatatgcta ttatacactt      9960
tgcctaccct cttcccaaca agattcccaa gttaaataat tgaaacttt aacatctttc      10020 attacagttt gataaatgaa cgcaaacatg tgttgtttat tttactgaat tcgcgatcga     10080
ttattaaaat agacatgcag ttgatagcaa gcacacgaca ttaaataaaa atcatgaagt     10140
atttaatatc taatgaataa ccacataaac aatgaaacga aatataaac taagaaaagt      10200 caaatcatgt gcatattgat gaatctacac ttctcgatct cttcaaaacc tagcaaaatc     10260
aatagaattg aacattaaca atctaagcat acttgtgaat ataacaattt ttcggaaaaa     10320
taaaaattag gcaagagaat aagaacttgt gggtaaatta aattattgaa atggattgaa     10380
atctaaatgt tgtgtgattg ctactatctg atttcattt gatactgact gttttctatt     10440
acattatgat atactaattt tcatggatat tgattgcatg tcgtctaatt aatatctgat     10500
ttgtatattt gatatttgat tgttatttta tactatattt gttatttaat agttgtttga    10560
ttgctattta ttattgattg ttctaatgat atcaattgtt gtttgattaa gatctaataa     10620
tattggttgt caattataga aattgttata tgataatgat tgtaaaattg ttgatgatac     10680
tgattgttgt ttgaatataa caatcaatga tattgattgt tgtttgattg ctctcagatt     10740
actatctacg cctttaaact aatattaatt gat                                  10773

<210> SEQ ID NO 5
<211> LENGTH: 4919
<212> TYPE: DNA
<213> ORGANISM: Cucumis melo

<400> SEQUENCE: 5
attattatgg ttcattcctc gtggtttttt agctcttcaa gtattttgt aggttttgat        60 cctttcaag ctcaagaaca gaggataata atggacatcc ttatttcagt cactgcaaaa       120
attgctgaat acactgttga gcctgttgga cgccaacttg gttatgtatt tttcattcgt       180
tccaactttc aaaaacttaa gactcaagta gaaaagctga agattacaag agagtctgtg       240
caacacaaga tccatagtgc aagaagaaat gctgaagaca taaaacctgc cgttgaggaa       300
tggttgaaaa aggtcgatga ctttgttcga gaatctgacg agatattagc caatgaaggt       360
ggacatggtg gactctgttc cacctatttg gtccaacgac acaagttaag tagaaaagca       420
agcaaaatgg tagatgaggt tcttgagatg aaaaatgagg gggaaagttt tgatatggta       480
tcctataaaa gtgttatccc atcagttgat tgttcacttc caaaagtgcc tgactttatt       540
```

```
gactttgagt caagaaagtc gattatggaa caaatcatgg atgcactatc tgatggtaat    600
gtccatagga ttggagtata tgggatgggg ggtgttggca aaacaatgct agtgaaggat    660
attttaagaa aaattgtgga gagtaagaag ccttttgatg aggtggtaac atccacgatc    720
agccaaacac cagattttag aagtatccaa ggacaactag ctgacaagct aggtttgaaa    780
ttcgaacaag aaacaataga aggaagggct actattctac gaaagaggtt aaagatggag    840
agaagtatcc tagttgtgtt ggatgatgtt tgggagtata ttgatttgga aactatagga    900
attccaagtg ttgaagatca tacggggtgc aagatcttgt ttaccactag gattaaacat    960
ttgatctcaa atcaaatgtg cgccaataaa attttgaga taaaagtttt aggaaaagat     1020
gagtcatgga atttatttaa ggcaatggca ggtgacattg ttgatgcaag tgatttgaag    1080
cctatagcca ttcgaattgt gagagaatgt gcaggtttgc ctattgctat tactactgtt    1140
gctaaggcat tacgaaataa accttccgac atttggaatg atgccttaga tcagcttaaa    1200
agtgttgatg tgggtatggc aaacattgga gaaatggaaa agaaagtgta tttgtcacta    1260
aaactgagtt acgattgctt gggatatgaa gaggtgaagt tattattctt gttatgcagc    1320
atgtttccag aagactttag cattgacgtg aagggttgc atgtatatgc catgggcatg     1380
ggattcttac atggtgttga tactgtggta aaaggacgac gtaggataaa aaaattggtt    1440
gatgatctta tatcttcttc tttgcttcaa caatattctg agtatgggtg caattatgtg    1500
aaaatgcatg atatggttcg tgatgtagcc ctattaattg catctaagaa tgaacacgta    1560
cgtacattga gctatgtgaa aagatcgaat gaagaatggg aagaagagaa actattgggt    1620
aatcatactg cagtgttcat tgatggttta cattatcctc tcccgaagtt aacgttaccc    1680
aaagttcaat tattaaggtt agttgcacaa gattgttggg aacataataa gcgtgtgtcg    1740
gtggtagaaa cttttttga agaaatgaaa gagctcaaag gtttagtatt agcaaacgta     1800
aatatatcat tgatgcaacg aacatctgat ctttactcct tagcaaacat cagagtatta    1860
cgtttgcaaa gctgtaattt attagggagc atagattgga ttggtgaatt aaaaaagctt    1920
gaaattcttg atttatagg atctaacatc acacaaattc ctacaaccat gagccaattg     1980
acacaactca aagtgttaaa tttatcttct tgtcatcaac tcaaggtaat tccaccaaat    2040
attctttcaa agttgacaaa actggaagaa ttaagtctgg aaacttttga tagatgggaa    2100
ggagaagaat ggtatgaagg aaggaaaaat gctagccttt ctgaactcaa gtgcttgcga    2160
catctttatg ctttaaattt aaccattcaa gatgaagaaa ttatgccaaa agatttgttt    2220
ttagctgagg agttgaagct tcaaaaattc aacatttgta ttggttacca aagcaaatta    2280
aagtatactt ttggacccac aaacagaatc aaaaacttca ttgcaatcaa gatggaatca    2340
ggaaggtgct tggataattg gataaaaaat ttgttaaaga ggtcggacaa tgtgttttg     2400
gaaggatcaa tttgttcaaa ggttctccac tcagaattgg taggtgcaaa tgacttcgta    2460
tcgcttccta atttggagaa gttggaaatt gtgaatgcaa agagtttgaa gatgatatgg    2520
agcaataacg tgccaattct taattccttt tccaaactcg aggaaataaa aatttattca    2580
tgcaacaatc ttcaaaaagt attatttcct ccaaatatga tggacattct cacatgcctt    2640
aaagtcttag agatcaaaaa ttgtgatttg ttggaaggga tatttgaagc gcaagagcca    2700
attagtgttg ttgagagcaa taatttaccc attcttaatt ccttttccaa actcgaggaa    2760
ataagaattt ggtcatgcaa caatcttcaa aaagtattat tccttcaaa tatgatgggc     2820
attcttccat gccttaaagt cttagatatt agaggttgtg aattgttgga agggatattt    2880
```

```
gaagtgcaag agccaattag tgttgttgag agcaatagtg tacccattct taattccttt    2940
tccaaactcg agaaaataag aatttggtca tgcaacaatc ttcaaaaaat attatttcct    3000
tcaaatatga tgggcattct tacatgcctt aaagtcttag agatcagaga ttgtgaattg    3060
ttggaaggga tatttgaagt gcaagagcca attagtgttg ttgaagcgag tcctatcgtg    3120
ctccaaaatt taattaggtt ggaattatat aatcttccaa accttgagta cgtgtggagc    3180
aaaaatcctt gtgagcttct gagtttggaa aatataaaaa gtttgaccat tgaggaatgt    3240
ccaagactta aagagaata ctcagtcaaa attttcaagc cacttcaata tgtaagcata    3300
gatatcaaac aattgatgaa ggttattgag aaggaaaagt cagcagatca taatatgttg    3360
gaatcaaagc aatgggagac ttcttcttct tctaaggatg gggttctacg gctgggagat    3420
ggttctaagt tgtttccaaa tcttaaaagt ttgaagctat atggttttgt tgattataac    3480
tcaacccatt taccaatgga aatgttgcaa atcttattcc aacttaaaca ctttgaattg    3540
gaaggagcat ttattgaaga aattttcccc agcaatatac tgatttcaag ctctatggat    3600
ttacagagtt tggctctata taaactaccc aagcttaagc atttgtggag tgaagaatgc    3660
tcacgaaaca atatcacctc agttcttcaa catttgattt ttctaagaat ttcagattgt    3720
ggaagattga gtagtttaac tttagtgtca tcattagtgt gttttacaaa cttgaaaagt    3780
cttgcggttt ataaatgtga tagactaacc catttgctga atccttcgat ggctacaacg    3840
cttgtgcaac ttcaagattt gacaataaaa gaatgcaaaa gaatgagaag tgtaattgag    3900
gaaggatcaa ccgaagaaga tggaaatgat gaaatggttg tattcaacaa cctacgacat    3960
ttatacattt ttaattgttc caacctaaca agcttttatt gtgggagatg catcgttaaa    4020
ttcccatgtt tggaaagagt attcattcaa aattgtcctg aaatgaaggt cttttcactt    4080
ggaattgtaa gcacgcctcg tttgaaatat gaaaagttta ctttaatgaa tgattacgat    4140
gataaatggt gtcatctgaa atatcccaaa tatatgttgg tggaagatat gaatgtcatc    4200
accagagaat attgggagga taatgttgat accggaattc caaatttatt tgccgaacag    4260
agtttggagg aaaaccgatc tgaaaattct tcttcttcaa agaataatgt tgagaaagaa    4320
taaggaatta tatggatatt gttgtacact acttaatata tcatttcatc cacaaggaaa    4380
aggaagctgc caaataacct actcaatcct agcagatgcg ttcttttgcaa gccggctgtc    4440 gaagacttga accatatttt cacaacctgt gccaattcgc aaatagcctc tgggtcaaac    4500
tgcacgacaa aattggtgga aactttgata caaacagtat caaagccctc tgttggtctc    4560
ttggctcgct gaaacaatca aacagaaaga acatcattct ctcgatgtag gtgtggatct    4620
tcttttgtcc atttgggtgg aaagaaacaa taggattttc atagacatag aaagaagctt    4680
agtcacattt gggaagatat cgaaactttg attggaccat ggtcgagtag aaacaaaatg    4740
ttcaaagact acaatccaac atcaatcttt aaactttaga gctttgttag attaatgttt    4800
gttgtatatg gcttccctgt ggccaaagaa atatacattg taacaatggt ttgatgaaat    4860
gataatgaag tggtatggtg ttaaaatcac ctttatcact ctgtgtttca atttcaaaaa    4919
```

<210> SEQ ID NO 6
<211> LENGTH: 1410
<212> TYPE: PRT
<213> ORGANISM: Cucumis melo

<400> SEQUENCE: 6

Met Asp Ile Leu Ile Ser Val Thr Ala Lys Ile Ala Glu Tyr Thr Val
1               5                   10                  15

```
Glu Pro Val Gly Arg Gln Leu Gly Tyr Val Phe Phe Ile Arg Ser Asn
             20                  25                  30

Phe Gln Lys Leu Lys Thr Gln Val Glu Lys Leu Lys Ile Thr Arg Glu
         35                  40                  45

Ser Val Gln His Lys Ile His Ser Ala Arg Arg Asn Ala Glu Asp Ile
 50                  55                  60

Lys Pro Ala Val Glu Glu Trp Leu Lys Lys Val Asp Asp Phe Val Arg
 65                  70                  75                  80

Glu Ser Asp Glu Ile Leu Ala Asn Glu Gly His Gly Gly Leu Cys
                 85                  90                  95

Ser Thr Tyr Leu Val Gln Arg His Lys Leu Ser Arg Lys Ala Ser Lys
             100                 105                 110

Met Val Asp Glu Val Leu Glu Met Lys Asn Glu Gly Glu Ser Phe Asp
             115                 120                 125

Met Val Ser Tyr Lys Ser Val Ile Pro Ser Val Asp Cys Ser Leu Pro
             130                 135                 140

Lys Val Pro Asp Phe Ile Asp Phe Glu Ser Arg Lys Ser Ile Met Glu
145                 150                 155                 160

Gln Ile Met Asp Ala Leu Ser Asp Gly Asn Val His Arg Ile Gly Val
                 165                 170                 175

Tyr Gly Met Gly Gly Val Gly Lys Thr Met Leu Val Lys Asp Ile Leu
             180                 185                 190

Arg Lys Ile Val Glu Ser Lys Lys Pro Phe Asp Glu Val Val Thr Ser
             195                 200                 205

Thr Ile Ser Gln Thr Pro Asp Phe Arg Ser Ile Gln Gly Gln Leu Ala
 210                 215                 220

Asp Lys Leu Gly Leu Lys Phe Glu Gln Glu Thr Ile Glu Gly Arg Ala
225                 230                 235                 240

Thr Ile Leu Arg Lys Arg Leu Lys Met Glu Arg Ser Ile Leu Val Val
                 245                 250                 255

Leu Asp Asp Val Trp Glu Tyr Ile Asp Leu Glu Thr Ile Gly Ile Pro
             260                 265                 270

Ser Val Glu Asp His Thr Gly Cys Lys Ile Leu Phe Thr Thr Arg Ile
             275                 280                 285

Lys His Leu Ile Ser Asn Gln Met Cys Ala Asn Lys Ile Phe Glu Ile
             290                 295                 300

Lys Val Leu Gly Lys Asp Glu Ser Trp Asn Leu Phe Lys Ala Met Ala
305                 310                 315                 320

Gly Asp Ile Val Asp Ala Ser Asp Leu Lys Pro Ile Ala Ile Arg Ile
                 325                 330                 335

Val Arg Glu Cys Ala Gly Leu Pro Ile Ala Ile Thr Thr Val Ala Lys
             340                 345                 350

Ala Leu Arg Asn Lys Pro Ser Asp Ile Trp Asn Asp Ala Leu Asp Gln
             355                 360                 365

Leu Lys Ser Val Asp Val Gly Met Ala Asn Ile Gly Glu Met Glu Lys
             370                 375                 380

Lys Val Tyr Leu Ser Leu Lys Leu Ser Tyr Asp Cys Leu Gly Tyr Glu
385                 390                 395                 400

Glu Val Lys Leu Leu Phe Leu Leu Cys Ser Met Phe Pro Glu Asp Phe
                 405                 410                 415

Ser Ile Asp Val Glu Gly Leu His Val Tyr Ala Met Gly Met Gly Phe
             420                 425                 430

Leu His Gly Val Asp Thr Val Val Lys Gly Arg Arg Arg Ile Lys Lys
```

```
                435                 440                 445
Leu Val Asp Asp Leu Ile Ser Ser Leu Leu Gln Gln Tyr Ser Glu
            450                 455                 460

Tyr Gly Cys Asn Tyr Val Lys Met His Asp Met Val Arg Asp Val Ala
465                 470                 475                 480

Leu Leu Ile Ala Ser Lys Asn Glu His Val Arg Thr Leu Ser Tyr Val
                485                 490                 495

Lys Arg Ser Asn Glu Glu Trp Glu Glu Lys Leu Leu Gly Asn His
                500                 505                 510

Thr Ala Val Phe Ile Asp Gly Leu His Tyr Pro Leu Pro Lys Leu Thr
                515                 520                 525

Leu Pro Lys Val Gln Leu Leu Arg Leu Val Ala Gln Asp Cys Trp Glu
530                 535                 540

His Asn Lys Arg Val Ser Val Val Glu Thr Phe Phe Glu Glu Met Lys
545                 550                 555                 560

Glu Leu Lys Gly Leu Val Leu Ala Asn Val Asn Ile Ser Leu Met Gln
                565                 570                 575

Arg Thr Ser Asp Leu Tyr Ser Leu Ala Asn Ile Arg Val Leu Arg Leu
                580                 585                 590

Gln Ser Cys Asn Leu Leu Gly Ser Ile Asp Trp Ile Gly Glu Leu Lys
                595                 600                 605

Lys Leu Glu Ile Leu Asp Phe Ile Gly Ser Asn Ile Thr Gln Ile Pro
            610                 615                 620

Thr Thr Met Ser Gln Leu Thr Gln Leu Lys Val Leu Asn Leu Ser Ser
625                 630                 635                 640

Cys His Gln Leu Lys Val Ile Pro Pro Asn Ile Leu Ser Lys Leu Thr
                645                 650                 655

Lys Leu Glu Glu Leu Ser Leu Glu Thr Phe Asp Arg Trp Glu Gly Glu
                660                 665                 670

Glu Trp Tyr Glu Gly Arg Lys Asn Ala Ser Leu Ser Glu Leu Lys Cys
            675                 680                 685

Leu Arg His Leu Tyr Ala Leu Asn Leu Thr Ile Gln Asp Glu Glu Ile
            690                 695                 700

Met Pro Lys Asp Leu Phe Leu Ala Glu Glu Leu Lys Leu Gln Lys Phe
705                 710                 715                 720

Asn Ile Cys Ile Gly Tyr Gln Ser Lys Leu Lys Tyr Thr Phe Gly Pro
                725                 730                 735

Thr Asn Arg Ile Lys Asn Phe Ile Ala Ile Lys Met Glu Ser Gly Arg
                740                 745                 750

Cys Leu Asp Asn Trp Ile Lys Asn Leu Leu Lys Arg Ser Asp Asn Val
                755                 760                 765

Phe Leu Glu Gly Ser Ile Cys Ser Lys Val Leu His Ser Glu Leu Val
            770                 775                 780

Gly Ala Asn Asp Phe Val Ser Leu Pro Asn Leu Glu Lys Leu Glu Ile
785                 790                 795                 800

Val Asn Ala Lys Ser Leu Lys Met Ile Trp Ser Asn Asn Val Pro Ile
                805                 810                 815

Leu Asn Ser Phe Ser Lys Leu Glu Glu Ile Lys Ile Tyr Ser Cys Asn
                820                 825                 830

Asn Leu Gln Lys Val Leu Phe Pro Pro Asn Met Met Asp Ile Leu Thr
            835                 840                 845

Cys Leu Lys Val Leu Glu Ile Lys Asn Cys Asp Leu Leu Glu Gly Ile
850                 855                 860
```

-continued

```
Phe Glu Ala Gln Glu Pro Ile Ser Val Val Glu Ser Asn Asn Leu Pro
865                 870                 875                 880

Ile Leu Asn Ser Phe Ser Lys Leu Glu Glu Ile Arg Ile Trp Ser Cys
                885                 890                 895

Asn Asn Leu Gln Lys Val Leu Phe Pro Ser Asn Met Met Gly Ile Leu
                900                 905                 910

Pro Cys Leu Lys Val Leu Asp Ile Arg Gly Cys Glu Leu Leu Glu Gly
                915                 920                 925

Ile Phe Glu Val Gln Glu Pro Ile Ser Val Val Glu Ser Asn Ser Val
                930                 935                 940

Pro Ile Leu Asn Ser Phe Ser Lys Leu Glu Lys Ile Arg Ile Trp Ser
945                 950                 955                 960

Cys Asn Asn Leu Gln Lys Ile Leu Phe Pro Ser Asn Met Met Gly Ile
                965                 970                 975

Leu Thr Cys Leu Lys Val Leu Glu Ile Arg Asp Cys Glu Leu Leu Glu
                980                 985                 990

Gly Ile Phe Glu Val Gln Glu Pro Ile Ser Val Val Glu Ala Ser Pro
                995                1000                1005

Ile Val Leu Gln Asn Leu Ile Arg Leu Glu Leu Tyr Asn Leu Pro
                1010               1015               1020

Asn Leu Glu Tyr Val Trp Ser Lys Asn Pro Cys Glu Leu Leu Ser
                1025               1030               1035

Leu Glu Asn Ile Lys Ser Leu Thr Ile Glu Glu Cys Pro Arg Leu
                1040               1045               1050

Arg Arg Glu Tyr Ser Val Lys Ile Phe Lys Pro Leu Gln Tyr Val
                1055               1060               1065

Ser Ile Asp Ile Lys Gln Leu Met Lys Val Ile Glu Lys Glu Lys
                1070               1075               1080

Ser Ala Asp His Asn Met Leu Glu Ser Lys Gln Trp Glu Thr Ser
                1085               1090               1095

Ser Ser Ser Lys Asp Gly Val Leu Arg Leu Gly Asp Gly Ser Lys
                1100               1105               1110

Leu Phe Pro Asn Leu Lys Ser Leu Lys Leu Tyr Gly Phe Val Asp
                1115               1120               1125

Tyr Asn Ser Thr His Leu Pro Met Glu Met Leu Gln Ile Leu Phe
                1130               1135               1140

Gln Leu Lys His Phe Glu Leu Glu Gly Ala Phe Ile Glu Glu Ile
                1145               1150               1155

Phe Pro Ser Asn Ile Leu Ile Ser Ser Ser Met Asp Leu Gln Ser
                1160               1165               1170

Leu Ala Leu Tyr Lys Leu Pro Lys Leu Lys His Leu Trp Ser Glu
                1175               1180               1185

Glu Cys Ser Arg Asn Asn Ile Thr Ser Val Leu Gln His Leu Ile
                1190               1195               1200

Phe Leu Arg Ile Ser Asp Cys Gly Arg Leu Ser Ser Leu Thr Leu
                1205               1210               1215

Val Ser Ser Leu Val Cys Phe Thr Asn Leu Lys Ser Leu Ala Val
                1220               1225               1230

Tyr Lys Cys Asp Arg Leu Thr His Leu Leu Asn Pro Ser Met Ala
                1235               1240               1245

Thr Thr Leu Val Gln Leu Gln Asp Leu Thr Ile Lys Glu Cys Lys
                1250               1255               1260
```

-continued

```
Arg Met Arg Ser Val Ile Glu Glu Gly Ser Thr Glu Glu Asp Gly
    1265                1270                1275

Asn Asp Glu Met Val Val Phe Asn Asn Leu Arg His Leu Tyr Ile
    1280                1285                1290

Phe Asn Cys Ser Asn Leu Thr Ser Phe Tyr Cys Gly Arg Cys Ile
    1295                1300                1305

Val Lys Phe Pro Cys Leu Glu Arg Val Phe Ile Gln Asn Cys Pro
    1310                1315                1320

Glu Met Lys Val Phe Ser Leu Gly Ile Val Ser Thr Pro Arg Leu
    1325                1330                1335

Lys Tyr Glu Lys Phe Thr Leu Met Asn Asp Tyr Asp Asp Lys Trp
    1340                1345                1350

Cys His Leu Lys Tyr Pro Lys Tyr Met Leu Val Glu Asp Met Asn
    1355                1360                1365

Val Ile Thr Arg Glu Tyr Trp Glu Asp Asn Val Asp Thr Gly Ile
    1370                1375                1380

Pro Asn Leu Phe Ala Glu Gln Ser Leu Glu Glu Asn Arg Ser Glu
    1385                1390                1395

Asn Ser Ser Ser Ser Lys Asn Asn Val Glu Lys Glu
    1400                1405                1410

<210> SEQ ID NO 7
<211> LENGTH: 27
<212> TYPE: DNA
<213> ORGANISM: Artificial sequence
<220> FEATURE:
<223> OTHER INFORMATION: PCR primer F2-B2 for the marker L273

<400> SEQUENCE: 7
ggagagagaa tccgggacta agtgact                                        27

<210> SEQ ID NO 8
<211> LENGTH: 29
<212> TYPE: DNA
<213> ORGANISM: Artificial sequence
<220> FEATURE:
<223> OTHER INFORMATION: PCR primer F2-Br for the marker L273

<400> SEQUENCE: 8
taaccacctt ttccgatcaa atttcgtac                                      29

<210> SEQ ID NO 9
<211> LENGTH: 30
<212> TYPE: DNA
<213> ORGANISM: Artificial sequence
<220> FEATURE:
<223> OTHER INFORMATION: PCR primer F2-B2 Eco for the marker L246

<400> SEQUENCE: 9
attgatgaat ctacactcct cgatctcttc                                     30

<210> SEQ ID NO 10
<211> LENGTH: 30
<212> TYPE: DNA
<213> ORGANISM: Artificial sequence
<220> FEATURE:
<223> OTHER INFORMATION: PCR primer F2 Eco for the marker L246

<400> SEQUENCE: 10
gagttcaatc catttcaatg atttaagata                                     30
```

```
<210> SEQ ID NO 11
<211> LENGTH: 24
<212> TYPE: DNA
<213> ORGANISM: Artificial sequence
<220> FEATURE:
<223> OTHER INFORMATION: PCR primer V681 for the marker V681

<400> SEQUENCE: 11
ggaatcttgt tgaggccgag aggg                                           24

<210> SEQ ID NO 12
<211> LENGTH: 24
<212> TYPE: DNA
<213> ORGANISM: Artificial sequence
<220> FEATURE:
<223> OTHER INFORMATION: PCR primer V681R for the marker V681

<400> SEQUENCE: 12
gttgtatatg gcttccctgt agcc                                           24

<210> SEQ ID NO 13
<211> LENGTH: 24
<212> TYPE: DNA
<213> ORGANISM: Artificial sequence
<220> FEATURE:
<223> OTHER INFORMATION: PCR primer V588 for the marker V1684

<400> SEQUENCE: 13
caacaggctc aacagtgtat tcgg                                           24

<210> SEQ ID NO 14
<211> LENGTH: 24
<212> TYPE: DNA
<213> ORGANISM: Artificial sequence
<220> FEATURE:
<223> OTHER INFORMATION: PCR primer V551R for the marker V1684

<400> SEQUENCE: 14
gaagaaggtg acgagagaga tgcc                                           24

<210> SEQ ID NO 15
<211> LENGTH: 24
<212> TYPE: DNA
<213> ORGANISM: Artificial sequence
<220> FEATURE:
<223> OTHER INFORMATION: PCR primer V432 for the marker V432

<400> SEQUENCE: 15
aacttctcca actccctcca ctgc                                           24

<210> SEQ ID NO 16
<211> LENGTH: 24
<212> TYPE: DNA
<213> ORGANISM: Artificial sequence
<220> FEATURE:
<223> OTHER INFORMATION: PCR primer V432R for the marker V432

<400> SEQUENCE: 16
ttagagtggc aaagggaaga tggg                                           24

<210> SEQ ID NO 17
<211> LENGTH: 24
<212> TYPE: DNA
<213> ORGANISM: Artificial sequence
<220> FEATURE:
<223> OTHER INFORMATION: PCR primer GRP805 for the marker GRP805
```

```
<400> SEQUENCE: 17
atcccctgtt tccttcaaca accc                                          24

<210> SEQ ID NO 18
<211> LENGTH: 24
<212> TYPE: DNA
<213> ORGANISM: Artificial sequence
<220> FEATURE:
<223> OTHER INFORMATION: PCR primer GRP805R for the marker GRP805

<400> SEQUENCE: 18 aaccccccaag aagaagaaca accc                                         24

<210> SEQ ID NO 19
<211> LENGTH: 26
<212> TYPE: DNA
<213> ORGANISM: Artificial sequence
<220> FEATURE:
<223> OTHER INFORMATION: PCR primer M8 for the marker M8

<400> SEQUENCE: 19
ccgacgcatc tcccgacgcg ttgttg                                        26

<210> SEQ ID NO 20
<211> LENGTH: 27
<212> TYPE: DNA
<213> ORGANISM: Artificial sequence
<220> FEATURE:
<223> OTHER INFORMATION: PCR primer M8R for the marker M8

<400> SEQUENCE: 20
tcgtgaaggg ttttggagag tgagaaa                                       27

<210> SEQ ID NO 21
<211> LENGTH: 24
<212> TYPE: DNA
<213> ORGANISM: Artificial sequence
<220> FEATURE:
<223> OTHER INFORMATION: PCR primer LRR1 for the marker E

<400> SEQUENCE: 21
ccttagaaga agatgaagtc tccc                                          24

<210> SEQ ID NO 22
<211> LENGTH: 24
<212> TYPE: DNA
<213> ORGANISM: Artificial sequence
<220> FEATURE:
<223> OTHER INFORMATION: PCR primer LRR842R for the marker E

<400> SEQUENCE: 22
ctccactcag aattggtagg tgcc                                          24

<210> SEQ ID NO 23
<211> LENGTH: 24
<212> TYPE: DNA
<213> ORGANISM: Artificial sequence
<220> FEATURE:
<223> OTHER INFORMATION: PCR primer LRR915 for the marker D

<400> SEQUENCE: 23
aacaacttag aaccatctcc cagc                                          24

<210> SEQ ID NO 24
<211> LENGTH: 24
```

```
<212> TYPE: DNA
<213> ORGANISM: Artificial sequence
<220> FEATURE:
<223> OTHER INFORMATION: PCR primer LRR1 for the marker D

<400> SEQUENCE: 24
gttgttgaga gcaatagtgt accc                                          24

<210> SEQ ID NO 25
<211> LENGTH: 18
<212> TYPE: DNA
<213> ORGANISM: Artificial sequence
<220> FEATURE:
<223> OTHER INFORMATION: PCR primer Kana II

<400> SEQUENCE: 25
ccggctacct gcccattc                                                 18

<210> SEQ ID NO 26
<211> LENGTH: 18
<212> TYPE: DNA
<213> ORGANISM: Artificial sequence
<220> FEATURE:
<223> OTHER INFORMATION: PCR primer Kana III

<400> SEQUENCE: 26
gcgatagaag gcgatgcg                                                 18

<210> SEQ ID NO 27
<211> LENGTH: 24
<212> TYPE: DNA
<213> ORGANISM: Artificial sequence
<220> FEATURE:
<223> OTHER INFORMATION: PCR primer PicaA+

<400> SEQUENCE: 27
atgcgcatga ggctcgtctt cgag                                          24

<210> SEQ ID NO 28
<211> LENGTH: 24
<212> TYPE: DNA
<213> ORGANISM: Artificial sequence
<220> FEATURE:
<223> OTHER INFORMATION: PCR primer PicaA-

<400> SEQUENCE: 28
gacgcaacgc atcctcgatc agct                                          24

<210> SEQ ID NO 29
<211> LENGTH: 24
<212> TYPE: DNA
<213> ORGANISM: Artificial sequence
<220> FEATURE:
<223> OTHER INFORMATION: PCR primer Vat 632R

<400> SEQUENCE: 29
ctggtgatga cattcatatc ttcc                                          24

<210> SEQ ID NO 30
<211> LENGTH: 24
<212> TYPE: DNA
<213> ORGANISM: Artificial sequence
<220> FEATURE:
<223> OTHER INFORMATION: PCR primer Vat 632F

<400> SEQUENCE: 30
```

-continued

```
cccagcaaca tactgattcc aagc                                              24

<210> SEQ ID NO 31
<211> LENGTH: 18
<212> TYPE: DNA
<213> ORGANISM: Artificial sequence
<220> FEATURE:
<223> OTHER INFORMATION: PCR primer Kana R

<400> SEQUENCE: 31
ccggctacct gccattcg                                                     18

<210> SEQ ID NO 32
<211> LENGTH: 22
<212> TYPE: DNA
<213> ORGANISM: Artificial sequence
<220> FEATURE:
<223> OTHER INFORMATION: PCR primer LRR F

<400> SEQUENCE: 32
gttgttgaga gcaatagtgt ac                                                22

<210> SEQ ID NO 33
<211> LENGTH: 22
<212> TYPE: DNA
<213> ORGANISM: Artificial sequence
<220> FEATURE:
<223> OTHER INFORMATION: PCR primer LRR R

<400> SEQUENCE: 33
ccttagagaa gaatgaagtc tc                                                22
```